US012061199B2

(12) United States Patent
Boyden et al.

(10) Patent No.: US 12,061,199 B2
(45) Date of Patent: Aug. 13, 2024

(54) METHODS FOR DIAGNOSING NEOPLASTIC LESIONS

(71) Applicants: Massachusetts Institute of Technology, Cambridge, MA (US); Beth Israel Deaconess Medical Center, Inc., Boston, MA (US)

(72) Inventors: Edward Stuart Boyden, Chestnut Hill, MA (US); Andrew Hanno Beck, Brookline, MA (US); Yongxin Zhao, Quincy, MA (US); Octavian Bucur, Waltham, MA (US); Humayun Irshad, Malden, MA (US)

(73) Assignees: Massachusetts Institute of Technology, Cambridge, MA (US); Beth Israel Deaconess Medical Center, Inc, Boston, MA (US)

( * ) Notice: Subject to any disclaimer, the term of this patent is extended or adjusted under 35 U.S.C. 154(b) by 848 days.

(21) Appl. No.: 16/541,707

(22) Filed: Aug. 15, 2019

(65) Prior Publication Data
US 2020/0041514 A1  Feb. 6, 2020

Related U.S. Application Data

(63) Continuation of application No. PCT/US2018/019756, filed on Feb. 26, 2018.
(Continued)

(51) Int. Cl.
*G01N 15/1433* (2024.01)
*G01N 1/36* (2006.01)
(Continued)

(52) U.S. Cl.
CPC ......... *G01N 33/57415* (2013.01); *G01N 1/36* (2013.01); *G01N 15/1433* (2024.01);
(Continued)

(58) Field of Classification Search
CPC . G06T 2207/10056; G06T 2207/30096; G06T 7/00; G06V 20/69; G06V 10/40; G06V 20/695
See application file for complete search history.

(56) References Cited

U.S. PATENT DOCUMENTS 5,840,862 A  11/1998  Bensimon et al.
5,952,232 A   9/1999  Rothman
(Continued)

FOREIGN PATENT DOCUMENTS

CN  104350372 A  2/2015
CN  111848855 A  10/2020
(Continued)

OTHER PUBLICATIONS

Keenan et al., An automated machine vision system for the histological grading of cervical intraepithelial neoplasia (CIN), Journal of Pathology, J Pathol 2000; 192: pp. 351-362, DOI: 10.1002/1096-9896(2000) 9999 : 9999<: :AID-PATH708>3.0.CO;2-I.*
(Continued)

*Primary Examiner* — Guillermo M Rivera-Martinez
(74) *Attorney, Agent, or Firm* — Pierce Atwood LLP

(57) ABSTRACT

A method for diagnosing cancer in an expanded biological tissue sample of a patient comprising providing at least one sample image of the expanded biological tissue sample; providing a computer configured to analyze the sample; analyzing, with the computer, the sample detect and segment nuclei; calculating, with the computer, molecular characteristics of those nuclei; and determining, with the computer, a diagnosis of cancer of the sample by comparing the sample with a benign normal tissue reference.

30 Claims, 41 Drawing Sheets

Related U.S. Application Data

(60) Provisional application No. 62/463,265, filed on Feb. 24, 2017.

(51) Int. Cl.
*G01N 33/574* (2006.01)
*G02B 21/16* (2006.01)
*G16H 30/20* (2018.01)
*G16H 50/20* (2018.01)
*G01N 15/10* (2006.01)

(52) U.S. Cl.
CPC .............. *G02B 21/16* (2013.01); *G16H 30/20* (2018.01); *G16H 50/20* (2018.01); *G01N 2015/1006* (2013.01)

(56) References Cited

U.S. PATENT DOCUMENTS

| | | | |
|---|---|---|---|
| 6,107,081 A | 8/2000 | Feeback et al. | |
| 6,204,064 B1* | 3/2001 | Alberts | G01N 33/48 436/63 |
| 6,271,278 B1 | 8/2001 | Park et al. | |
| 6,287,870 B1 | 9/2001 | Wardlaw et al. | |
| 6,548,255 B2 | 4/2003 | Bensimon et al. | |
| 10,059,990 B2 | 8/2018 | Boyden et al. | |
| 10,309,879 B2 | 6/2019 | Chen et al. | |
| 10,317,321 B2 | 6/2019 | Tillberg et al. | |
| 10,364,457 B2 | 7/2019 | Wassie et al. | |
| 10,526,649 B2 | 1/2020 | Chen et al. | |
| 10,563,257 B2 | 2/2020 | Boyden et al. | |
| 10,774,367 B2 | 9/2020 | Fraser et al. | |
| 10,995,361 B2 | 5/2021 | Chen et al. | |
| 11,180,804 B2 | 11/2021 | Chen et al. | |
| 11,408,890 B2 | 8/2022 | Boyden et al. | |
| 2002/0176880 A1 | 11/2002 | Cruise et al. | |
| 2003/0120231 A1 | 6/2003 | Wang et al. | |
| 2004/0115629 A1* | 6/2004 | Panzer | C07K 14/47 435/325 |
| 2004/0137527 A1 | 7/2004 | Sleytr et al. | |
| 2004/0209317 A1 | 10/2004 | Ting | |
| 2004/0248326 A1 | 12/2004 | Ziaie et al. | |
| 2005/0034990 A1 | 2/2005 | Crooks et al. | |
| 2005/0069877 A1* | 3/2005 | Gandhi | A61P 43/00 435/325 |
| 2005/0090016 A1 | 4/2005 | Rich et al. | |
| 2005/0169962 A1 | 8/2005 | Bhatia et al. | |
| 2005/0196702 A1 | 9/2005 | Bryant et al. | |
| 2006/0000767 A1 | 1/2006 | Trauger et al. | |
| 2006/0003356 A1 | 1/2006 | Shaw et al. | |
| 2006/0110760 A1 | 5/2006 | Kim et al. | |
| 2006/0115146 A1 | 6/2006 | Ogura et al. | |
| 2006/0165912 A1 | 7/2006 | Koberstein et al. | |
| 2007/0023942 A1 | 2/2007 | Andino et al. | |
| 2007/0026432 A1 | 2/2007 | Ke et al. | |
| 2007/0042954 A1 | 2/2007 | Chen et al. | |
| 2007/0134902 A1 | 6/2007 | Bertino et al. | |
| 2007/0177786 A1* | 8/2007 | Bartels | G06V 20/69 382/168 |
| 2008/0139407 A1 | 6/2008 | Slootstra et al. | |
| 2008/0261834 A1 | 10/2008 | Simon et al. | |
| 2008/0286360 A1 | 11/2008 | Shoichet et al. | |
| 2009/0011141 A1 | 1/2009 | Carter et al. | |
| 2009/0011420 A1 | 1/2009 | Barron et al. | |
| 2009/0096133 A1 | 4/2009 | Doyle et al. | |
| 2009/0191627 A1 | 7/2009 | Fadeev et al. | |
| 2009/0241681 A1 | 10/2009 | Machauf et al. | |
| 2010/0041128 A1 | 2/2010 | Banes et al. | |
| 2010/0055161 A1 | 3/2010 | Ahn | |
| 2010/0056445 A1 | 3/2010 | Sharma et al. | |
| 2010/0068725 A1 | 3/2010 | Armbruster et al. | |
| 2010/0096334 A1 | 4/2010 | Edmiston et al. | |
| 2010/0111396 A1* | 5/2010 | Boucheron | G06V 10/771 382/133 |
| 2010/0119755 A1 | 5/2010 | Chung et al. | |
| 2010/0248977 A1 | 9/2010 | Johnston et al. | |
| 2011/0009171 A1 | 1/2011 | Watanabe et al. | |
| 2011/0070604 A1 | 3/2011 | Gimzewski et al. | |
| 2011/0087315 A1 | 4/2011 | Richardson-Burns et al. | |
| 2011/0091717 A1 | 4/2011 | Weiss et al. | |
| 2011/0091922 A1 | 4/2011 | Krishnan et al. | |
| 2011/0291357 A1 | 12/2011 | Boyle | |
| 2012/0025271 A1 | 2/2012 | Nakano | |
| 2012/0184670 A1 | 7/2012 | Kobayashi et al. | |
| 2012/0220478 A1 | 8/2012 | Shaffer | |
| 2012/0251527 A1 | 10/2012 | Reiser | |
| 2012/0310223 A1 | 12/2012 | Knox et al. | |
| 2013/0045503 A1 | 2/2013 | Miyawaki et al. | |
| 2013/0203605 A1 | 8/2013 | Shendure et al. | |
| 2014/0087139 A1 | 3/2014 | Rowley et al. | |
| 2014/0193651 A1 | 7/2014 | Kharlampieva et al. | |
| 2014/0364330 A1 | 12/2014 | Mershin et al. | |
| 2015/0086103 A1* | 3/2015 | Tsunomori | G06V 20/698 382/133 |
| 2015/0087001 A1 | 3/2015 | Gradinaru et al. | |
| 2015/0226743 A1* | 8/2015 | Weiss | G01N 33/57407 424/133.1 |
| 2015/0353989 A1 | 12/2015 | Fraser et al. | |
| 2015/0370961 A1 | 12/2015 | Zhang et al. | |
| 2015/0376261 A1 | 12/2015 | Steyaert et al. | |
| 2016/0116384 A1 | 4/2016 | Boyden et al. | |
| 2016/0252528 A1 | 9/2016 | Sangaralingham et al. | |
| 2016/0265046 A1 | 9/2016 | Zhang et al. | |
| 2016/0304952 A1 | 10/2016 | Boyden et al. | |
| 2016/0305856 A1 | 10/2016 | Chen et al. | |
| 2017/0067096 A1 | 3/2017 | Wassie et al. | |
| 2017/0081489 A1 | 3/2017 | Boyden et al. | |
| 2017/0087489 A1 | 3/2017 | Terlingen et al. | |
| 2017/0089811 A1 | 3/2017 | Chen et al. | |
| 2017/0103521 A1* | 4/2017 | Chukka | G06T 7/0012 |
| 2017/0182220 A1 | 6/2017 | Song et al. | |
| 2017/0199104 A1* | 7/2017 | Gradinaru | C12Q 1/6841 |
| 2017/0276598 A1* | 9/2017 | Ikuyama | G06T 7/11 |
| 2017/0323431 A1* | 11/2017 | Sarkar | G06T 5/003 |
| 2018/0119219 A1 | 5/2018 | Chen et al. | |
| 2019/0064037 A1 | 2/2019 | Boyden et al. | |
| 2019/0071656 A1 | 3/2019 | Chang et al. | |
| 2019/0113423 A1* | 4/2019 | Goodman | G06V 20/698 |
| 2019/0256633 A1 | 8/2019 | Gao et al. | |
| 2020/0049599 A1* | 2/2020 | Alexander | G01N 33/4833 |
| 2020/0081005 A1 | 3/2020 | Boyden et al. | |
| 2020/0217853 A1 | 7/2020 | Estandian et al. | |
| 2020/0271556 A1 | 8/2020 | Sarkar et al. | |
| 2020/0277664 A1 | 9/2020 | Frenz | |
| 2021/0130882 A1 | 5/2021 | Boyden et al. | |
| 2021/0190652 A1 | 6/2021 | Quevedo et al. | |
| 2021/0196856 A1 | 7/2021 | Boyden et al. | |
| 2023/0104998 A1 | 4/2023 | Estandian et al. | |
| 2023/0332207 A1 | 10/2023 | Cui et al. | |

FOREIGN PATENT DOCUMENTS

| | | |
|---|---|---|
| CN | 112574089 A | 3/2021 |
| EP | 3159361 A1 | 4/2017 |
| JP | 2005291759 A | 10/2005 |
| JP | 2006036957 A | 2/2006 |
| JP | 2008286694 A | 11/2008 |
| JP | 2009191125 A | 8/2009 |
| JP | 2014005231 A | 1/2014 |
| WO | 0008212 A1 | 2/2000 |
| WO | 2007103665 A2 | 9/2007 |
| WO | 2008058302 A1 | 5/2008 |
| WO | 2010048605 A1 | 4/2010 |
| WO | 2012112689 A1 | 8/2012 |
| WO | 2012142664 A1 | 10/2012 |
| WO | 2014025392 A1 | 2/2014 |
| WO | 2014152984 A1 | 9/2014 |
| WO | 2015041755 A1 | 3/2015 |
| WO | 2015127183 A2 | 8/2015 |
| WO | 2016040489 A1 | 3/2016 |
| WO | 2017027367 A1 | 2/2017 |
| WO | 2017027368 A1 | 2/2017 |
| WO | WO-2017031249 A1 * | 2/2017 |
| WO | 2017079406 A1 | 5/2017 |

(56) References Cited

FOREIGN PATENT DOCUMENTS

| WO | 2017147435 A1 | 8/2017 |
|---|---|---|
| WO | 2018157074 A1 | 8/2018 |
| WO | 2019144391 A1 | 8/2019 |
| WO | 2021051011 A1 | 3/2021 |
| WO | 2021183667 A1 | 9/2021 |
| WO | 2022100696 A1 | 3/2022 |

OTHER PUBLICATIONS

Keenan et al., An automated machine vision system for the histological grading of cervical intraepithelial neoplasia (CIN), J Pathol. Nov. 2000, 192(3):351-62, doi: 10.1002/1096-9896(2000)9999:9999<::AID-PATH708>3.0.CO;2-I.*

Wang et al., Detection and classification of thyroid follicular lesions based on nuclear structure from histopathology images, Cytometry A. May 2010, 77(5):485-94, doi: 10.1002/cyto.a.20853. PMID: 20099247; PMCID: PMC3010854.*

Gann et al., Development of a nuclear morphometric signature for prostate cancer risk in negative biopsies, PLoS One, Jul. 26, 2013, pp. 1-9, doi: 10.1371/journal.pone.0069457.*

New England BioLabs, "Proteinase K", P8102S product datasheet, 1 page, accessed Nov. 17, 2020.

Product information brochure, Flocryltm MBA, SNF Floerger, pp. 1-4, accessed Nov. 17, 2020.

"Crosslinking and Photoactivatable Reagents", Invitrogen, Chapter 5 in "Molecular ProbesTM Handbook A Guide to Fluorescent Probes and Labeling Technologies", 11th Edition, 2010, 171-188.

"Proteinase K from Tritirachium album, solution", Serva Electrophoresis, Instruction Manual, Cat. No. 33755, 1 page, publicly available prior to Feb. 1, 2017.

Akhavan, A. et al., "Molecular Epizootiology of Rodent Leishmaniasis in a Hyperendemic Area of Iran", Iranian J Publ Health, vol. 39, No. 1, 2010, 1-7.

Bi, X. et al., "In situ-forming cross-linking hydrogel systems: chemistry and biomedical applications", In: "Emerging Concepts in Analysis and Applications of Hydrogels", Intech, Aug. 24, 2016, 131-158.

Dilorenzo, F. et al., "Nanostructural Heterogeneity in Polymer Networks and Gels", Polymer Chemistry, vol. 6, 2015, 5515-5528.

Goor, Olga J. et al., "Introduction of anti-fouling coutings at the surface of supramolecular elastomeric materials via post-modification of reactive supramolecular additives", Polymer Chem., vol. 8, No. 34, Jan. 1, 2017, 5228-5238.

Jiang, Y. et al., "Click hydrogels, microgels and nanogels: emerging platforms for drug delivery and tissue engineering", Biomaterials, vol. 35, No. 18, Jun. 1, 2014, 4969-4985.

Majcher, M. J. et al., "Hydrogel synthesis and design", In: "Cellulose-Based Superabsorbent Hydrogels", Springer International Publishing, Jan. 1, 2018, 1-41.

Meng, H., "Localization of a Blood Pressure Quantitative Trait Locus (QTL) to a 1.7cM Interval on Rat Chromosome 9", Medical College of Ohio, dissertation, 2002, 1-158.

Orakdogen, N. et al., "Correlation Between Crosslinking Efficiency and Spatial Inhomogeneity in Poly(acrylamide) Hydrogels", Polymer Bulletin, vol. 57, 2006, 631-641.

Oshima, K. et al., "Model Polyelectrolyte Gels Synthesized by End-Linking of Tetra-Arm Polymers with Click Chemistry: Synthesis and Mechanical Properties", Macromolecules, vol. 47, 2014, 7573-7580.

Parang, B. et al., "Myeloid translocation genes differentially regulate colorectal cancer programs", Oncogene, vol. 35, 2016, 6341-6349.

Sakai, T. et al., "Design and Fabrication of a High-Strength Hydrogel with Ideally Homogenous Network Structure from Tetrahedron-Like Macromonomers", Macromolecules, vol. 41, 2008, 5379-5384.

Xu, J. et al., "Bioorthogonally cross-linked hydrogel network with precisely controlled disintegration time over a broad ragne", J. Am. Chem.Soc., vol. 136, No. 11, Mar. 19, 2014, 4105-4108.

Yazici, I. et al., "Spatial Inhomogeneity in Poly(acrylic acid) Hydrogels", Polymer, vol. 46, 2005, 2595-2602.

Zhou, C. et al., "Synthesis and characterization of well-defined PAA-PEG multi-responsive hydrogels by ATRP and click chemistry", RSC ADV., vol. 4, No. 97, Jan. 1, 2014, 54631-54640.

Duan, C. et al., "Application of antigen retrieval method in hMAM immunohistochemical staining of old paraffin-embedded specimens", Academy of Military Medical Sciences, vol. 38(12), Dec. 31, 2014, 965-967.

Ferri, A., "Expansion Microscopy: A New Approach to Microscopic Evaluation", Master's thesis, retrieved from https://scholarcommons.sc.edu/etd/6034, 2020.

Asano, S. M. et al., "Expansion Microscopy: Protocols for Imaging Proteins and RNA in Cells and Tissues", Current Protocols in Cell Bio., vol. 80, No. 1, Online: DOI: 10.1002/cpcb.56. Retrieved from the Internet: URL:https://onlinelibrary.wiley.com/doi/full-XML/10.1002/cpcb.56> [retrieved on Feb. 26, 2021], Sep. 2, 2018, p. 41.

Yu, C-C et al., "Expansion microscopy of C. elegans", ELIFE, [Online] DOI: 10.7554/eLife.46249. Retrieved from the Internet: URL:https://elifesciences.org/articles/46249> [retrieved on Feb. 26, 2021], May 1, 2020, pp. 125.

Office Action dated Apr. 4, 2018 from U.S. Appl. No. 14/627,310, filed Feb. 20, 2015.

"Epitope Recovery Methods for IHC", Nov. 7, 2015, ThermoFisher Scientific, pp. 1-2.

Ai, H. et al., "Exploration of new chromophore structures leads to the identification of improved blue fluorescent proteins", Biochemistry, 46, 2007, 5904-10.

Bates, M. et al., "Multicolor super-resolution imaging with photoswitchable fluorescent probes", Science, 317, 2007, 1749-1753.

Batish, M. et al., "Neuronal mRNAs Travel Singly into Dendrites", PNAS, vol. 109(12), 2012, 4645-4650.

Beliveau, B. et al., "Versatile design and synthesis platform for visualizing genomes with Oligopaint Fish probes", PNAS, vol. 109(52): pfa, 2012, 21301-21306.

Bleckmann, J. et al., "Surface-Layer Lattices as Patterning Element for Multimeric Extremozymes", Small Journal, 2013, 1-8.

Bokman, S. H. et al., "Renaturation of Aequorea gree-fluorescent protein", Biochem. Biophys. Res. Commun., 101, 1981, 1372-80.

Bossi, M. et al., "Multicolor far-field fluorescence nanoscopy through isolated detection of distinct molecular species", Nano Lett., 8, 2008, 2463-8.

Breitwieser, A. et al., "Magnetic Beads Functionalized with Recombinant S-Layer Protein Exhibit High Human IgG-Binding and Anti-Fouling Properties", Current Topics in Peptide & Protein Research, vol. 17, 2016, 45-55.

Bruchez, M. et al., "Semiconductor nanocrystals as fluorescent biological labels", Science, vol. 281, 1998, 2013-6.

Buckley, P. et al., "Cytoplasmic Intron Sequence-Retaining Transcripts Can Be Dendritically Targeted via ID Element Retrotransposons", Neuron, vol. 69, 2011, 877-884.

Buenrostro, J. D. et al., "ATAC-seq: A Method for Assaying Chromatin Accessibility Genome-Wide: ATAC-seq for Assaying Chromatin Accessibility", In: "Current Protocols in Molecular Biology", Wiley, New York, NY, Jan. 5, 2015.

Buxbaum, A. et al., "Single-Actin mRNA Detection in Neurons Reveals a Mechanism for Regulating Its Translatability", Science, vol. 343, 2014, 419-422.

Cabili, M. et al., "Localization and abundance analysis of human lncRNAs at single-cell and single-molecule resolution", Genome Biology, vol. 16(20), 2015.

Cai, et al., Nat Meth., 10, 2013, 540-547.

Cajigas, I. et al., "The local transcriptome in the synaptic neuropil revealed by deep sequencing and high-resolution imaging", Neuron 74, 2012, 453-466.

Cao, W., "DNA ligases and ligase-based technologies", Clinical and Applied Immunology Reviews, Elsevier, Amsterdam, NL, vol. 2, No. 1, Jan. 15, 2001, 33-43.

(56) References Cited

OTHER PUBLICATIONS

Carpenter, A. E. et al., "CellProfiler: image analysis software for identifying and quantifying cell phenotypes", Genome Biol., 7, 2006, R100.
Chang, J-B et al., "Iterative expansion microscopy", Nature Methods, 14(6), Jun. 2017, 593-599.
Chen, F. et al., "Expansion Microscopy", Science, 347(6621): Jan. 15, 2015, 1-18.
Chen, F. et al., "Nanoscale Imaging of RNA with Expansion Microscopy", Nature Methods, 13(8): Aug. 2016, 679-684.
Chen, F. et al., "Supplementary Material for Expansion Microscopy", Science, 347(6221), Jan. 15, 2015, 543-548.
Chen, K. et al., "Spatially resolved, highly multiplexed RNA profiling in single cells", Science. vol. 348(6233), 2015, aaa6090-aaa6090.
Chen, X. et al., "[Supplementary material] ATAC-see reveals the accessible genome by transposase-mediated imaging and sequencing", Nature Methods, vol. 13, No. 12, Oct. 17, 2016, 1813-1828.
Choi, H. et al., "Next-Generation in Situ Hybridization Chain Reaction: Higher Gain, Lower Cost, Greater Durability", ACS Nano 8(5), 2014, 4284-4294.
Choi, H. et al., "Programmable in situ amplification for multiplexed imaging of mRNA expression", Nature Biotechnology, 28(11), 2010, 1208-1212.
Chozinski, T. et al., "Expansion microscopy with conventional antibodies and fluorescent proteins", Nature Methods, vol. 13(6), 2016, 485-491.
Chu, J. et al., "Non-invasive intravital imaging of cellular differentiation with a bright red-excitable fluorescent protein", Nat. Methods, 11, 2014, 572-8.
Clemson, C. et al., "An architectural role for a nuclear noncoding RNA: NEAT1 RNA is essential for the structure of paraspeckles", Molecular Cell, 33, 2009, 717-26.
Cormack, B. P. et al., "FACS-optimized mutants of the green fluorescent protein (GFP)", Gene, 173, 1996, 33-8.
Cubitt, A. B. et al., "Understanding structure-function relationships in the Aequorea victoria green fluorescent protein", Methods Cell Biol., 58, 1999, 19-30.
Dedecker, P. et al., "Localizer: fast, accurate, open-source, and modular software package for superresolution microscopy", J. Biomed. Opt., 17, 2012, 126008.
Edelstein, A. et al., "Computer control of microscopes using μManager", Curr. Protoc. Mol. Biol. Chapter 14, Unit14.20, 2010.
English, B. P. et al., "A three-camera imaging microscope for high-speed single-molecule tracking and super-resolution imaging in living cells", in SPIE Nanosci. + Eng. (Mohseni, H., Agahi, M. H. & Razeghi, M.) 955008 (International Society for Optics and Photonics, 2015). doi:10.1117/12.2190246.
Engreitz, J. et al., "The Xist lncRNA exploits three-dimensional genome architecture to spread across the X chromosome", Science 341, 2013, 1237973.
Femino, A. et al., "Visualization of Single RNA Transcripts in Situ", Science, vol. 280, 1998, 585-590.
Feng, G. et al., "Imaging neuronal subsets in transgenic mice expressing multiple spectral variants of GFP", Neuron, 28, 2000, 41-51.
Filonov, G. S. et al., "Bright and stable near-infrared fluorescent protein for in vivo imaging", Nat. Biotechnol., 29, 2011, 757-61.
Fouz, M. et al., "Bright Fluorescent Nanotags from Bottlebrush Polymers with DNA-Tipped Bristles", ACS Central Science, vol. 1, 2015, 431-438.
Freifeld, L. et al., "Expansion microscopy of zebrafish for neuroscience and developmental biology studies", PNAS (online), Nov. 21, 2017, E10799-E10808.
Goedhardt, J. et al., "Structure-guided evolution of cyan fluorescent proteins towards a quantum yield of 93%", Nat. Commun., 3, 2012, 751.
Griesbeck, O. et al., "Reducing the environmental sensitivity of yellow fluorescent protein. Mechanism and applications", J. Biol. Chem., 276, 2001, 29188-94.
Gurskaya, N. G. et al., "Engineering of a monomeric green-to-red photoactivatable fluorescent protein induced by blue light", Nat. Biotechnol., 24, 2006, 461-5.
Gyorvary, E. S. et al., "Self-Assembly and Recrystallization of Bacterial S-Layer Proteins at Silicon Supports Imaged in Real Time by Atomic Force Microscopy", Journal of Microscopy, vol. 212, 2003, 300-306.
Habuchi, S. et al., "mKikGR, a monomeric photoswitchable fluorescent protein", PLoS One, 3, 2008, e3944.
Hackstadt, T., "Steric hindrance of antibody binding to surface proteins of Coxiella burnetti by phase I lipopolysaccharide", Infect Immun, 56, 1998, 802-807.
Heim, R. et al., "Engineering green fluorescent protein for improved brightness, longer wavelengths and fluorescence resonance energy transfer", Curr. Biol., 6, 1996, 178-82.
Heim, R. et al., "Wavelength mutations and posttranslational autoxidation of green fluorescent protein", Proc. Natl. Acad. Sci. U.S.A., 91, 1994, 12501-4.
Hoffman, T. L. et al., "A Biosensor Assay for Studying Ligand-Membrane Receptor Interactions: Binding of Antibodies and HIV-1 Env to Chemokine Receptors", PNAS, 97(21), 2000, 11215-11220.
Huang, B. et al., "Whole-cell 3D Storm reveals interactions between cellular structures with nanometer-scale resolution", Nat. Methods, 5, 2008, 1047-1052.
Huisken, J. et al., "Optical Sectioning Deep Inside Live Embryos by Selective Plane Illumination Microscopy", Science. vol. 305, 2004, 1007-1009.
Hunt, et al., "High temperature antigen retrieval and loss of nuclear morphology: a comparison of microwave\rand autoclave techniques", J. Clin. Pathol. 49,1996, 767-770.
Jekel, P A. et al., "Use of endoproteinase Lys-C from Lysobacter enzymogenes in protein sequence analysis", Anal. Biochem., 134,1983, 347-354.
Jimenez, N. et al., "A Novel Approach for Intracellular 3D Immuno-Labeling for Electron Tomography", Traffic,13, 2012, 926-933.
Jung, H. et al., "Axonal mRNA localization and local protein synthesis in nervous system assembly, maintenance and repair", Nat. Rev. Neurosci., vol. 13(5), 2012, 308-24.
Kakimoto, K. et al., "Hypothesis for the mechanism for heat-induced antigen retrieval occurring on fresh frozen sections without formalin-fixation in immunohistochemistry", J Mol Histol., 39, 2008, 389-399.
Kaur, et al., Biochemistry 45, 2006, 7347-7355.
Ke, R. et al., "In situ sequencing for RNA analysis in preserved tissue and cells", Nature Methods, vol. 10(9), 2013, 857-60.
Kroon, D.-J, "B-spline Grid, Image and Point based Registration", Matlab Cent. at <http://www.mathworks.com/matlabcentral/fileexchange/20057-b-spline-grid--image-and-point-based-registration>.
Laemmli, U. K., "Cleavage of structural proteins during the assembly of the head of bacteriophage T4", Nature, 227, 1970, 680-685.
Lam, A. J. et al., "Improving FRET dynamic range with bright green and red fluorescent proteins", Nat. Methods, 9, 2012, 1005-12.
Lee, J. et al., "Highly Multiplexed Subcellular RNA Sequencing in Situ", Duplicate—RefID 308986 Science, vol. 343, 2014, 1360-1363.
Lein, E. et al., "Genome-wide atlas of gene expression in the adult mouse brain", Nature, vol. 445, 2007, 168-76.
Levsky, J. et al., "Fluorescence in situ hybridization: past, present and future", Journal of Cell Science, 116, 2003, 2833-2838.
Lieberman-Aiden, E. et al., "Comprehensive mapping of long-range interactions reveals folding principles of the human genome", Science 326, 2009, 289-93.
Livet, J. et al., "Transgenic strategies for combinatorial expression of fluorescent proteins in the nervous system", Nature, 450, 2007, 56-62.
Lowe, D. G., "Distinctive Image Features from Scale-Invariant Keypoints", Int. J. Comput. Vis., 60, 2004, 91-110.
Lubeck, E. et al., "Single-cell in situ RNA profiling by sequential hybridization", Nature Methods, vol. 11(4), 2014, 360-1.
Lubeck, E. et al., "Single-cell systems biology by super-resolution imaging and combinatorial labeling", Nature Methods, vol. 9, 2012, 743-8.

(56) References Cited

OTHER PUBLICATIONS

Markwardt, M. L. et al., "An improved cerulean fluorescent protein with enhanced brightness and reduced reversible photoswitching", PLoS One, 6, 2011, e17896.
McKinney, S. A. et al., "A bright and photostable photoconvertible fluorescent protein", Nat. Methods, 6, 2009, 131-3.
Mito, M. et al., "Simultaneous multicolor detection of RNA and proteins using super-resolution microscopy", Methods, doi:10.1016/j.ymeth.2015.11.007., 2015.
Mortensen, K. I. et al., "Optimized localization analysis for singlemolecule tracking and super-resolution microscopy", Nat. Methods, 7, 010, 377-81.
Nagai, T. et al., "A variant of yellow fluorescent protein with fast and efficient maturation for cell-biological applications", Nat. Biotechnol., 20, 2002, 87-90.
Nagre, R. D. et al., "Thermosaline Resistant Acrylamide-Based Polyelectrolyte as Filtration Control Additive in Aqueous-Based Mud", Petroleum and Coal, vol. 56, No. 3, 2014, 222-230.
Nilsson, M. et al., "RNA-templated DNA ligation for transcript analysis", Nucleic Acids Research, Information Retrieval LTD., vol. 29, No. 2, Jan. 15, 2001, 578-581.
Ormo, M. et al., "Crystal structure of the Aequorea victoria green fluorescent protein", Science, 273, 1996, 1392-5.
Panning, B. et al., "X chromosome Inactivation is Mediated by by Xist RNA stabilization", Cell. vol. 90, 1997, 907-16.
Park, Y. N et al., "Detection of Hepatitis C Virus RNA Using Ligation-Dependent Polymerase Chain Reaction in Formalin-Fixed, Paraffin-Embedded Liver Tissues", Amer. J. of Pathol., vol. 149, No. 5, Nov. 1, 1996, 1485-1491.
Plath, K. et al., "Xist RNA and the mechanism of X chromosome inactivation", Annu. Rev. Genet. 36, 2002, 233-78.
Pum, D. et al., "Reassembly of S-Layer Proteins", Nanotechnology, 2014, 1-15.
Raj, A. et al., "Detection of individual endogenous RNA transcripts in situ using multiple singly labeled probes", Methods in Enzymology, vol. 472 (Elsevier Inc.), 2010, 365-386.
Raj, A. et al., "Imaging individual mRNA molecules using multiple singly labeled probes", Nat. Methods 5(10), 2008, 877-879.
Randall, K. J. et al., "A dual-label technique for the immunohistochemical demonstration of T-lymphocyte subsets in formalin-fixed, paraffin-embedded rat lymphoid tissue", Toxicol. Pathol., 36, 2008, 795-804.
Rego, E. H. et al., "Nonlinear structured-illumination microscopy with a photoswitchable protein reveals cellular structures at 50-nm resolution", Proc. Natl. Acad. Sci. U.S.A., 109, 2012, E135-43.
Reinhart-King, C. A. et al., "Dynamics and Mechanics of Endothelial Cell Spreading", Biophysical J, 89(1): Jul. 1, 2005, 676-689.
Rose, R. et al., "Ocular ascorbate transport and metabolism", A. Comp. Physiol., 100,1991, 273-85.
Rothbauer, M. et al., "Exploitation of S-Layer Anisotropy: pH-Dependent Nanolayer Orientation for Cellular Micropatterning,", Acs NANO, published online, 2013.
Schindelin, J. et al., "Fiji: an open-source platform for biological-image analysis", Nature methods, vol. 9, 2012, 676-82.
Schnell, U. et al., "Immunolabeling artifacts and the need for live-cell imaging", Nat. Methods, 9, 2012, 152-158.
Seneviratne, U. et al., "S-nitrosation of proteins relevant to Alzheimer's disease during early stages of neurodegeneration", Proc. Natl. Acad. Sci. U. S. A. 1521318113—(2016). doi:10.1073/pnas.1521318113.
Shah, S. et al., "Single-molecule RNA detection at depth via hybridization chain reaction and tissue hydrogel embedding and clearing", Development in Review, 2016.
Shaner, N. C. et al., "Improved monomeric red, orange and yellow fluorescent proteins derived from *Discosoma* sp. red fluorescent protein", Nat. Biotechnol., 22, 2004, 1567-72.
Shaner, N. C. et al., "Improving the photostability of bright monomeric orange and red fluorescent proteins", Nat. Methods, 5, 2008, 545-51.
Shcherbakova, D. M., "An orange fluorescent protein with a large Stokes shift for single-excitation multicolor FCCS and FRET imaging", J. Am. Chem. Soc., 134, 2012, 7913-23.
Shcherbo, D. et al., "Far-red fluorescent tags for protein imaging in living tissues", Biochem. J., 418, 2009, 567-74.
Sleytr, U. et al., "Heterologous Reattachment of Regular Arrays of Glycoproteins on Bacterial Surfaces", Nature, vol. 257, 1975, 400-401.
Sleytr, U. et al., "S-Layers Principles and Applications", FEMS Microbiology Rev., 2014, 1-42.
Sniegowski, J. A. et al., "Maturation efficiency, trypsin sensitivity, and optical properties of Arg96, Glu222, and Gly67 variants of green fluorescent protein", Biochem. Biophys. Res. Commun., 332, 2005, 657-63.
Steward, O. et al., "Compartmentalized synthesis and degradation of proteins in neurons", Neuron, vol. 40, 2003, 347-359.
Steward, O. et al., "Synaptic activation causes the mRNA for the leg Arc to localize selectively near activated postsynaptic sites on dendrites", Neuron, vol. 21, 1998, 741-751.
Strack, R, "Imaging Bigger is Better for Super-Resolution", Nature Methods, 12(13), Mar. 1, 2015, 169.
Subach, F. V. et al., "Bright monomeric photoactivatable red fluorescent protein for two-color super-resolution sptPALM of live cells", J. Am. Chem. Soc., 132, 2010, 6481-91.
Subach, O. M. et al., "An Enhanced Monomeric Blue Fluorescent Protein with the High Chemical Stability of the Chromophore", PLoS One, 6, 2011, e28674.
Thevenaz, P. et al., "A pyramid approach to subpixel registration based on intensity", IEEE Trans. Image Process., 7, 1998, 27-41.
Tillberg, P. et al., "Protein-Retention Expansion Microscopy of Cells and Tissues Labeled Using Standard Fluorescent Proteins and Antibodies", Nature Biotechnology vol. 34(9), 2016, 987-995.
Van Vliet, et al., "The Biomechanics Toolbox: Experimental Approaches for Living Cells and Biomolecules", Acta Materialia, 51, Aug. 23, 2003, 5881-5905.
Vedaldi, A. et al., Vlfeat. in Proc. Int. Conf. Multimed.—MM '10 1469 (ACM Press, 2010). doi:10.1145/1873951.1874249.
Wachter, R. M. et al., "Sensitivity of the yellow variant of green fluorescent protein to halides and nitrate", Curr. Biol., 9, 1999, R628-R629.
Wang, F. et al., "RNAscope: A novel in situ RNA analysis platform for formalin-fixed, paraffin-embedded tissues", Journal of Molecular Diagnostics, vol. 14(1), 2012, 22-29.
Wu, C. C. et al., "A method for the comprehensive proteomic analysis of membrane proteins", Nat. Biotechnol., 21,2003, 532-8.
Xingqi, C. et al., "ATAC-see reveals the accessible genome by transposase-mediated HJ, imaging and sequencing", Nature Methods, vol. 13, No. 12, Dec. 1, 2016, 1013-1020.
Zhang, D. et al., "Dynamic DNA nanotechnology using strand-displacement reactions", Nature Chemistry, vol. 3, 2011, 103-113.
Zhang, R. et al., "Tools for GPCR Drug Discovery", Acta Pharmacologica Sinica, 33, 2012, 372-384.
Zimmerman, T. A. et al., "Adapting the stretched sample method from tissue profiling to imaging", Proteomics, 8, 2008, 3809-3815.
Ke, R., et al., "In Situ Sequencing for RNA Analysis in Preserved Tissue and Cells," Nature Methods, 10(9): pp. 857-860 (2013).
Boutin, J. A. "Myristoylation." Cell. Signal, 9(1):15-35. (Jan. 1997) doi: 10.1016/50898-6568(96)00100-3.
Bullock, G. R. "The current status of fixation for electron microscopy: A review." J. Microsc., 133: 1-15. (1984). doi:10.1111/j.1365-2818.1984.tb00458.x.
Cochilla, A. J. et al. "Monitoring secretory membrane with FM1-43 flourescence." Annu. Rev. Neurosci. 22:1-10 (1999). doi:10.1146/annurev.neuro.22.1.1.
Danilczyk, U. G., et al. "Functional relationship between calreticulin, calnexin, and the endoplasmic reticulum luminal domain of calnexin." J. Biol. Chem. 275(17): 13089-13097 (2000). doi:10.1074/jbc.275.17.13089.
English, A. R. et al. "Endoplasmic reticulum structure and interconnections with other organelles." Cold Spring Harbor Perspectives in Biology 2013;5:a013227. doi:10.1101/cshperspect.a013227.

(56) References Cited

OTHER PUBLICATIONS

Guo A. et al. "The Critical Role of Surface Chemistry In Protein Microarrays" in Functional Protein Microarrays in Drug Discovery, edt. Paul Predki, p. 53-71 (CRC press, Boca Raton, 2007).
Guo, H. et al. "An efficient procedure for protein extraction from formalin-fixed, Paraffin-embedded tissues for reverse phase protein arrays." Proteome Sci. 10:56 (2012). doi: 10.1186/1477-5956-10-56.
Honig, M. G. et al. "DiI and DiO: versatile fluorescent dyes for neuronal labeling and pathway tracing." Trends Neurosci. 12(9):333-341 (1989). doi: 10.1016/0166-2236(89)90040-4.
Honig, M. G. et al. "Fluorescent carbocyanine dyes allow living neurons of identified origin to be studied in long-term cultures." J. Cell Biol. 103:171-187 (1986). doi:10.1083/jcb.103.1.171.
International Search Report and Written Opinion from the International Searching Authority dated May 17, 2018 from corresponding International Patent Application No. PCT/US2018/19756 Filed on Feb. 26, 2018.
Jamur, M. C. et al. "Permeabilization of Cell Membranes." in Immunocytochemical Methods and Protocols 588:63-6 (2010). doi:10.1007/978-1-59745-324-0...9.
Ku, T. et al. "Multiplexed and scalable super-resolution imaging of three-dimensional protein localization in size-adjustable tissues." Nat. Biotechnol. 34(9): 973-981 (2016). doi:10.1038/nbt.3641.
Lakkaraju, A. K. K. et al. "Palmitoylated calnexin is a key component of the ribosome-translocon complex." EMBO J. 31, 1823-1835 (2012). doi:10.1038/emboj.2012.15.
Linder, M. E. et al. "Palmitoylation: Policing protein stability and traffic." Nature Reviews Molecular Cell Biology 8:74-84 (2007). doi:10.1038/nrm2084.
Mabrey, S. et al. "Investigation of phase transitions of lipids and lipid mixtures by sensitivity differential scanning calorimetry." Proc. Natl. Acad. Sci. 73(11): 3862-3866 (1976). doi: 10.1073/pnas.73.11.3862.
Menon, A. K. "Lipid modifications of proteins." in 'Biochemistry of Lipids, Lipoproteins and Membranes' 39-58 (2008). doi:10.1016/8978-044453219-0.50004-0.
Myhill, N. et al. "The subcellular distribution of calnexin is mediated by PACS-2." Mol. Biol. Cell 19:2777-2788 (2008). doi:10.1091/mbc.E07-10-0995.
Revelo, N. H. et al. "A new probe for super-resolution imaging of membranes elucidates trafficking pathways." J. Cell Biol. 205(4):591-606 (2014). doi:10.1083/jcb.201402066.
Sarrazin, S. et al. "Heparan sulfate proteoglycans." Cold Spring Harb. Perspect. Biol. 2011;3:a004952. doi: 10.1101/cshperspect.a004952.
Scicchitano, M. S., et al. "Protein extraction of formalin-fixed, paraffin-embedded tissue enables robust proteomic profiles by mass spectrometry." J. Histochem. Cytochem. 57(9): 849-860 (2009). doi:10.1369/jhc.2009.953497.
Seifert, U. "Configurations of fluid membranes and vesicles." Adv. Phys. 46(1):13-137 (1997). doi:10.1080/00018739700101488.
Shen, K., et al. "Comparison of different buffers for protein extraction from formalin-fixed and paraffin-embedded tissue specimens." PLoS One 10(11): e0142650 (2015). doi:10.1371/journal.pone.0142650.
Shi, S. R., et al. "Antigen retrieval in formalin-fixed, paraffin-embedded tissues: An enhancement method for immunohistochemical staining based on microwave oven heating of tissue sections." J. Histochem. Cytochem. 39(6):741-8 (1991) doi:10.1177/39.6.1709656.
Tanca, A. et al. "Comparability of differential proteomics data generated from paired archival fresh-frozen and formalin-fixed samples by GeLC-MS/MS and spectral counting." J. Proteomics 77:561-576 (2012). doi:10.1016/j.jprot.2012.09.033.
Tanca, A. et al. "Critical comparison of sample preparation strategies for shotgun proteomic analysis of formalin-fixed, paraffin-embedded samples: Insights from liver tissue." Clin. Proteomics 11:28 (2014). doi:10.1186/1559-0275-11-28.

Testagrossa et al. "Immunohistochemical expression of podocyte markers in the variants of focal segmental glomerulosclerosis." National Dial Transplant 28: 91-98 (2013).
ThermoFisher Scientific, Epitope Recovery Methods for IHC, Nov. 7, 2015, pp. 1-2.
Valenzuela, J. I. et al. "Diversifying the secretory routes in neurons." Frontiers in Neuroscience 9:358 (2015). doi:10.3389/fnins.2015.00358.
Van Meer, G., et al. "Membrane lipids: Where they are and how they behave." Nature Reviews Molecular Cell Biology 9(2): 112-124 (2008). doi:10.1038/nrm2330.
Wassie, A. T., et al. "Expansion microscopy: principles and uses in biological research." Nature Methods 16(1): 33-41 (2019). doi:10.1038/s41592-018-0219-4.
Weber, P. C., et al. "Structural origins of high-affinity biotin binding to streptavidin." Science 243(4887):85-88 (1989). doi:10.1126/science.2911722.
Wen, G. et al. "Evaluation of direct grafting strategies in Expansion Microscopy," BioRxiv preprint Jul. 8, 2019, doi: https://doi.org/10.1101/696039 (Jul. 8, 2019).
Wurm. C. A. et al. "Nanoscale distribution of mitochondrial import receptor Tom20 is adjusted to cellular conditions and exhibits an inner-cellular gradient." Proc. Natl. Acad. Sci. U. S. A. 108(33):13546-13551 (2011). doi:10.1073/pnas.1107553108.
Yan, B. X. et al. "Glycine residues provide flexibility for enzyme active sites." J. Biol. Chem. 272(6): 3190-4 (1997). doi:10.1074/jbc.272.6.3190.
Zhao, Y. et al. "Nanoscale imaging of clinical specimens using pathology-optimized expansion microscopy." Nat. Biotechnol. 35(8): 757-764 (2017). doi:10.1038/nbt.3892.
Zuiderveld, K. "Contrast Limited Adaptive Histogram Equalization." in Graphics Gems 474-485 (1994). doi:10.1016/b978-0-12-336156-1.50061-6.
[Supplementary material] Chen, X et al. AT AC-see reveals the accessible genome by transposase-mediated imaging and sequencing, Nature Methods, vol. 13, No. 12, Oct. 17, 2016, 1813-1828.
Ke, R. et al., Supplementary Material In situ sequencing for RNA analysis in preserved tissue and cells, Nature Methods 10(9):857-60, 2013, 1-29.
Abbasi et al., Palmitic Acid-Modified Poly-L-Lysine for Non-Viral Delivery of Plasmid DNA to Skin Fibroblasts, 2007, Biomacromolecules 2007, 8, 1059-1063 (Year: 2007).
Abcam, "IHC-Paraffin Protocol (IHC-P)", 13 pages, published: Jun. 15, 1999, online webpage: www.abcam.com/ps/pdf/protocols/ihc_p.pdf. (Year: 1999).
Ahearn et al., Posttranslational Modifications of RAS Proteins, Cold Spring Harb Perspect Med 2018;8:a031484 (Year: 2018).
Alon, S. et al. Expansion sequencing: Spatially precise in situ transcriptomics in intact biological systems. Science 371, 481-+, doi:10.1126/science.aax2656 (2021).
Bensimon, A. et al., "Alignment and Sensitive Detection of DNA by a Moving Interface." Alignment and Sensitive Detection of DNA by a Moving Interface.
Cahoon, C. K. et al. Superresolution expansion microscopy reveals the three-dimensional organization of the *Drosophila synaptonemal* complex. Proc Natl Acad Sci U S A 114, E6857-E6866, doi:10.1073/pnas.1705623114 (2017).
Campbell, K. R. et al. clonealign: statistical integration of independent single-cell RNA and DNA sequencing data from human cancers. Genome Biol 20, 54, doi:10.1186/s13059-019-1645-z (2019).
Caprette, "Experimental Biosciences: Resources for Introductory & Intermediate level laboratory courses" (2012), available online at https://www.ruf.rice.edu/~bioslabs/studies/sds-page/denature.html (Year: 2012).
Cheeseman, Kevin, et al. "A Diagnostic Genetic Test for the Physical Mapping of Germline Rearrangements of the Susceptibility Breast Cancer Genes BRCA1 and BRCA2." Human Mutation, vol. 33, No. 6, 998-1009, 2012.
Chen, G. et al. Reactivity of functional groups on the protein surface: development of epoxide probes for protein labeling. J Am Chem Soc 125, 8130-8133, doi:10.1021/ja034287m (2003).
Cho et al., "Expansion Microscopy" (2018), Journal of Microscopy, vol. 271, Issue 2: 123-128. (Year: 2018).

(56) References Cited

OTHER PUBLICATIONS

Cirillo, L. et al. UBAP2L forms distinct cores that act in nucleating stress granules upstream of G3BP1. Curr Biol 30, 698-707 e696, doi:10.1016/j.cub.2019.12.020 (2020).

Cote, A. et al. The spatial distributions of pre-mRNAs suggest post-transcriptional splicing of specific introns within endogenous genes. bioRxiv, doi:10.1101/2020.04.06.028092 (2020).

Cui, Y. et al. Fluctuation localization imaging-based fluorescence in situ hybridization (fliFISH) for accurate detection and counting of RNA copies in single cells. Nucleic Acids Res 46, e7, doi:10.1093/nar/gkx874 (2018).

Cui, Y. et al. Quantitative mapping of oxidative stress response to lithium cobalt oxide nanoparticles in single cells using multiplexed in situ gene expression analysis. Nano Lett 19, 1990-1997, doi:10.1021/acs.nanolett.8b05172 (2019).

Decarreau, J. et al. Corrigendum: The tetrameric kinesin Kif25 suppresses pre-mitotic centrosome separation to establish proper spindle orientation. Nat Cell Biol 19, 740, doi:10.1038/ncb3546 (2017).

Decarreau, J. et al. The tetrameric kinesin Kif25 suppresses pre-mitotic centrosome separation to establish proper spindle orientation. Nat Cell Biol 19, 384-390, doi:10.1038/ncb3486 (2017).

Diggle MA et al., A novel method for preparing single-stranded DNA for pyrosequencing, 2003, Molecular Biotechnology, 24(2) :221-224.

Eirew, P. et al. Dynamics of genomic clones in breast cancer patient xenografts at single-cell resolution. Nature 518, 422-426, doi:10.1038/nature 13952 (2015).

Falahati, H. et al., Thermodynamically driven assemblies and liquid-liquid phase separations in biology. Soft Matter 15, 1135-1154, doi:10.1039/c8sm02285b (2019).

Fecher, C. et al. Cell-type-specific profiling of brain mitochondria reveals functional and molecular diversity. Nat Neurosci 22(10), 1731-1742 doi:10.1038/s41593-019-0479-z (2019).

Gad, Sophie, et al. "Identification of a large rearrangement of the BRCA1 gene using colour bar code on combed DNA in an American breast/ovarian cancer family previously studied by direct sequencing." F. Med Genet 2001, 38:388-392.

Gambarotto, D. et al. Imaging cellular ultrastructures using expansion microscopy (U-ExM). Nat Methods 16, 71-74, doi:10.1038/s41592-018-0238-1 (2019).

Gao, M. et al. Expansion stimulated emission depletion microscopy (ExSTED). ACS Nano 12, 4178-4185, doi:10.1021/acsnano.8b00776 (2018).

Gao, R. et al. A highly homogeneous polymer composed of tetrahedron-like monomers for high-isotropy expansion microscopy. Nat Nanotechnol 16, 698-707, doi:10.1038/s41565-021-00875-7 (2021).

Gao, R. et al. Cortical column and whole-brain imaging with molecular contrast and nanoscale resolution. Science 363(6424), doi:10.1126/science.aau8302 (2019).

Guan et al., Understanding Protein Palmitoylation: Biological Significance and Enzymology, 2011, Sci China Chem. Dec. 2011; 54(12): 1888-1897 (Year: 2011).

Hafner, A. S. et al., Local protein synthesis is a ubiquitous feature of neuronal pre- and postsynaptic compartments. Science 364, doi:10.1126/science.aau3644 (2019).

Halpern, A. R. et al., Hybrid structured illumination expansion microscopy reveals microbial cytoskeleton organization. ACS Nano 11, 12677-12686, doi:10.1021/acsnano.7b07200 (2017).

Hamano et al., ε-Poly-L-Lysine Peptide Chain Length Regulated by the Linkers Connecting the Transmembrane Domains of £-Poly-L-Lysine Synthetase, Aug. 2014, Applied and Environmental Microbiology, vol. 80 No. 16, p. 4993-5000 (Year: 2014).

Hansen, M., et al. Molecular details of the structure of a psorospermin-DNA covalent/intercalation complex and associated DNA sequence selectivity. J Am Chem Soc 118, 5553-5561 (1996).

He, J. et al. Prevalent presence of periodic actin-spectrin-based membrane skeleton in a broad range of neuronal cell types and animal species. Proc Natl Acad Sci U S A 113, 6029-6034, doi:10.1073/pnas.1605707113 (2016).

Hodson, Robert E. et al. "In Situ PCR for Visualization of Microscale Distribution of Specific Genes and Gene Products in Prokaryotic Communities." Applied and Environmental Microbiology, Nov. 1995, p. 4074-4082.

Invitrogen Corporation, "Proteinase K (solution), RNA Grade", Cat. No. 25530-049, rev. date: Aug. 25, 2008, 2 pages, accessed from https://www.thermofisher.com/document-connect/document-connect.html?url=https://assets.thermofisher.com/TFS-Assets%2FLSG%2Fmanuals%2Fproteinasek_solution_man.pdf (2008).

Jain, Miten et al. "Nanopore sequencing and assembly of a human genome with ultra-long reads." Nature Biotechnology, vol. 36, No. 4, Apr. 2018.

Kao, P. et al., Transcriptional activation of *Arabidopsis zygotes* is required for initial cell divisions. Sci Rep 9, 17159, doi:10.1038/s41598-019-53704-2 (2019).

Karagiannis, E. D. et al. Expansion microscopy of lipid membranes. bioRxiv, 829903, doi:10.1101/829903 (2019).

Kaykov, A., et al. "Molecular Combing of Single DNA Molecules on the 10 Megabase Scale." Sci. Rep. 6, 19636, 2016, p. 1-9.

Kleuss et al., Galphas is palmitoylated at the N-terminal glycine, The EMBO Journal vol. 22 No. 4 pp. 826-832, 2003 (Year: 2003).

Kondo, N. et al. "DNA Damage Induced by Alkylating Agents and Repair Pathways." Journal of Nucleic Acids, vol. 2010, Article ID 543531, 7 pages.

Koppers, M. et al. Receptor-specific interactome as a hub for rapid cue-induced selective translation in axons. Elife 8, 1-27 doi:10.7554/eLife.48718 (2019).

Kumar, A. et al. Influenza virus exploits tunneling nanotubes for cell-to-cell spread. Sci Rep 7, 1-14, 40360, doi:10.1038/srep40360 (2017).

Kunz, T. C. et al., Using Expansion Microscopy to Visualize and Characterize the Morphology of Mitochondrial Cristae. Front Cell Dev Biol 8, 617, doi:10.3389/fcell.2020.00617 (2020).

Larsson, Chatarina et al. "In situ genotyping individual DNA molecules by target-primed rolling-circle amplification of padlock probes." Nature Methods, vol. 1, No. 3, Dec. 2004.

Li, R. et al., Expansion enhanced nanoscopy. Nanoscale 10, 17552-17556, doi:10.1039/c8nr04267e (2018).

Lim, Y. et al. Mechanically resolved imaging of bacteria using expansion microscopy. PLoS Biol 17, e3000268, doi:10.1371/journal.pbio.3000268 (2019).

Marie, R., et al. "Concentrating and labeling genomic DNA in a nanofluidic array." Nanoscale. 10 (2018), pp. 1376-1382.

Martinez, G. F. et al. Quantitative expansion microscopy for the characterization of the spectrin periodic skeleton of axons using fluorescence microscopy. Sci Rep 10, 2917, doi:10.1038/s41598-020-59856-w (2020).

Maxam, A. M., and Gilbert W., "A new method for sequencing DNA." Proc. Natl. Acad. Sci. U.S.A., 74, 560-564, 1977.

Mosca, T. J. et al., Presynaptic LRP4 promotes synapse number and function of excitatory CNS neurons. Elife 6, doi:10.7554/eLife.27347 (2017).

M'Saad, O. et al., Light microscopy of proteins in their ultrastructural context. Nat Commun 11, 3850, doi:10.1038/s41467-020-17523-8 (2020).

Nyren, Pal, et al. "Solid Phase DNA Minisequencing by an Enzymatic Luminometric Inorganic Pyrophosphate Detection Assay." Analytical Biochemistry 208, 171-175 (1993).

Park, Y. G. et al. Protection of tissue physicochemical properties using polyfunctional crosslinkers. Nat Biotechnol 37, 73-83, doi:10.1038/nbt.4281 (2019).

Richter, S. et al. Clerocidin alkylates DNA through its epoxide function: evidence for a fine tuned mechanism of action. Nucleic Acids Res 31, 5149-5156, doi:10.1093/nar/gkg696 (2003).

Sahl, S. J. et al., Fluorescence nanoscopy in cell biology. Nat Rev Mol Cell Biol 18(11), 685-701, doi:10.1038/nrm.2017.71 (2017).

Salaun et al., The intracellular dynamic of protein palmitoylation, 2010, J. Cell Biol. vol. 191 No. 7 1229-1238 (Year: 2010).

Sarkar, D. et al. Expansion revealing: decrowding proteins to unmask invisible brain nanostructures. bioRxiv, doi:10.1101/2020.08.29.273540 (2020).

(56) References Cited

OTHER PUBLICATIONS

Schirmer, M., et al. "Insight into biases and sequencing errors for amplicon sequencing with the Illumina MiSeq platform." Nucleic Acids Research, vol. 43, Issue 6, Mar. 31, 2015, e37, pp. 1-16.
Schonhuber, Wilhelm, et al. "Improved Sensitivity of Whole-Cell Hybridization by the Combination of Horseradish Peroxidase-Labeled Oligonucleotides and Tyramide Signal Amplification." Applied and Environmental Microbiology, Aug. 1997, p. 3268-3273.
Shen, F. Y et al. Light microscopy based approach for mapping connectivity with molecular specificity. Nat Commun 11, 4632, doi:10.1038/s41467-020-18422-8 (2020).
Shendure, J., et al. "DNA sequencing at 40: past, present, and future." Nature 2017, Oct. 19;550(7676): 345-353.
Shurer, C. R. et al. Physical principles of membrane shape regulation by the glycocalyx. Cell 177, 1757-1770 e1721, doi:10.1016/j.cell.2019.04.017 (2019).
Sidenstein, S. C. et al. Multicolour multilevel STED nanoscopy of actin/spectrin organization at synapses. Sci Rep 6, 26725, doi:10.1038/srep26725 (2016).
So, C. et al. A liquid-like spindle domain promotes acentrosomal spindle assembly in mammalian oocytes. Science 364, doi:10.1126/science.aat9557 (2019).
Stankova, Helena, et al. "BioNano genome mapping of individual chromosomes supports physical mapping and sequence assembly in complex plant genomes." Plant Biotechnology Journal (2016) 14, pp. 1523-1531 doi: 10.1111/pbi.12513.
Strick, T., et al. "Twisting and stretching single DNA molecules." Progress in Biophysics & Molecular Biology 74 (2000) 115-140.
Suofu, Y. et al. Dual role of mitochondria in producing melatonin and driving GPCR signaling to block cytochrome c release. Proc Natl Acad Sci U S A 114, E7997-E8006, doi:10.1073/pnas.1705768114 (2017).
Thevathasan, J. V. et al. Nuclear pores as versatile reference standards for quantitative superresolution microscopy. Nat Methods 16, 1045-1053, doi:10.1038/s41592-019-0574-9 (2019).
Tillberg, P. W. et al. Expansion microscopy: scalable and convenient super-resolution microscopy. Annu Rev Cell Dev Biol 35, 683-701, doi:10.1146/annurev-cellbio-100818-125320 (2019).
Truckenbrodt et al., A practical guide to optimization in X10 expansion microscopy. Nat Protoc 14, 832-863, doi:10.1038/s41596-018-0117-3 (2019).
Ueda. H.R., et al. "Tissue clearing and its applications in neuroscience." Nature Reviewss, Neuroscience, vol. 21, Feb. 2020.
Valdes, P. A. et al. Decrowding expansion pathology: unmasking previously invisible nanostructures and cells in intact human brain pathology specimens. bioRxiv, doi:10.1101/2021.12.05.471271 (2021).
Varapula et al., A micropatterned substrate for on-surface enzymatic labelling of linearized long DNA molecules, 2019, Scientific Reports, 9, 15059.
Wages JM, Polymerase Chain Reaction, 2005, Encyclopedia of Analytical Science, (2): 243-250.
Wang, G. et al., Multiplexed imaging of high-density libraries of RNAs with MERFISH and expansion microscopy. Sci Rep 8(4847), 1-13 doi:10.1038/s41598-018-22297-7 (2018).
Wang, X., et al., "Characterization of denaturation and renaturation of DNA for DNA hybridization." Environ. Health Toxicol, 29, e2014007, 2014.
Wang, Y. et al. EASI-FISH for thick tissue defines lateral hypothalamus spatio-molecular organization. Cell 184, 6361-6377 e6324, doi:10.1016/j.cell.2021.11.024 (2021).
Wen et al., Specific antibody immobilization with biotin-poly(L-lysine)-g-poly(ethylene glycol) and protein A on microfluidic chips, Journal of Immunological Methods 350 (2009) 97-105 (Year: 2009).
Xu, H. et al. Molecular organization of mammalian meiotic chromosome axis revealed by expansion STORM microscopy. Proc Natl Acad Sci U S A 116, 18423-18428, doi:10.1073/pnas.1902440116 (2019).
Xu, K. et al., Actin, spectrin, and associated proteins form a periodic cytoskeletal structure in axons. Science 339, 452-456, doi:10.1126/science.1232251 (2013).
Dong, Huimin et al. "Preparation of photodeformable azobenzene polymer fibers by post-crosslinking strategy: Understanding the structure-property relationship", European Polymer Journal, Pergamon Pressltd Oxford, GB, vol. 135, Jul. 10, 2020 (Jul. 10, 2020), XP086242455, ISSN: 0014-3057, DOI:10.1016/J.EURPOLYMJ.2020.109863.
Lunzer, Markus et al. "A Modular Approach to Sensitized Two-Photon Patterning of Photodegradable Hydrogels", Angewandte Chemie, Wiley-V CH Verlaggmbh & Co. KGAA, DE, vol. 130, No. 46, (Oct. 18, 2018), pp. 15342-15347, XP071375228, ISSN: 0044-8249, DOI:10.1002/ANGE.201808908.
Rapp, Teresa et al. "Visible Light-Responsive Dynamic Biomaterials: Going Deeper and Triggering More", Advanced Healthcare Materials, Wiley-V CH Verlag GMBH & CO. KGAA, DE, vol. 9, No. 7, Feb. 25, 2020, page n/a, XP072463096, ISSN: 2192-2640, DOI:10.1002/ADHM.201901553.
Sikdar, Partha et al. "Recent advances in the synthesis of smart hydrogels", Materials Advances, vol. 2, No. 14, Jan. 1, 2021, pp. 4532-4573, XP093067739, DOI: 10.1039/D1MA00193K.
Singh, Anirudha et al. "Photomodulation of Cellular Gene Expression in Hydrogels", ACS Macro Letters, vol. 2, No. 3, (Mar. 8, 2013), pp. 269-272, XP093109803, ISSN: 2161-1653, DOI: 10.1021/mz300059lm.
Yanagawa, Fumiki et al. "Activated-Ester-Type Photocleavable Crosslinker for Preparation of Photodegradable Hydrogels Using a Two-Component Mixing Reaction", Advanced Healthcare Materials, Wiley-V CH Verlag GMBH & CO. KGAA, DE, vol. 4, No. 2, (Aug. 13, 2014), pp. 246-254, XP072465709, ISSN: 2192-2640, DOI:10.1002/ADHM.201400180.

\* cited by examiner

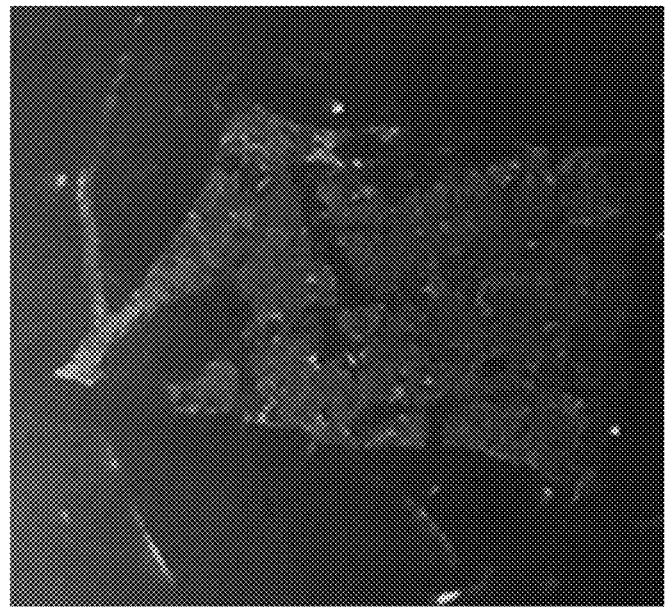
FIG. 3Ai
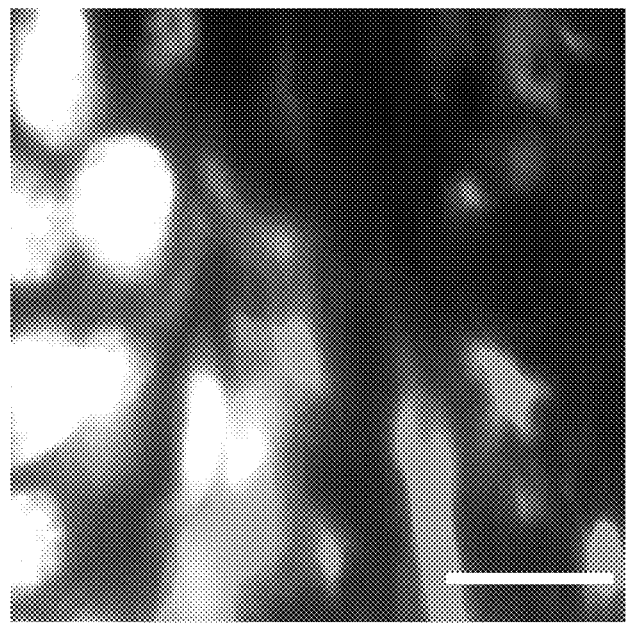
FIG. 3Aii

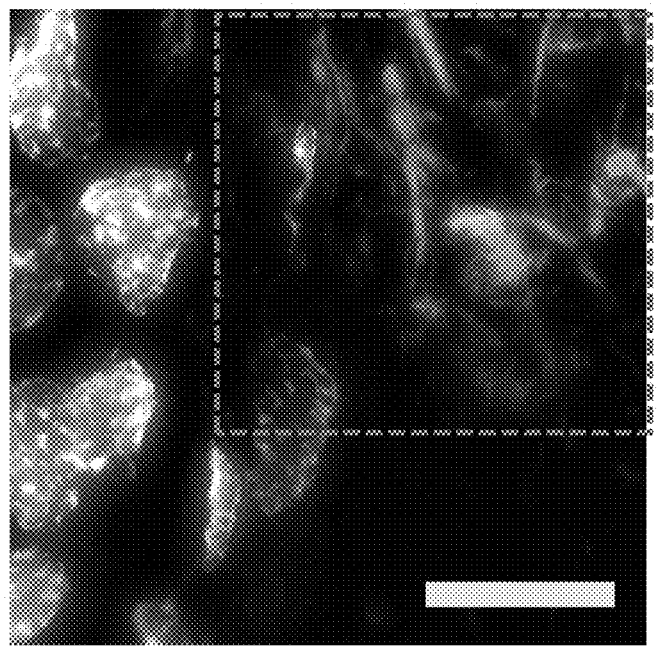
FIG. 3Aiii
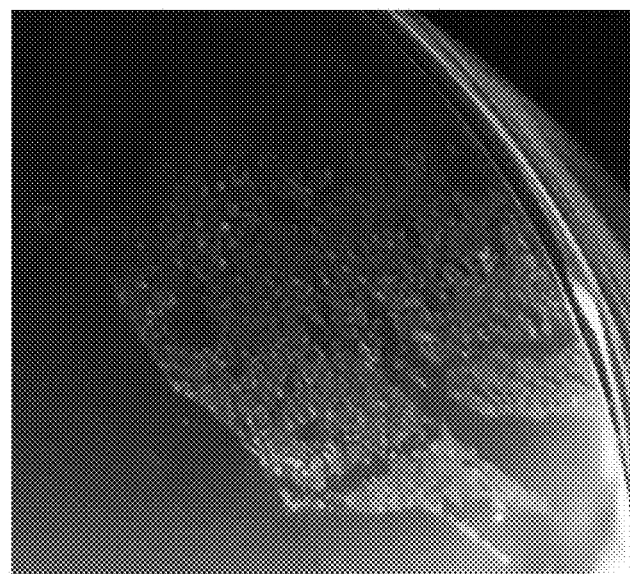
FIG. 3Aiv

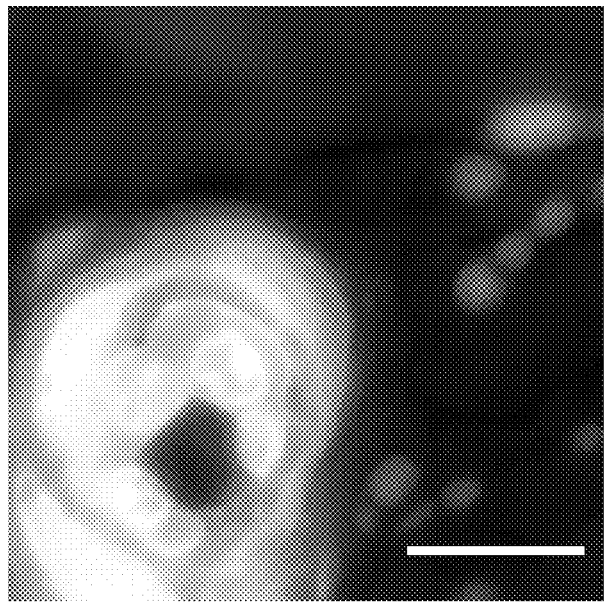
FIG. 3Av
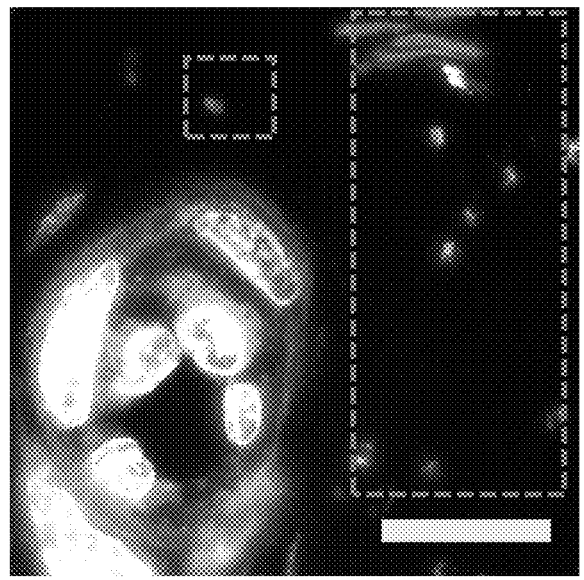
FIG. 3Avi

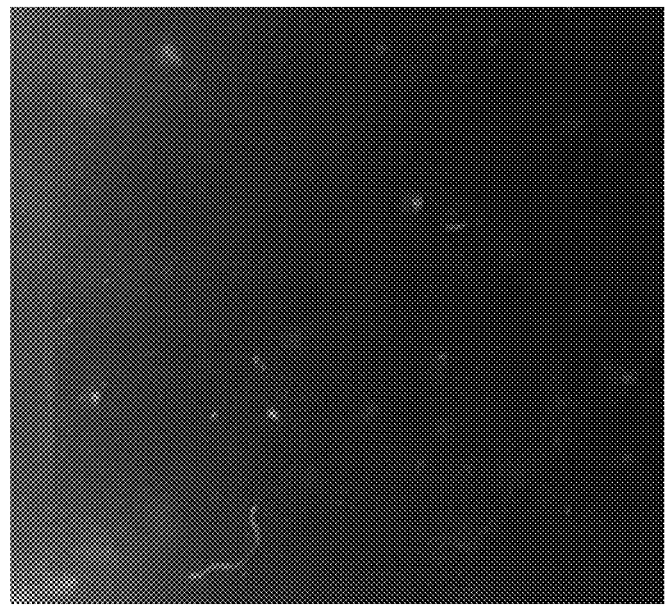
FIG. 3Bi
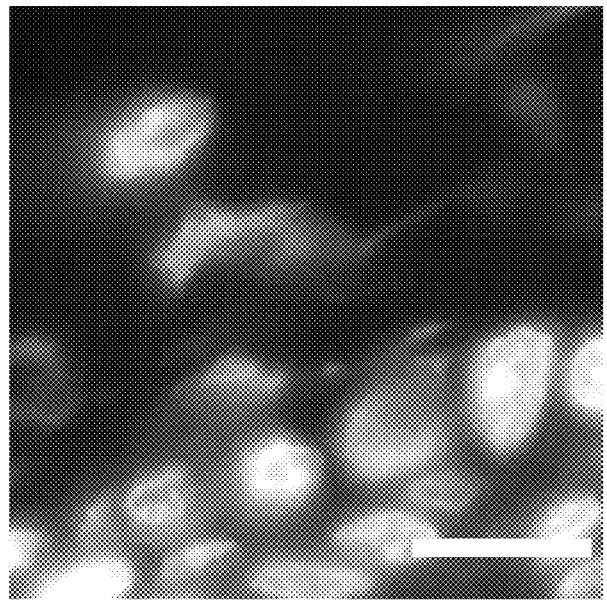
FIG. 3Bii

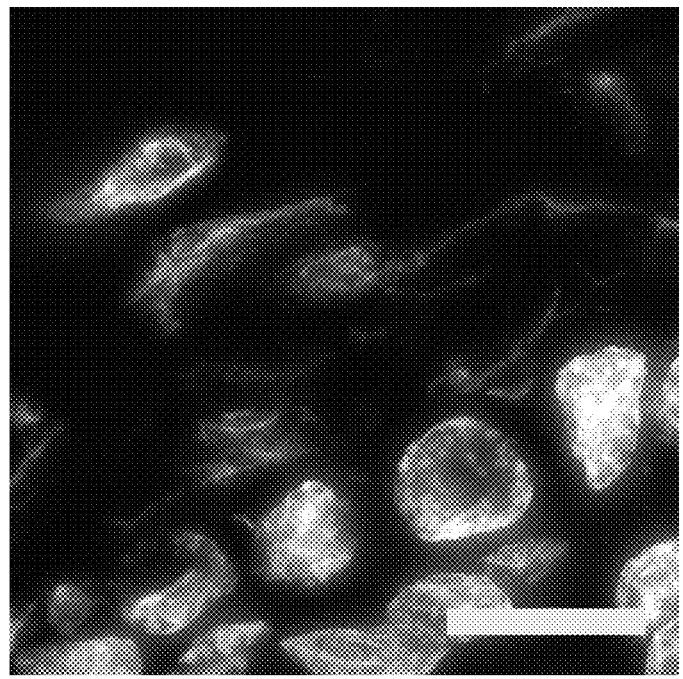
FIG. 3Biii
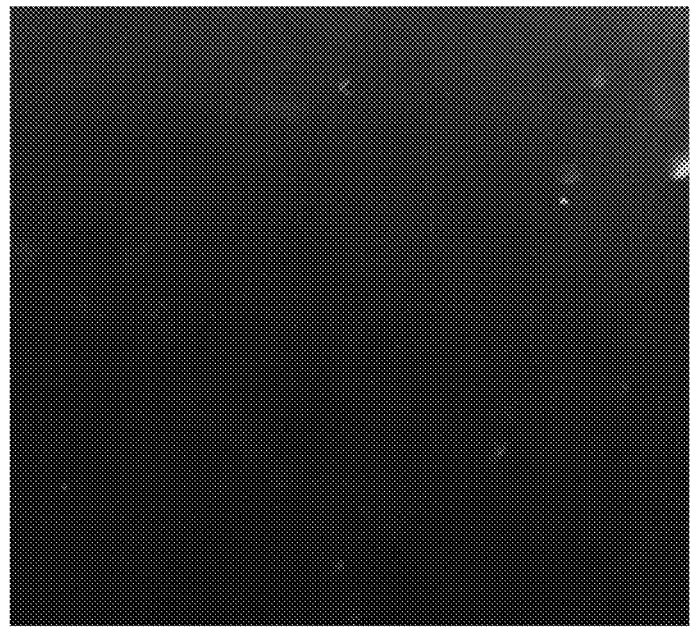
FIG. 3Biv

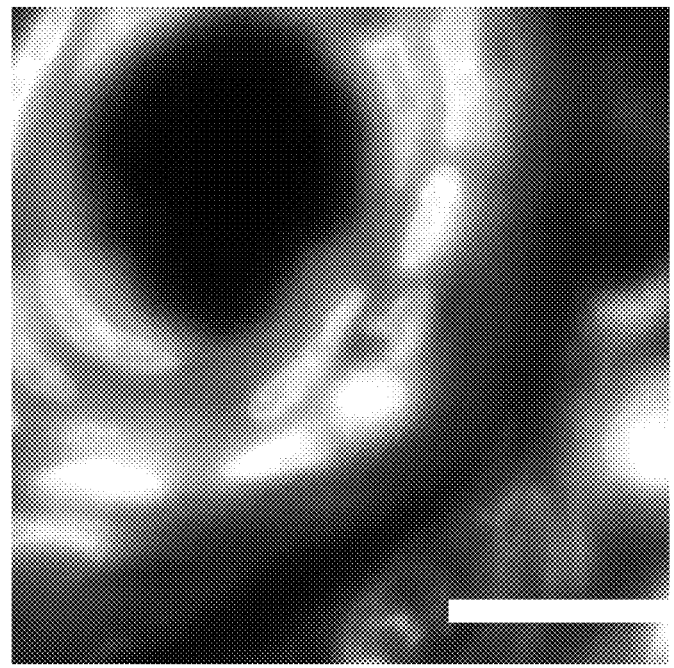
FIG. 3Bv
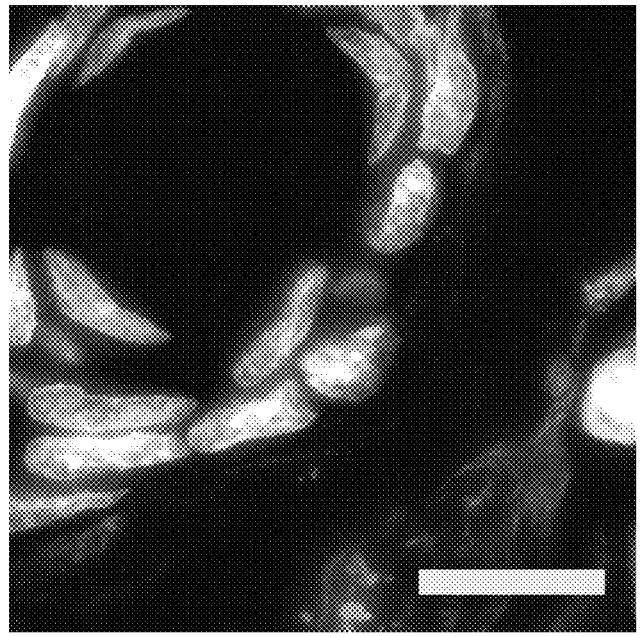
FIG. 3Bvi

METHODS FOR DIAGNOSING NEOPLASTIC LESIONS

RELATED APPLICATIONS

This application is a continuation of International Application No. PCT/US18/19756, which designated the United States and was filed on Feb. 26, 2018, published in English, which claims the benefit of U.S. Provisional Application Ser. No. 62/463,265, filed on Feb. 24, 2017, the contents of which are incorporated herein by reference in its entirety.

BACKGROUND

In pathology, examination of cellular structures and molecular composition using diffraction-limited microscopy has long been key to the diagnosis of a wide variety of pre-disease and disease states. Biomolecules themselves, however, are nanoscale in dimension and configured with nanoscale precision throughout cells and tissues. In basic science, this has begun to be explored using pioneering super-resolution microscopy methods, as well as electron microscopy methods, but such strategies require complex hardware, can present a steep learning curve, and are difficult to apply to large-scale samples such as human tissues. Accordingly, super-resolution imaging and nanoscopy have not found routine utility in the clinical practice of pathology.

Thus, there is a need for higher resolution microscopy that can work with current diffraction limited microscopes and can optically magnify samples, such as tissue sections or tumors, with nanoscale precision.

SUMMARY OF THE INVENTION

The invention provides a method for preparing an expanded biological specimen. The expanded biological specimen is suitable for microscopic analysis. By "microscopic analysis" it is meant the analysis of a specimen using any technique that provides for the visualization of aspects of a specimen that cannot be seen with the unaided eye, i.e., that are not within the resolution range of the normal eye. By "preparing an expanded biological specimen" it is generally meant that the biological specimen is physically expanded, or enlarged, relative to the specimen prior to be exposed to the method(s) described herein. Expanding the biological sample can be achieved by binding, e.g., anchoring, key biomolecules to a polymer network and swelling, or expanding, the polymer network, thereby moving the biomolecules apart as further described below. As the biomolecules are anchored to the polymer network isotropic expansion of the polymer network retains the spatial orientation of the biomolecules resulting in an expanded, or enlarged, biological specimen.

A method for diagnosing neoplastic lesions in an expanded biological tissue sample of a patient comprising providing at least one sample image of the expanded biological tissue sample; providing a computer configured to analyze the sample; analyzing, with the computer, the sample, detecting and segmenting nuclei; calculating, with the computer, molecular characteristics of those nuclei; and determining, with the computer, a diagnosis of the sample by comparing the sample with a benign normal tissue reference. In some embodiments, the diagnosis of the neoplastic lesion may include cancer, malignant tumor or pre-malignant pathology diagnosis.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale emphasis instead being placed upon illustrating the principles of the invention.

DETAILED DESCRIPTION

Figure 1A:
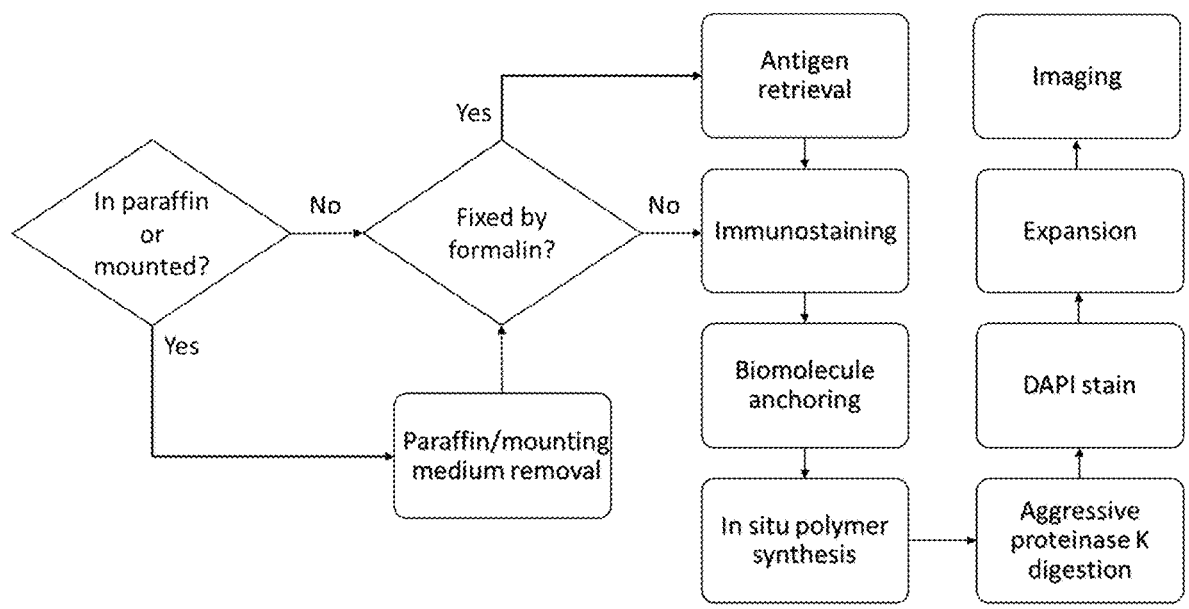
FIG. 1A through FIG. 1M depict the design and validation of expansion pathology (ExPath). (A) Schematic of ExPath workflow. (B) Pre-expansion image of a 1.5 mm core of normal human breast tissue acquired with a widefield epifluorescent microscope, and stained with DAPI as well as multiple antibodies. Blue, DAPI; green, vimentin; red, voltage-dependent anion channel (VDAC). (C) ExPath image of the sample of B, on the same scope. (D and E) Root mean square (RMS) length measurement error as a function of measurement length for pre-vs post-expansion images (blue solid line, mean of DAPI channel; green solid line, mean of vimentin channel; shaded area, standard error of mean; n=3 different patients. Average expansion factor: 4.3 (SD: 0.3)). (F) Super-resolution structured illumination microscopy (SR-SIM) image of normal human breast tissue, stained with DAPI and multiple antibodies. Blue, DAPI; green, vimentin; red, keratin-19 (KRT19). (G) ExPath image of the sample of F acquired with a spinning disk confocal microscope. (H and I) RMS length measurement error as a function of measurement length for ExPath vs SIM images of human breast tissue (blue solid line, mean of DAPI channel; red solid line, mean of KRT19 channel; shaded area, standard error of mean; n=5 fields of view from samples from 4 different patients. Average expansion factor: 4.0 (SD:0.2)). (J) Hematoxylin and eosin (H&E) stained human breast sample with atypical ductal hyperplasia (ADH). Inset (upper left) is a magnified view of the area framed by the dotted line. (K) ExPath widefield fluorescent image of the sample of J, stained with antibodies against Hsp60 (red) vimentin (green), and DAPI (blue). (L) ExPath widefield fluorescent image of a human breast sample without HER2 amplification. Blue, anti-HER2 (not visible); gray, DAPI; green, DNA FISH against chromosome 17 centrosome; red, DNA FISH against HER2. (M) ExPath widefield fluorescent image of a human breast cancer sample with HER2 amplification, stained as in L. Scale bars: (B) 200 µm, (C) 220 µm (physical size post-expansion, 900 µm; expansion factor 4.1), (F) 10 µm, (G) 10 µm (physical size post-expansion, 43 µm, expansion factor 4.3). (J) 5 µm; inset 1 µm (K) 5 µm; inset 1 µm (physical size post-expansion, 23 µm; inset, 4.6 µm; expansion factor 4.6). (L) and (M), physical size post-expansion 20 µm.
Figure 1B:
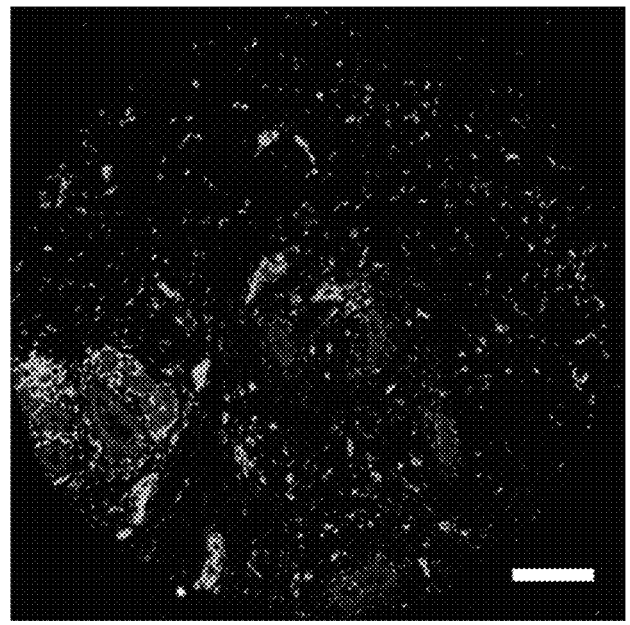
Figure 1C:
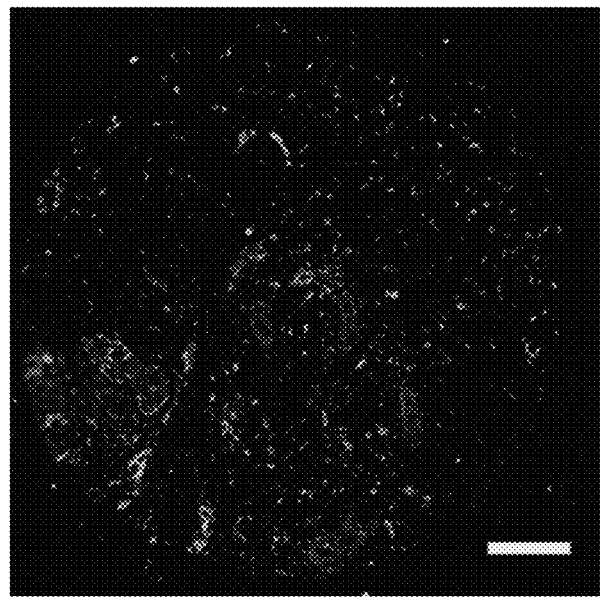
Figure 1D:
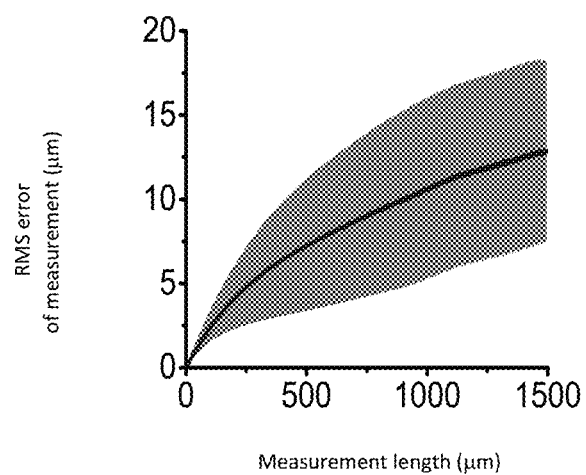
Figure 1E:
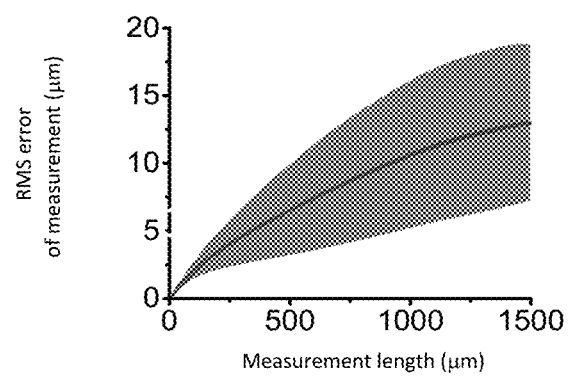
Figure 1F:
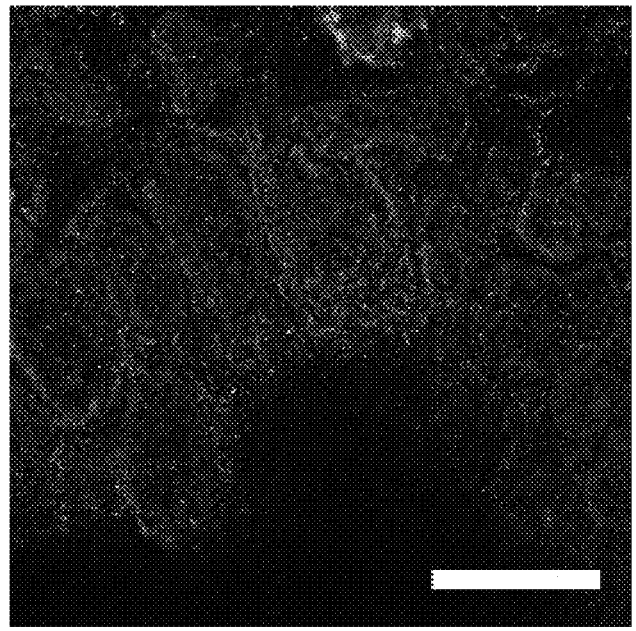
Figure 1G:
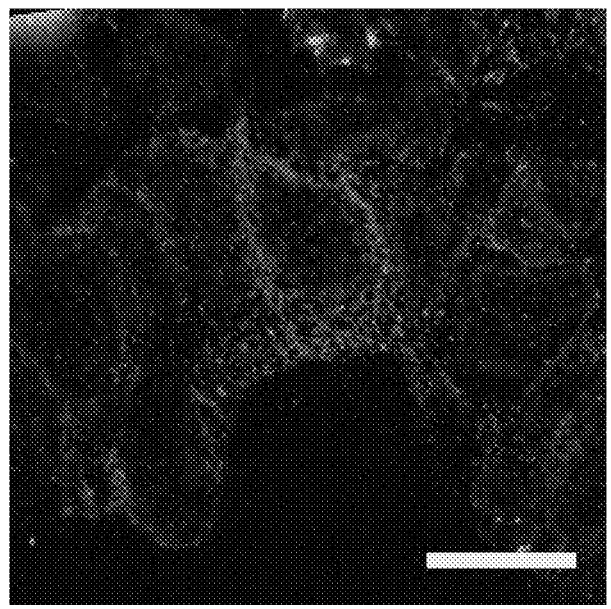
Figure 1H:
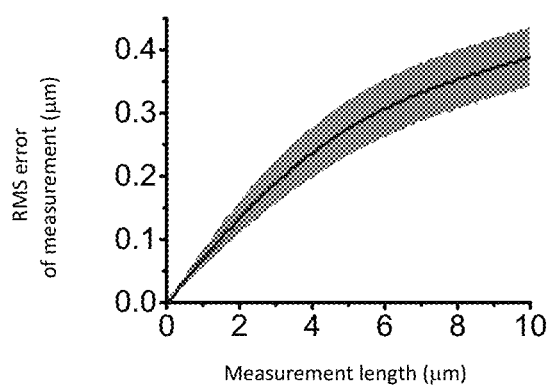
Figure 1I:
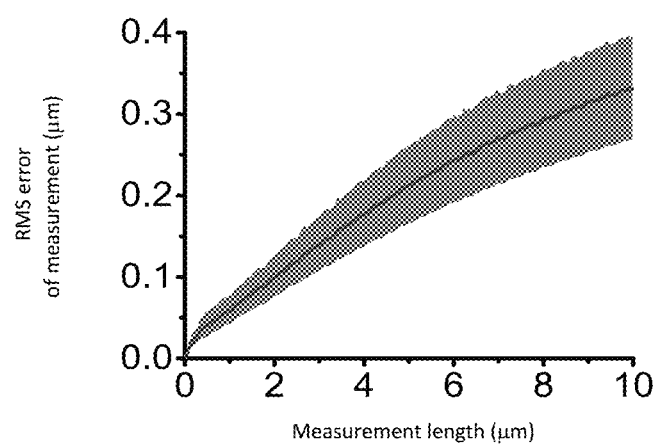

Method and compositions are provided for imaging cell and tissue samples by physically, rather than optically, magnifying them. International patent application serial number PCT/US15/16788, filed on Feb. 20, 2015, which is incorporated herein by reference, teaches that the resolution of conventional optical microscopy can be increased 4-5 fold by physically expanding specimens, a processed termed 'expansion microscopy' (ExM). Briefly, biological specimens are embedded in a swellable hydrogel material, subjected to a treatment to disrupt native biological networks, and then expanded. The advantages of ExM include tissue clearing, resolution improvement, and higher tolerance to sectioning error due to the specimen expansion in the z-axis. However, the ExM process was limited in the increased fold of physical expansion and in that the degree of expansion of one sample to the next was inconsistent.

The invention provides expansion pathology method (ExPath), a simple and versatile method for optical interrogation of clinical biopsy samples with nanoscale precision and molecular identity. ExPath is capable of processing the majority of clinical samples currently used in pathology including formalin-fixed paraffin-embedded (FFPE), hematoxylin and eosin (H&E)-stained, and/or fresh frozen tissue specimens and thus enables nanoscale imaging without the need for hardware beyond that found in conventional laboratories. ExPath functions well on a wide diversity of tissue types, and has immediate clinical application in the diagnosis of diseases known to exhibit nanoscale pathology.

As used herein and in the appended claims, the singular forms "a", "an", and "the" are defined to mean "one or more" and include the plural unless the context clearly dictates otherwise.

It is further noted that the claims can be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which can be readily separated from or combined with the features of any of the other several embodiments without departing from the scope or spirit of the present teachings. Any recited method can be carried out in the order of events recited or in any other order which is logically possible.

The invention provides a method for diagnosing neoplastic lesions in an expanded biological tissue sample of a patient comprising providing at least one sample image of the expanded biological tissue sample; providing a computer configured to analyze the sample; analyzing, with the computer, the sample detect and segment nuclei; calculating, with the computer, molecular characteristics of those nuclei; and determining, with the computer, a diagnosis of the sample by comparing the sample with a normal tissue reference.

The word neoplasm, meaning "new growth" in Greek, refers to any abnormal growth, whether malignant or benign. Neoplasms, neoplastic lesions and neoplastic disease may be used interchangeably herein and generally refer to both malignant and benign growths. Neoplasms can be benign, potentially malignant, or malignant and are commonly categorized into four main groups: benign neoplasms, in situ neoplasms, malignant neoplasms, and neoplasms of uncertain or unknown behavior or origin. Benign neoplasms include uterine fibroids and melanocytic nevi (skin moles). They are circumscribed and localized and often do not transform into cancer. Potentially-malignant neoplasms include carcinoma in situ. They are localised, do not invade and destroy but in time, may transform into a cancer. Malignant neoplasms are also simply known as cancers and are the focus of oncology. They invade and destroy the surrounding tissue, may form metastases and, if untreated or unresponsive to treatment, will prove fatal. Rarely there can be a metastatic neoplasm with no known site of the primary cancer and this is classed as a cancer of unknown primary origin. The invention provides a method for diagnosing cancer in an expanded biological tissue sample of a patient comprising providing at least one sample image of the expanded biological tissue sample; providing a computer configured to analyze the sample; analyzing, with the computer, the sample detect and segment nuclei; calculating, with the computer, molecular characteristics of those nuclei; and determining, with the computer, a diagnosis of cancer of the sample by comparing the sample with a normal tissue reference.

The invention provides a method for diagnosis of breast neoplastic lesions by integrating expansion pathology (Ex-Path) with computational image analysis.

In one embodiment, the invention provides a computer-implemented method for diagnosis of breast neoplastic lesions, the method comprising providing a system comprising a computer information pertaining to at least one image of an expanded tissue sample; evaluating, using the computer, at least one image and detecting and segmenting nuclei by applying a segmentation analysis to the sample image; evaluating, using the processor, the information of the previous step with an algorithm configured as code executing in the computer, where the algorithm configures the processor to output quantitative values corresponding to molecular characteristics of those nuclei. This method may provide a risk score for cancer occurrence. This method may provide a diagnosis of the sample. The method may further comprise the step of generating, using the computer, a report based on the risk of cancer occurrence assigned to the patient and/or a diagnosis of cancer or precancerous lesions in the patient, which can be further used to guide clinical management, for research purposes or other applications.

In one embodiment the invention provides a method for diagnosing breast cancer in a patient, the method comprising: capturing, with an imaging device, at least one sample image of an expanded tissue sample; accessing from a database, using a processor configured by code executing therein, a patient dataset containing clinical/morphological feature data for the patient corresponding to breast cancer; evaluating, using the processor, at least one sample image recorded by the imaging device and deriving: a) molecular feature values indicative of phenotypic information of molecular regions of tissue by applying first detection and segmentation and these regions and then computing phenotypic characteristics in the sample image; and b) a plurality of morphometric measurements; updating the patient dataset using the processor, by associating with each patient dataset the derived molecular feature values and morphometric measurements; evaluating, using the processor, the updated patient dataset of the previous step with an algorithm configured as code executing in the processor, where the algorithm configures the processor to output values corresponding to diagnoses of the sample. In one embodiment the method further includes generating, using the processor, a report based on the diagnosis of cancer in the patient.

Nuclei and molecular level characteristics are used in diagnosing and grading neoplasms for all body tissues or organs. These characteristics are phenotypical information that include morphological and texture appearances like size, shape, texture, and intensity distribution in these nuclei regions. Physical expansion of the sample provides improved performance in nuclear detection, segmentation and in gaining additional optical resolving power for differentiation of ultrafine structures of individual nuclei that are otherwise beyond optical diffraction limits. This results in high-fidelity discrimination between early breast neoplastic lesions that to date have challenged diagnosis. In some embodiments, nuclear morphology is analyzed and used to classify the neoplastic lesions after DAPI staining of the nuclei and physical expansion of the stained samples.

The computer is configured with a classification system which selects discriminative features and classifies the expanded images into different classes and/or grades of neoplasms. Such a system can be adopted with different types of neoplasms and organs as a large pool of pathological tissue features and/or characteristics that can be selected and interrogated, which are helpful in classifying tissues and grades. The classification system can select the characteristics that are appropriate in the classification of a particular tumor or cancer.

In one embodiment, this classification system may be used in the diagnosis of breast neoplastic lesions to classify the tissue sample normal, benign, pre-invasive or invasive breast lesions.

In some embodiments, the imaging device includes, but is not limited to, a microscope or a pathology slide scanner.

The expanded biological specimen is suitable for microscopic analysis. By "microscopic analysis" it is meant the analysis of a specimen using any technique that provides for the visualization of aspects of a specimen that cannot be seen with the unaided eye, i.e., that are not within the resolution range of the normal eye. By "preparing an expanded biological specimen" it is generally meant that the biological specimen is physically expanded, or enlarged, relative to the specimen prior to be exposed to the method(s) described herein. Expanding the biological sample can be achieved by binding, e.g., anchoring, key biomolecules to a polymer network and swelling, or expanding, the polymer network, thereby moving the biomolecules apart as further described below. As the biomolecules are anchored to the polymer network isotropic expansion of the polymer network retains the spatial orientation of the biomolecules resulting in an expanded, or enlarged, biological specimen.

In one embodiment, the expandable biological specimen may be prepared as follows. A sample is contacted with macromolecules that will bind to biomolecules within the sample. The sample is then treated with a bifunctional crosslinker. The sample is then permeated with precursors of a swellable polymer. The precursors of the swellable polymer are polymerized to form a swellable polymer within the specimen. The biomolecules are anchored to the swellable polymer. The sample may be incubated with a non-specific protease in a buffer comprising a metal ion chelator, a non-ionic surfactant, and a monovalent salt. The expandable biological specimen may be expanded by contacting the swellable polymer with a solvent or liquid to cause the swellable polymer to swell.

In one embodiment, prior to the contacting step, the sample is subjected to any suitable antigen retrieval process known to one of skill in the art and as further described below.

In one embodiment, the method comprises incubating the sample with 1-100 U/ml of a non-specific protease in a buffer having a pH between about 4 and about 12, the buffer comprising about 5 mM to about 100 mM metal ion chelator, about 0.1% to about 1.0% non-ionic surfactant, and about 0.05 M to about 1 M monovalent salt. In one embodiment, the sample is incubated for about 0.5 to about 3 hours at about 50° C. to about 70° C.

In one embodiment, the expandable biological specimen may be prepared as follows. The specimen is treated with a bifunctional crosslinker. The sample is then permeated with precursors of a swellable polymer. The precursors of the swellable polymer are polymerized to form a swellable polymer within the specimen. The specimen may be incubated with a non-specific protease in a buffer comprising a metal ion chelator, a nonionic surfactant, and a monovalent salt.

In one embodiment, the method can further comprise the step of contacting the sample with macromolecules that will bind to biomolecules within the sample. In one embodiment, the method can further comprise the step anchoring the biomolecules to the swellable polymer.

The expandable specimen can be expanded by contacting the swellable polymer with a solvent or liquid to cause the swellable polymer to swell.

In one embodiment, prior to the treating step, the sample is subjected to any suitable antigen retrieval process known to one of skill in the art and as further described below.

In one embodiment, the method comprises incubating the sample with 1-100 U/ml of a non-specific protease in a buffer having a pH between about 4 and about 12, the buffer comprising about 5 mM to about 100 mM metal ion chelator, about 0.1% to about 1.0% non-ionic surfactant, and about 0.05 M to about 1 M monovalent salt. In one embodiment, the sample is incubated for about 0.5 to about 3 hours at about 50° C. to about 70° C.

The terms "biological specimen" or "biological sample" is used interchangeably herein in a broad sense and is intended to include sources that contain nucleic acids and can be fixed. Exemplary biological samples include, but are not limited to tissues, including but not limited to, liver, spleen, kidney, lung, intestine, thymus, colon, tonsil, testis, skin, brain, heart, muscle and pancreas tissue. Other exemplary biological samples include, but are not limited to, biopsies, bone marrow samples, organ samples, skin fragments and organisms. Materials obtained from clinical or forensic settings are also within the intended meaning of the term biological sample. In one embodiment, the sample is derived from a human, animal or plant. In one embodiment, the biological sample is a tissue sample, preferably an organ tissue sample. In one embodiment, samples are human. The sample can be obtained, for example, from autopsy, biopsy or from surgery. It can be a solid tissue such as, for example, parenchyme, connective or fatty tissue, heart or skeletal muscle, smooth muscle, skin, brain, nerve, kidney, liver, pancreas, spleen, stomach, intestine, colon, breast, cartilage, placenta, prostate, thymus, tonsil, umbilical cord, ovary, uterus, carcinoma (e.g. bowel, nasopharynx, breast, lung, stomach etc.), lymphoma, meningioma. The tissue can be a tumor (benign or malignant), cancerous or precancerous tissue. The sample can be obtained from an animal or human subject affected by disease or other pathology or suspected of same (normal or diseased), or considered normal or healthy. As used herein, the term "fixed biological sample", explicitly excludes cell-free samples, for example cell extracts, wherein cytoplasmic and/or nuclear components from cells are isolated.

Tissue specimens suitable for use with the methods and systems described herein generally include any type of tissue specimens collected from living or dead subjects, such as, e.g., biopsy specimens and autopsy specimens. Tissue specimens may be collected and processed using the methods and systems described herein and subjected to microscopic analysis immediately following processing, or may be preserved and subjected to microscopic analysis at a future time, e.g., after storage for an extended period of time. In some embodiments, the methods described herein may be used to preserve tissue specimens in a stable, accessible and fully intact form for future analysis. For example, tissue specimens, such as, e.g., human brain tissue specimens, may be processed as described above and cleared to remove a plurality of cellular components, such as, e.g., lipids, and then stored for future analysis.

Tissues that have been preserved, or fixed, contain a variety of chemical modifications that can reduce the detectability of proteins in biomedical procedures. In some embodiments, the methods and systems described herein may be used to analyze a previously-preserved or stored tissue specimen. Previously preserved tissue specimens include, for example, clinical samples used in pathology including formalin-fixed paraffin-embedded (FFPE), hematoxylin and eosin (H&E)-stained, and/or fresh frozen tissue specimens. If the previously preserved sample has a coverslip, the coverslip should be removed. The sample is treated to remove the mounting medium. Such methods for removing the mounting medium are well known in the art. For example, treating the sample with xylene to remove paraffin or other hydrophobic mounting medium. Alternatively, if the sample is mounted in a water-based mounting medium, the sample is treated with water. The sample is then rehydrated and subjected to antigen-retrieval. The term "antigen retrieval" refers to any technique in which the masking of an epitope is reversed and epitope-antibody binding is restored such as, but not limited to, enzyme induced epitope retrieval, heat induced epitope retrieval (HIER), or proteolytic induced epitope retrieval (PIER). For example, the antigen retrieval treatment can be performed in a 10 mM sodium citrate buffer as well as the commercially available Target Retrieval Solution (DakoCytomation) or such.

In one embodiment, the biological specimen is a tissue sample useful for the diagnosis of a neoplastic lesion. In one embodiment, the neoplastic lesion is a benign neoplasm. In one embodiment, the neoplastic lesion is a tumor disease or cancer. The term "tumor" or "tumor disease" refers to a swelling or lesion formed by an abnormal growth of cells (called neoplastic cells or tumor cells). By "tumor cell" is meant an abnormal cell that grows by a rapid, uncontrolled cellular proliferation and continues to grow after the stimuli that initiated the new growth cease. Tumors show partial or complete lack of structural organization and functional coordination with the normal tissue, and usually form a distinct mass of tissue, which may be either benign, pre-malignant or malignant. In one embodiment, the tumor disease or cancer is a solid tumor.

The tumor disease may be a cancer disease, i.e. a malignant disease and a tumor cell is a cancer cell. In some embodiments, the tumor disease according is cancer, wherein the term "cancer" according to the invention comprises, but is not limited to, leukemias, lymphomas, seminomas, melanomas, teratomas, neuroblastomas, gliomas, rectal cancer, endometrial cancer, kidney cancer, adrenal cancer, thyroid cancer, blood cancer, skin cancer, cancer of the brain, cervical cancer, intestinal cancer, head and neck cancer, esophagus cancer, stomach cancer, intestine cancer, colon cancer, colorectal cancer, liver cancer, pancreatic cancer, ear, nose and throat (ENT) cancer, breast cancer, prostate cancer, cancer of the uterus, ovarian cancer and lung cancer. Examples thereof are lung carcinomas, mammary carcinomas, prostate carcinomas, colon carcinomas, renal cell carcinomas, or cervical carcinomas. The tumor disease may be breast cancer.

In some embodiments, the tumor diseases or cancers are selected from the group consisting of breast cancer, ovarian cancer, in particular ovarian adenocarcinoma and ovarian teratocarcinoma, lung cancer, including small cell lung cancer (SCLC) and non-small cell lung cancer (NSCLC), in particular squamous cell lung carcinoma and adenocarcinoma, gastric cancer, hepatic cancer, pancreatic cancer, skin cancer, in particular basal cell carcinoma and squamous cell carcinoma, malignant melanoma, head and neck cancer, in particular malignant pleomorphic adenoma, sarcoma, in particular synovial sarcoma and carcinosarcoma, bile duct cancer, cancer of the urinary bladder, in particular transitional cell carcinoma and papillary carcinoma, kidney cancer, in particular renal cell carcinoma including clear cell renal cell carcinoma and papillary renal cell carcinoma, colon cancer, small bowel cancer, including cancer of the ileum, in particular small bowel adenocarcinoma and adenocarcinoma of the ileum, testicular embryonal carcinoma, placental choriocarcinoma, cervical cancer, testicular cancer, in particular testicular seminoma, testicular teratoma and embryonic testicular cancer, and uterine cancer. The tumor disease or cancer may be breast cancer.

In some embodiments, the tumor diseases or cancers according to the invention are selected from the group consisting of breast cancer, ovarian cancer, lung cancer, metastatic ovarian cancer and metastatic lung cancer. The ovarian cancer may be an ovarian carcinoma or an ovarian adenocarcinoma. The lung cancer may be a carcinoma or an adenocarcinoma. The lung cancer may be a bronchiolar cancer such as a bronchiolar carcinoma or bronchiolar adenocarcinoma.

The main types of lung cancer are small cell lung carcinoma (SCLC) and non-small cell lung carcinoma (NSCLC). There are three main sub-types of the non-small cell lung carcinomas: squamous cell lung carcinoma, adenocarcinoma, and large cell lung carcinoma. Adenocarcinomas account for approximately 10% of lung cancers. This cancer usually is seen peripherally in the lungs, as opposed to small cell lung cancer and squamous cell lung cancer, which both tend to be more centrally located.

By "biomolecules" it is generally meant, but not limited to, proteins, lipids, steroids, nucleic acids, and sub-cellular structures within a tissue or cell.

By "macromolecules" is meant proteins, nucleic acids, or small molecules that target biomolecules within the specimen. These macromolecules are used to detect biomolecules within the specimen and/or anchor the biolmolecules to the swellable polymer. For example, macromolecules may be provided that promote the visualization of particular cellular biomolecules, e.g., proteins, lipids, steroids, nucleic acids, etc. and sub-cellular structures. In some embodiments, the macromolecules are diagnostic. In some embodiments, the macromolecules are prognostic. In some embodiments, the macromolecules are predictive of responsiveness to a therapy. In some embodiments, the macromolecules are candidate agents in a screen, e.g., a screen for agents that will aid in the diagnosis and/or prognosis of disease, in the treatment of a disease, and the like.

As an example, the specimen may be contacted with one or more polypeptide macromolecules, e.g. antibodies, labeled peptides, and the like, that are specific for and will bind to particular cellular biomolecules for either direct or indirect labeling by color or immunofluorescence. By immunofluorescence it is meant a technique that uses the highly specific binding of an antibody to its antigen or binding partner in order to label specific proteins or other molecules within the cell. A sample is treated with a primary antibody specific for the biomolecule of interest. A fluorophore can be directly conjugated to the primary antibody or peptide. Alternatively, a secondary antibody, conjugated to a detection moiety or fluorophore, which binds specifically to the first antibody can be used. Peptides that are specific for a target cellular biomolecule and that are conjugated to a fluorophore or other detection moiety may also be employed.

Another example of a class of agents that may be provided as macromolecules is nucleic acids. For example, a specimen may be contacted with an antisense RNA that is complementary to and specifically hybridizes to a transcript of a gene of interest, e.g., to study gene expression in cells of the specimen. As another example, a specimen may be contacted with a DNA that is complementary to and specifically hybridizes to genomic material of interest, e.g., to study genetic mutations, e.g., loss of heterozygosity, gene duplication, chromosomal inversions, and the like. The hybridizing RNA or DNA is conjugated to detection moieties, i.e. agents that may be either directly or indirectly visualized microscopically. Examples of in situ hybridization techniques may be found at, for example, Harris and Wilkinson. In situ hybridization: Application to developmental biology and medicine, Cambridge University Press 1990; and Fluorescence In Situ Hybridization (FISH) Application Guide. Liehr, T, ed., Springer-Verlag, Berlin Heidelberg 1990.

In one embodiment, the biological sample can be labeled or tagged with a detectable label. Typically, the label or tag will bind chemically (e.g., covalently, hydrogen bonding or ionic bonding) to a biomolecule of the sample, or a component thereof. The detectable label can be selective for a specific target (e.g., a biomarker or class of molecule), as can be accomplished with an antibody or other target specific binder. The detectable label may comprise a visible component, as is typical of a dye or fluorescent molecule; however, any signaling means used by the label is also contemplated. A fluorescently labeled biological sample, for example, is a biological sample labeled through techniques such as, but not limited to, immunofluorescence, immunohistochemical or immunocytochemical staining to assist in microscopic analysis. In one embodiment, the detectable label is chemically attached to the biological sample, or a targeted component thereof. In one embodiment, the detectable label is an antibody and/or fluorescent dye wherein the antibody and/or fluorescent dye, further comprises a physical, biological, or chemical anchor or moiety that attaches or crosslinks the specimen to the swellable polymer, such as a swellable hydrogel. The labeled sample may furthermore include more than one label. For example, each label can have a particular or distinguishable fluorescent property, e.g., distinguishable excitation and emission wavelengths. Further, each label can have a different target specific binder that is selective for a specific and distinguishable target in, or component of the sample.

In one embodiment, the sample contacted with a bi-functional linker wherein the bi-functional linker comprises a binding moiety and an anchor, wherein the binding moiety binds to biomolecules in the sample. The anchor may be a physical, biological, or chemical moiety that attaches or crosslinks the sample to the composition, hydrogel or other swellable material. This may be accomplished by crosslinking the anchor with the swellable material, such as during or after the polymerization, i.e., in situ formation of the swellable material. The anchor may comprise a polymerizable moiety. The anchor may include, but is not limited to, vinyl or vinyl monomers such as styrene and its derivatives (e.g., divinyl benzene), acrylamide and its derivatives, butadiene, acrylonitrile, vinyl acetate, or acrylates and acrylic acid derivatives. The polymerizable moiety may be, for example, an acrylamide modified moiety that may be covalently fixed within a swellable material.

As used herein a bifunctional crosslinker comprises reactive groups to functional groups (e.g., primary amines or sulfhydryls) on biomolecules within the sample. The bifunctional crosslinker may be used to chemically modify the amine group of biomolecules with a swellable polymer functional group, which enables antibodies and/or other endogenous biomolecules within the sample to be directly anchored to, or incorporate into, the swellable polymer. In one embodiment, the bifunctional crosslinker is a hetero-bifunctional crosslinker. Hetero-bifunctional crosslinkers possess different reactive groups at either end of a spacer arm, i.e., atoms, spacers or linkers separating the reactive groups. These reagents not only allow for single-step conjugation of molecules that have the respective target functional group, but they also allow for sequential (two-steps) conjugations that minimize undesirable polymerization or self-conjugation. The bi-functional linker may be a small molecule linker or a nucleic acid adaptor.

As used herein, a "nucleic acid adaptor" is a nucleic acid sequence having a binding moiety capable of attaching to a target nucleic acid and an anchor moiety capable of attaching to the swellable material. Attaching the nucleic acid adaptor to a target nucleic acid may be accomplished by hybridization or by ligation in situ. For example, DNA adaptors may be ligated to the 3' ends of the RNAs in the sample with RNA ligases, such as T4 RNA ligase, or may be attached via a chemical linker such as a reactive amine group capable of reacting with target nucleic acid. Acrylamide modified oligonucleotide primers may be covalently fixed within a swellable material such as a polyacrylate gel. As used herein, the term "acrylamide modified" in reference to an oligonucleotide means that the oligonucleotide has an acrylamide moiety attached to the 5' end of the molecule.

As used herein, a "small molecule linker" is a small molecule having a binding moiety capable of attaching to a target nucleic acid and an anchor moiety capable of attaching to the swellable material. Attaching the small molecule linker to the target nucleic acid may be accomplished by hybridization or by a chemical reactive group capable of covalently binding the target nucleic acid. For example, LABEL-IT® Amine (MirusBio) is a small molecule with alkylating group that primarily reacts to the N7 of guanine, thereby allowing covalent binding of RNA and DNA. The small molecule linker may be, for example, acrylamide modified and therefore may be covalently fixed within a swellable material. As used herein, the term "acrylamide modified" in reference to a small molecule linker means that the small molecule linker has an acrylamide moiety.

As used herein, the term "attach" or "attached" refers to both covalent interactions and noncovalent interactions. In certain embodiments of the invention, covalent attachment may be used, but generally all that is required is that the bi-functional linker remain attached to the target nucleic acid under conditions for nucleic acid amplification and/or sequencing. Oligonucleotide adaptors may be attached such that a 3' end is available for enzymatic extension and at least a portion of the sequence is capable of hybridizing to a complementary sequence. Attachment can occur via hybridization to the target nucleic acid, in which case the attached oligonucleotide may be in the 3'-5' orientation. Alternatively, attachment can occur by means other than base-pairing hybridization, such as the covalent attachment set forth above. The term "attach" may be used interchangeably herein with the terms, "anchor(ed)", affix(ed), link(ed) and immobilize(d).

In one embodiment, the bifunctional crosslinker may comprise a protein-reactive chemical moiety and a gel-reactive chemical moiety (i.e., a swellable polymer-reactive chemical moiety). The protein-reactive chemical group includes, but is not limited to, N-hydroxysuccinimide (NHS) ester, thiol, amine, maleimide, imidoester, pyridyldithiol, hydrazide, phthalimide, diazirine, aryl azide, isocyanate, or carboxylic acid, which, for example, can be reacted with amino or carboxylic acid groups on proteins or peptides. In one embodiment, the protein-reactive groups include, but are not limited to, N-succinimidyl ester, pentafluorophenyl ester, carboxylic acid, or thiol. The gel-reactive groups include, but are not limited to, vinyl or vinyl monomers such as styrene and its derivatives (e.g., divinyl benzene), acrylamide and its derivatives, butadiene, acrylonitrile, vinyl acetate, or acrylates and acrylic acid derivatives.

In one embodiment, the chemical to anchor proteins directly to any swellable polymer is a succinimidyl ester of 6-((acryloyl)amino)hexanoic acid (acryloyl-X, SE; abbreviated "AcX"; Life Technologies). Treatment with AcX modifies amines on proteins with an acrylamide functional group. The acrylamide functional groups allows for proteins to be anchored to the swellable polymer as it is synthesized in situ.

In one embodiment, the proteins of the sample can be modified with the protein-reactive group and the gel-reactive group in separate steps using click chemistry. Click chemistry, also referred to as tagging, is a class of biocompatible reactions intended primarily to join substrates of choice with specific biomolecules. In this method, proteins of the sample of interest are treated with a protein-reactive group comprising a click group and then treated with a gel-reactive group comprising a complementary click group. Complementary groups include, but are not limited to, azide groups and terminal alkynes (see e.g., H. C. Kolb; M. G. Finn; K. B. Sharpless (2001). "*Click Chemistry: Diverse Chemical Function from a Few Good Reactions*". Angewandte Chemie International Edition. 40(11): 2004-2021, which is incorporated herein by reference).

In one embodiment, the biological specimen may be embedded in a swellable polymer. By "swellable polymer" it is meant hydrophilic monomers, prepolymers, or polymers that can be crosslinked, or "polymerized", to form a three-dimensional (3D) polymer network, which expands when contacted with a liquid, such as water or other solvent. For example, one or more polymerizable materials, monomers or oligomers can be used, such as monomers selected from the group consisting of water soluble groups containing a polymerizable ethylenically unsaturated group. Monomers or oligomers can comprise one or more substituted or unsubstituted methacrylates, acrylates, acrylamides, methacrylamides, vinylalcohols, vinylamines, allylamines, allylalcohols, including divinylic crosslinkers thereof (e.g., N,N-alkylene bisacrylamides). Precursors can also comprise polymerization initiators and crosslinkers.

In one embodiment, the swellable polymer uniformly expands in 3 dimensions. Additionally or alternatively, the material may be transparent such that, upon expansion, light can pass through the sample. In one embodiment, the swellable polymer is a swellable hydrogel. In one embodiment, the swellable polymer is formed in situ from precursors thereof.

By "precursors of a swellable polymer", "hydrogel subunits" or "hydrogel precursors" is meant hydrophilic monomers, prepolymers, or polymers that can be crosslinked, or "polymerized", to form a three-dimensional (3D) hydrogel network. In one embodiment the swellable polymer is a polyelectrolyte. In one embodiment, the swellable polymer is polyacrylate or polyacrylamide and copolymers or crosslinked copolymers thereof.

Without being bound by scientific theory, it is believed that this fixation of the biological specimen in the presence of hydrogel subunits crosslinks the biomolecules of the specimen to the hydrogel subunits, thereby securing molecular components in place, preserving the tissue architecture and cell morphology.

The precursors of the swellable polymer may be delivered to the biological specimen by any convenient method including, but not limited to, permeating, perfusing, infusing, soaking, adding or other intermixing the sample with the precursors of swellable material. In this manner, the biological specimen is saturated with precursors of the swellable material, which flow between and around biomolecules throughout the specimen.

Following permeating the specimen, the swellable polymer precursors are polymerized, i.e., covalently or physically crosslinked, to form a polymer network. The polymer network is formed within and throughout the specimen. In this manner, the biological specimen is saturated with the swellable material, which flow between and around biomolecules throughout the specimen.

Polymerization may be by any method including, but not limited to, thermal crosslinking, chemical crosslinking, physical crosslinking, ionic crosslinking, photo-crosslinking, irradiative crosslinking (e.g., x-ray, electron beam), and the like, and may be selected based on the type of hydrogel used and knowledge in the art. In one embodiment, the polymer is a hydrogel. Once polymerized, a polymer-embedded biological specimen is formed.

The swellable polymer may be a polyacrylate or polyacrylamide and copolymers or crosslinked copolymers thereof. For example, if the biological sample is to be embedded in sodium polyacrylate, a solution comprising the monomers sodium acrylate and acrylamide, and a crosslinker selected from N,N-methylenebisacrylamide (BIS), N,N'-(1,2-Dihydroxythylene)bisacrylamide), and (DHEBA) N,N'-Bis(acryloyl)cystamine (BAC), are perfused throughout the sample.

The swellable material may be a hydrogel. The hydrogel may be a polyelectrolyte hydrogel. The polyelectrolyte may be a polyacrylate.

In some embodiments, native proteins anchored to the swellable polymer perfused throughout the sample as described herein can retain epitope functionality and be labeled post-expansion if the nonspecific proteolysis of ExM is replaced with modified post-gelation homogenization treatments. Such approaches may overcome the limitations inherent to delivering antibodies in the crowded environment of native tissue.

By embedding a specimen in a swellable polymer that physically supports the ultrastructure of the specimen this technology preserves the biomolecules (e.g., proteins, small peptides, small molecules, and nucleic acids in the specimen) in their three-dimensional distribution, secured by the polymer network. By bypassing destructive sectioning of the specimen, subcellular structures may be analyzed. In addition, the specimen can be iteratively stained, unstained, and restained with other reagents for comprehensive analysis.

The sample may be attached or crosslinked to the swellable material before expansion. This may be accomplished, for example, by crosslinking the anchor with the swellable material, such as during or after the polymerization, i.e., in situ formation of the swellable material.

After the biological sample has been anchored to the swellable polymer, the specimen is subjected to a disruption of the endogenous biological molecules (or the physical structure of the biological sample), leaving the macromolecules, e.g., label or tag, that preserve the information of the targeted biological molecules intact and anchored to the swellable polymer. In this way, the mechanical properties of the specimen-swellable polymer complex are rendered more spatially uniform, allowing greater and more consistent isotropic expansion.

The disruption of the endogenous physical structure of the specimen or of the endogenous biological molecules of the biological specimen generally refers to the mechanical, physical, chemical, biochemical or enzymatic digestion, disruption or break up of the sample so that it will not resist expansion. In one embodiment, a non-specific protease is used to homogenize the sample-swellable polymer complex.

The disruption should not impact the structure of the swellable material but disrupt the structure of the sample. Thus, the sample disruption should be substantially inert to the swellable material. The degree of digestion can be sufficient to compromise the integrity of the mechanical structure of the sample or it can be complete to the extent that the sample-swellable material complex is rendered substantially free of the sample. The disruption of the physical structure of the sample may be protein digestion of the proteins contained in the biological sample.

In one embodiment, the non-specific protease is in a buffer having a pH from about 4 to about 12. Any suitable buffer agent can be used including, but not limited to, Tris, citrate, phosphate, bicarbonate, MOPS, borate, TAPS, bicine, Tricine, HEPES, TES, and MES. In one embodiment, the buffer comprises a non-specific protease, a metal ion chelator, a nonionic surfactant, and a monovalent salt. In one embodiment, the buffer comprises about 1 U/ml to about 100 U/ml of a non-specific protease; about 5 mM to about 100 mM metal ion chelator; about 0.1% to about 1.0% nonionic surfactant; and about 0.05 M to about 1 M monovalent salt. In one embodiment, the sample is incubated in the buffer for about 0.5 to about 3 hours at about 50° C. to about 70° C. In one embodiment, the sample is incubated in the buffer until the sample is completely digested.

Non-specific proteases are well known to those of skill in the art. Non-specific proteases include, but are not limited to, proteinase K, Subtilisin, Pepsin, Thermolysin, and Elastase. In one embodiment the buffer comprises about 1 U/ml to about 100 U/ml of a non-specific protease. In one embodiment the buffer comprises about 1 U/ml to about 50 U/ml of a non-specific protease. In one embodiment the buffer comprises about 1 U/ml to about 25 U/ml of a non-specific protease. In one embodiment the buffer comprises about 1 U/ml to about 10 U/ml of a non-specific protease.

Chelating agents are well known to those of skill in the art. Chelating agents include, but are not limited to, EDTA, EGTA, EDDHA, EDDS, BAPTA and DOTA. In one embodiment the buffer comprises about 5 mM to about 100 mM of a metal ion chelator. In one embodiment the buffer comprises about 5 mM to about 75 mM of a metal ion chelator. In one embodiment the buffer comprises about 5 mM to about 50 mM of a metal ion chelator.

Nonionic surfactant are well known to those of skill in the art. Nonionic surfactants include, but are not limited to, Triton X-100, Tween 20, Tween 80, Sorbitan, Polysorbate 20, Polysorbate 80, PEG, Decyl glucoside, Decyl polyglucose and cocamide DEA. In one embodiment the buffer comprises about 0.1% to about 1.0% nonionic surfactant. In one embodiment the buffer comprises about 0.1% to about 0.75% nonionic surfactant. In one embodiment the buffer comprises about 0.1% to about 0.5% nonionic surfactant. In one embodiment the buffer comprises about 0.1% to about 0.3% nonionic surfactant.

Monovalent cation salts are well known to those of skill in the art. Monovalent cation salts contain cations that include, but are not limited to, $Na^+$, $K^+$, ammonium, and $Cs^+$. In one embodiment, the buffer comprises about 0.05 M to about 1.0 M monovalent salt. In one embodiment, the buffer comprises about 0.05 M to about 1.0 M monovalent salt. In one embodiment, the buffer comprises about 0.75 M to about 1.0 M monovalent salt. In one embodiment, the buffer comprises about 0.1 M to about 1.0 M monovalent salt. In one embodiment, the buffer comprises about 0.1 M to about 0.7 M monovalent salt. In one embodiment, the buffer comprises about 0.05 M to about 0.8 M monovalent salt.

It is preferable that the disruption does not impact the structure of the swellable polymer but disrupts the structure of the specimen. Thus, the specimen disruption should be substantially inert to the swellable polymer. The degree of digestion can be sufficient to compromise the integrity of the mechanical structure of the specimen or it can be complete to the extent that the specimen-swellable polymer complex is rendered substantially free of the sample.

The specimen-swellable polymer complex is then expanded for example, by contacting the swellable polymer with a solvent or liquid which is then absorbed by the swellable polymer and causes swelling. Where the swellable polymer is water swellable, an aqueous solution can be used. The swelling of the swellable polymer results in the specimen itself expanding (e.g., becoming larger). This is because the polymer is embedded throughout the specimen, therefore, as the polymer swells (grows) it expands and causes the anchored biomolecules to pull apart (i.e., move away) from each. In one embodiment, the swellable polymer expands (swells) isotropically; therefore, the anchored biomolecules retain the relative spatial orientation within the specimen.

The swollen biological specimen-polymer complex can be imaged on any imaging device. The swollen biological specimen-polymer complex can be imaged on any optical microscope, allowing effective imaging of features below the classical diffraction limit. Since the resultant specimen can be transparent, custom microscopes capable of large volume, wide field of view, 3D scanning may also be used in conjunction with the expanded sample. The method also provides an optional step comprising amplification of the detectable label.

Using the described methods, reagents, kits, systems and devices, the ordinarily skilled artisan will be able to prepare any biological specimen for microscopic analysis. Methods, reagents, kits, systems and devices may be used to prepare a specimen from any plant or animal, including but not limited to transgenic animals, e.g., vertebrate or invertebrate, e.g. insect, worm, xenopus, zebrafish, mammal, e.g. equine, bovine, ovine, canine, feline, murine, rodent, non-human primate or human. Tissue specimens may be collected from living subjects (e.g., biopsy samples) or may be collected from dead subjects (e.g., autopsy or necropsy samples). The specimens may be of any tissue type, e.g. hematopoietic, neural (central or peripheral), glial, mesenchymal, cutaneous, mucosal, stromal, muscle (skeletal, cardiac, or smooth), spleen, reticulo-endothelial, epithelial, endothelial, hepatic, kidney, pancreatic, gastrointestinal, pulmonary, fibroblast, and other cell types. In some instances, the specimen is the entire organism, e.g. a worm, an insect, a zebrafish. In other instances, the specimen is a whole organ, e.g., the whole brain of a rodent. In other instances, the specimen is a portion of an organ, i.e. a biopsy, e.g. a biopsy of a transplanted tissue. The specimen may be freshly isolated or preserved, e.g. snap frozen. In some embodiments, the specimen may be a previously preserved specimen, such as, e.g., a preserved specimen from a tissue bank, e.g., a preserved specimen of a human brain obtained from a tissue collection program. In some instances, a specimen may be from a subject known to suffer from a specified disease or condition, such as, e.g., a sample of brain tissue from an autistic human. In other instances, a sample may be from a "normal" subject that does not suffer from a specific disease or condition. In some instances, a sample may be from a transgenic subject, such as, e.g., a transgenic mouse.

Because the cells and/or biomolecules of the specimen are anchored to a swellable polymer that physically supports the ultrastructure of the specimen, cellular components (e.g. lipids) that normally provide structural support but that hinder visualization of subcellular proteins and molecules may be removed while preserving the 3-dimensional architecture of the cells and tissue. This removal renders the interior of biological specimen substantially permeable to light and/or macromolecules, allowing the interior of the specimen, e.g. cells and subcellular structures, to be microscopically visualized without time-consuming and disruptive sectioning of the tissue. Additionally, the specimen can be iteratively stained, unstained, and re-stained with other reagents for comprehensive analysis.

The subject methods find many uses. For example, the subject methods may be applied to preparing specimens for the study of the connectivity of the central nervous system. "Connectivity" as used herein generally means the connections between neurons, and includes connections at the single cell level, e.g., synapses, axon termini, dendritic spines, etc., as well as connections between groups of neurons and regions of the CNS as major axon tracts, e.g., corpus callosum (CC), anterior commissure (AC), hippocampal commissure (HC), pyramidal decussation, pyramidal tracts, external capsule, internal capsule (IC), cerebral peduncle (CP), etc. A whole brain and/or spinal cord specimen or region thereof (e.g., cerebrum (i.e., cerebral cortex), cerebellum (i.e., cerebellar cortex), ventral region of the forebrain (e.g., striatum, caudate, putamen, globus pallidus, nucleus accumbens; septal nuclei, subthalamic nucleus); regions and nuclei of the thalamus and hypothalamus; regions and nuclei of the deep cerebellum (e.g., dentate nucleus, globose nucleus, emboliform nucleus, fastigial nucleus) and brainstem (e.g., substantia nigra, red nucleus, pons, olivary nuclei, cranial nerve nuclei); and regions of the spine (e.g. anterior horn, lateral horn, posterior horn)) may be prepared post-mortem by the subject methods and the connectivity of the neurons therein microscopically analyzed, e.g., obtained, stored, rendered, used, and actuated, e.g., to provide the full connectivity of a brain, e.g., a human brain, after death. Such studies will contribute greatly to the understanding of how the brain develops and functions in health and during disease, and of the underpinnings of cognition and personality.

As another example, the subject methods may be employed to evaluate, diagnose or monitor a disease. "Diagnosis" as used herein generally includes a prediction of a subject's susceptibility to a disease or disorder, determination as to whether a subject is presently affected by a disease or disorder, prognosis of a subject affected by a disease or disorder (e.g., identification of cancerous states, stages of cancer, likelihood that a patient will die from the cancer), prediction of a subject's responsiveness to treatment for a disease or disorder (e.g., a positive response, a negative response, no response at all to, e.g., allogeneic hematopoietic stem cell transplantation, chemotherapy, radiation therapy, antibody therapy, small molecule compound therapy) and use of therametrics (e.g., monitoring a subject's condition to provide information as to the effect or efficacy of therapy). For example, a biopsy may be prepared from a cancerous tissue and microscopically analyzed to determine the type of cancer, the extent to which the cancer has developed, whether the cancer will be responsive to therapeutic intervention, etc.

As another example, a biopsy may be prepared from a diseased tissue, e.g. kidney, pancreas, stomach, etc., to determine the condition of the tissue, the extent to which the disease has developed, the likelihood that a treatment will be successful, etc. The terms "treatment", "treating" and the like are used herein to generally mean obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment" as used herein covers any treatment of a disease in a mammal, and includes: (a) preventing the disease from occurring in a subject which may be predisposed to the disease but has not yet been diagnosed as having it; (b) inhibiting the disease, i.e., arresting its development; or (c) relieving the disease, i.e., causing regression of the disease. The therapeutic agent may be administered before, during or after the onset of disease or injury. The treatment of ongoing disease, where the treatment stabilizes or reduces the undesirable clinical symptoms of the patient, is of particular interest. Such treatment is desirably performed prior to complete loss of function in the affected tissues. The subject therapy will desirably be administered during the symptomatic stage of the disease, and in some cases after the symptomatic stage of the disease. The terms "individual," "subject," "host," and "patient," are used interchangeably herein and refer to any mammalian subject for whom diagnosis, treatment, or therapy is desired, particularly humans. Examples of diseases that are suitable to evaluation, analysis, diagnosis, prognosis, and/or treatment using the subject methods and systems include, but are not limited to, cancer, immune system disorders, neuropsychiatric disease, endocrine/reproductive disease, cardiovascular/pulmonary disease, musculoskeletal disease, gastrointestinal disease, and the like.

The subject methods may also be used to evaluate normal tissues, organs and cells, for example to evaluate the relationships between cells and tissues of a normal tissue specimen, e.g., a tissue specimen taken from a subject not known to suffer from a specific disease or condition. The subject methods may be used to investigate, e.g., relationships between cells and tissues during fetal development, such as, e.g., during development and maturation of the nervous system, as well as to investigate the relationships between cells and tissues after development has been completed, e.g., the relationships between cells and tissues of the nervous systems of a fully developed adult specimen.

The subject methods also provide a useful system for screening candidate therapeutic agents for their effect on a tissue or a disease. For example, a subject, e.g. a mouse, rat, dog, primate, human, etc. may be contacted with a candidate agent, an organ or a biopsy thereof may be prepared by the subject methods, and the prepared specimen microscopically analyzed for one or more cellular or tissue parameters. Parameters are quantifiable components of cells or tissues, particularly components that can be accurately measured, desirably in a high throughput system.

The subject methods may also be used to visualize the distribution of genetically encoded markers in whole tissue at subcellular resolution, for example, chromosomal abnormalities (inversions, duplications, translocations, etc.), loss of genetic heterozygosity, the presence of gene alleles indicative of a predisposition towards disease or good health, likelihood of responsiveness to therapy, ancestry, and the like. Such detection may be used in, for example, diagnosing and monitoring disease as, e.g., described above, in personalized medicine, and in studying paternity.

As used herein the phrase "diagnostic" means identifying the presence or nature of a pathologic condition. Diagnostic methods differ in their sensitivity and specificity. The "sensitivity" of a diagnostic assay is the percentage of diseased individuals who test positive (percent of "true positives"). Diseased individuals not detected by the assay are "false negatives." Subjects who are not diseased and who test negative in the assay are termed "true negatives." The "specificity" of a diagnostic assay is 1 minus the false positive rate, where the "false positive" rate is defined as the proportion of those without the disease who test positive. While a particular diagnostic method may not provide a definitive diagnosis of a condition, it suffices if the method provides a positive indication that aids in diagnosis.

As used herein the phrase "diagnosing" refers to classifying a disease or a symptom, determining a severity of the disease, monitoring disease progression, forecasting an outcome of a disease and/or prospects of recovery. The term "detecting" may also optionally encompass any of the above.

In some embodiments, the enlarged sample can be re-embedded in a non-swellable polymer. "Re-embedding" comprises permeating (such as, perfusing, infusing, soaking, adding or other intermixing) the sample with the non-swellable polymer, preferably by adding precursors thereof. Alternatively or additionally, embedding the sample in a non-swellable polymer comprises permeating one or more monomers or other precursors throughout the sample and polymerizing and/or crosslinking the monomers or precursors to form the non-swellable polymer or polymer. In this manner the first enlarged sample, for example, is embedded in the non-swellable polymer. Embedding the expanded sample in a non-swellable polymer prevents conformational changes during sequencing despite salt concentration variation. The non-swellable polymer can be charge-neutral hydrogels. For example, it can be polyacrylamide hydrogel, composed of acrylamide monomers, bisacrylamide cross-linker, ammonium persulfate (APS) initiator and tetramethylethylenediamine (TEMED) accelerator.

In some embodiments, the fixed biological sample is subjected to passivation. As used herein the term "passivation" refers to the process for rendering the sample less reactive with the components contained within the fixative such as by functionalizing the fixative with chemical reagents to neutralize charges within. For example, the carboxylic groups of acrylate, which may be used in the swellable gel, can inhibit downstream enzymatic reactions. Treating the swellable gel composed of acrylate with 1-Ethyl-3-(3-dimethylaminopropyl)carbodiimide (EDC) and N-Hydroxysuccinimide (NHS) allows primary amines to covalently bind the carboxylic groups to form charge neutral amides and passivate the swellable gel.

The innovation enables physical expansion of common clinical tissue specimen based on the unique physical and chemical properties of clinical tissue specimens. Clinical tissue specimens are usually highly fixed, tightly attached on the superfrost glass slides, and embedded in the paraffin (or stained and mounted in a mounting medium) for long-term storage. Some clinical tissue specimens are stained with dyes, such as hematoxylin and eosin (H&E), which are incompatible with fluorescence imaging. To apply ExM to clinical samples, de-paraffinization, antigen retrieval and aggressive protease digestion are integrated in a comprehensive workflow to handle various kinds of common clinical specimens. De-paraffinization and antigen retrieval address the recovery of archived clinical samples, while aggressive protease digestion is critical for the success of sample expansion, as most of the human tissues contain abundant hard-to-digest structural proteins, such as collagen and fibronectin, which prevent homogeneous expansion of the sample. Taken together, the present invention allows for the application of ExM to the enormous amount of archived clinical samples and enable super-resolution optical interrogations of mechanisms of a broad range of diseases by conventional optical microscopy.

This invention provides a comprehensive workflow to facilitate expansion of common types of clinical samples for super-resolution molecular imaging. The methods described herein will result in optimal outcomes, such as proper immunostaining, sufficient digestion of tissue, high quality of polymer synthesis, and maintenance of proteins of interest during expansion.

The invention also describes the reutilization of classic H&E stained slides for further biomolecular interrogation in nanoscale level. In general, H&E stained slides are not considered suitable for further downstream processing due to the difficulty in removing the stain and mounting medium. Thus, the invention describes a unique and cost-effective approach to overcome this barrier and enable the extraction of more information from the used H&E slides. In one embodiment, the method of expanding H&E stained slides for further utilization combines xylene-ethanol-water sequential washing, protein anchoring and in situ polymer synthesis.

EXAMPLES

Human Samples.

The breast pathological specimens used in this study were from the pathology archives of the Beth Israel Deaconess Medical Center and were used under BIDMC IRB protocol #2013p000410 to AHB. The frozen kidney pathological samples were provided by the Brigham and Woman's archives under the BWH IRB protocol #2011P002692 to AW. Other human tissue samples and tissue microarrays were purchased from commercial sources (see Table 1).

TABLE 1

Human samples purchased from commercial sources

| Sample | Manufacturer | Catalog No. |
| --- | --- | --- |
| IHC control tissue array for HER2 molecule | Abcam | ab178176 |
| Human Adult Normal: Lung (FFPE) | US Biomax | HuFPT131 |
| Multi-tumor tissue array, 95 cases of 40 types from 27 organs/sites (1.5 mm) | Abcam | ab178234 |
| Human Adult Normal: Kidney (Fresh Frozen slides) | US Biomax | HuFTS241 |
| Breast hyperplasia tissue array, 80 cases/80 cores | US Biomax | BR806 |
| Breast pre-cancerous disease and cancer tissue array (100 cases/101 cores) | US Biomax | BR1003 |
| Breast common disease tissue array of 102 cases (1.5 mm) | Abcam | ab178113 |
| Breast cancer tissue array with progressive changes, 48 cases, 96 samples (1.5 mm) | Abcam | Ab178112 |

The use of unidentified archival specimens do not require informed consent from the subjects.

Sample Preparation Prior to Antigen Retrieval

For Paraffin Embedded Clinical Samples

In one embodiment the workflow is summarized in FIG. 1. In embodiments wherein the clinical tissue sample is embedded in paraffin, deparaffinization is required. Deparaffinization is performed by placing the slides in a Coplin jar and sequentially washing the clinical tissue sample using the following solutions: (a) 2×Xylene, (b) 1:1 Xylene:100% Ethanol, (c) 2×100% ethanol, (d) 95% ethanol, (e) 70% ethanol, (f) 50% ethanol, and finally (g) cold tap water. In some embodiments the clinical tissue sample is washed for 3 minutes in each solution. In some embodiments the clinical tissue sample is washed at room temperature. In embodiments wherein the paraffin embedded clinical tissue sample is on a glass slide, the slide is wash sequentially in the solutions as described herein. In some embodiments, the paraffin-embedded clinical samples is part of a tissue microarray. In some embodiments, the paraffin-embedded clinical samples is a tissue microarray. In some embodiments the paraffin-embedded clinical samples are deparaffinized using a deparaffinization solution (QIAGEN).

In some embodiments, for formalin-fixed paraffin-embedded (FFPE) clinical samples, samples were placed in a series of solutions sequentially, 3 mins for each step: 2×xylene, 2×100% ethanol, 95% ethanol, 70% ethanol, 50% ethanol, and finally double deionized water. All the steps were performed at room temperature (RT).

For Stained and Mounted Permanent Slides

In embodiments wherein the clinical tissue sample is stained and mounted on a permanent slide the coverslip of the slide is first carefully removed. The coverslip can be removed with any appropriate tool, for example, a razor blade and if the coverslip is difficult to remove, pre-treatment with a xylene solution will help loosen the coverslip. The slide is then washed sequentially with the xylene-based de-paraffinization solutions discussed above. In some embodiments, the clinical tissue samples are stained with H&E.

In some embodiments, the slides were treated as FFPE samples discussed above.

In embodiments where the clinical tissue sample is stained with a water-soluble stain such as eosin, the stain can be washed away with water. In embodiments where the clinical tissue sample is stained with an insoluble stain, of further stained with an insoluble stain, such as hematoxylin, the insoluble stain can be removed by washing the clinical tissue sample with the xylene-based de-paraffinization solutions discussed above, or such insoluble stain may remain in the sample, but can be oxidized and removed after in situ polymer synthesis, digestion and expansion steps.

In some embodiments the insoluble stain can be removed by placing the slide comprising the clinical tissue sample in a 0.1 M HCl solution until the insoluble stain is completely removed. In some embodiments the insoluble stain is hematoxylin. The drawback of removing the insoluble stain in the 0.1 M HCL solution is that the tissue may de-attach from the glass slide in the later steps.

In embodiments where the clinical tissue samples are fixed and frozen on a glass slide, the clinical tissue samples are left at room temperature to allow the freeze cutting medium to melt. If the clinical tissue sample is embedded in paraffin, the sample is de-paraffinized as discussed above.

In one embodiment, unfixed frozen tissue slides in optimum cutting temperature (OCT) solution (Tissue-Tek) were initially fixed for 5-10 min in ice cold acetone at −20° C. before 3×PBS washing. For already fixed and frozen clinical tissue sections, the slides were left at RT for 2 mins, to let the OCT solution melt and washed 3× with PBS solution.

Once the clinical tissue samples have been de-paraffinized, or if the clinical tissue samples are not embedded in paraffin but are fixed with paraformaldehyde or similar aldehyde-based chemicals, the clinical tissue sample then proceeds to the antigen retrieval step.

Antigen Retrieval

In embodiments where the clinical samples that are fixed by formalin or similar aldehyde-based chemicals, the clinical tissue samples must be treated with antigen-retrieval procedures prior to the immunostaining step. If the clinical tissue samples were not paraffin embedded, or have been de-paraffinized, and are not fixed by formalin or similar aldehyde-based chemicals, the clinical tissue samples can proceed to the immunostaining step.

In embodiments where the clinical tissue samples must be treated with antigen retrieval procedures, any heat induced epitope retrieval or enzyme induced epitope retrieval methods known to one skilled in the art or their combination of any kind may be used for antigen retrieval. For example, in some embodiments, the clinical tissue samples can be are placed in 10 mM sodium citrate solution (pH 8.5), for 5 mins at RT, then transferred to 10 mM sodium citrate solution (pH 8.5) for 30 mins at 80-100° C.

In one embodiment, tissue slides were placed in 20 mM sodium citrate solution (pH 8.5) around 100° C., and were cooled down in 60° C. incubation chamber for 30 mins.

Immunohistochemistry

Once the clinical tissues samples have been de-paraffinized and subjected antigen retrieval, as necessary, the clinical tissue samples are then immunostained by any method known to one skilled in the art. In some embodiments, samples are first blocked with MAXBLOCK™ Blocking Medium (Active Motif) for 1 hour at 37° C., followed by incubation with primary antibodies in MAXSTAIN™ Staining Medium (Active Motif) at a concentration of 10 μg/mL for about 1 minute to about several days at about 0° C. to about 40° C. depending on tissue thickness and antibody. In some embodiments, the clinical tissue samples are incubated with the primary antibodies for 6-24 hours. In some embodiments, the clinical tissue samples are incubated with the primary antibodies at about room temperature to about 37° C. In some embodiments, the clinical tissue samples are incubated with the primary antibodies at about room temperature. In some embodiments, the clinical tissue samples are incubated with the primary antibodies at about 37° C. The clinical tissues samples are then washed in MAXWASH™ Washing Medium (Active Motif) four times, for 5-30 minutes each, changing solutions in between. The clinical tissue samples are then incubated with appropriate secondary antibodies at a concentration of approximately 10 μg/mL together with 300 nM DAPI in MAXSTAIN™ Staining Medium for about 1 minute to about several days at about 0° C. to about 40° C. depending on tissue thickness and antibody. In some embodiments, the clinical tissue samples are incubated with the primary antibodies for 6-24 hours. In some embodiments, the clinical tissue samples are incubated with the primary antibodies at about room temperature to about 37° C. In some embodiments, the clinical tissue samples are incubated with the primary antibodies at about room temperature. In some embodiments, the clinical tissue samples are incubated with the primary antibodies at about 37° C. The clinical tissue samples are then washed in MAXWASH™ Washing Medium several times.

Chemical Treatment for Protein Preservation

Once the clinical tissues samples have been de-paraffinized and subjected antigen retrieval, as necessary, and the clinical tissue samples are immunostained, the samples can be treated for protein perseveration as described by in WO 2017/027368, which is incorporated herein by reference. In some embodiments, the clinical tissue sample is treated by incubation in PBS buffer containing 0.03-0.2 mg/ml Acryloyl X Acryloyl-X, SE (6-((acryloyl)amino)hexanoic acid, succinimidyl ester, here abbreviated AcX; (Thermo Fisher Scientific), for 2-12 hours.

In one embodiment, AcX was dissolved in anhydrous DMSO at a concentration of 10 mg/mL, aliquoted and stored frozen in a desiccated environment. Tissue slides were incubated with 0.03-0.1 mg/ml AcX (0.03 mg/ml for samples fixed with non-aldehyde fixatives, 0.1 mg/ml for samples fixed with aldehyde fixatives) diluted in PBS buffer for more than 6 hours at RT.

In Situ Polymer Synthesis

Once the clinical tissues samples have been de-paraffinized and subjected antigen retrieval, as necessary, and the clinical tissue samples are immunostained and, optionally, treated for protein perseveration, the clinical tissue samples are subjected to in situ polymer synthesis. Briefly, monomer solution including 1×PBS, 2 M NaCl, 8.625% (w/w) sodium acrylate, 2.5% (w/w) acrylamide, 0.10% (w/w) N,N'-methylenebisacrylamide (all from Sigma Aldrich), was prepared and aliquoted prior to in situ polymer synthesis. Tissue slides were incubated with the monomer solution for about 1 hour at 4° C. to allow complete diffusion of monomer solution and prevent premature gelation. 4-hydroxy-2,2,6,6-tetramethylpiperidin-1-oxyl (Sigma Aldrich) as inhibitor, tetramethylethylenediamine as accelerator and ammonium persulfate as initiator, were added sequentially to the monomer solution up to 0.2% (w/w) each. Finally, samples were incubated for 1.5-2 hour at 37° C. with humidified atmosphere to complete gelation.

In some embodiments, a monomer solution including sodium acrylate, acrylamide, and bisacrylamide, salt and buffer is prepared prior to in situ polymer synthesis. The monomer solution may be cooled at 4° C. to prevent premature gelation. Ammonium persulfate as initiator, tetramethylethylenediamine as accelerator and 4-hydroxy-2,2,6,6-tetramethylpiperidin-1-oxyl as inhibitor are added to the monomer solution up to 0.2% (w/w) each. Tissue slides are incubated with the monomer solution at 4° C. (for variable time depending on thickness) to allow monomer solution to diffuse, and then incubate in 37° C. with humidified atmosphere for 1-2 hour to enable gelation.

After the completion of polymerization, the regions of interest are cut using razor blades or appropriate tool (For slide samples, the tissues remain attached to the slides). In some embodiments, the regions of interest from samples can be cut out after the sample has been expanded. In some embodiments, the regions of interest from samples are cut out prior to expansion.

Sample Digestion and Expansion

Once the clinical tissues samples have been subjected to in situ polymer synthesis, the clinical tissue samples are incubated in 4-32 U/ml proteinase K (New England Biolabs) in a modified digestion buffer comprising 50 mM Tris (pH 8), 5-100 mM EDTA, 0.25% Triton X-100, and 0.4 M guanidine HCl. In some embodiments, the clinical tissue samples are incubated at 50° C. for at least 8 hours until the completion of digestion.

In some embodiments, the clinical tissue samples are hard to digest, as regular buffers for proteinase K digestion do not work well with clinical tissue samples; thereby, making it difficult to ensure reliable digestion of the sample. Thus, the invention also describes a "digestion during expansion" method to overcome this problem. In some embodiments, the clinical tissue samples and the proteinase K are incubated in a modified digestion buffer comprising 50 mM Tris (pH 8), 25 mM EDTA, 0.25% Triton X-100, and 0.4 M guanidine HCl. The salt concentration is maintained at a low ionic strength which promotes moderate expansion of the tissue sample during the digestion and enables better penetration of digestive enzyme inside the tissue. To further aid digestion, high concentration of disodium salt of ethylenediaminetetraacetic acid (EDTA) is used to chelate any residual divalent cation that maintains the structural integrity of structural proteins in the tissues, such as collagen and fibronectin. The incubation temperature is set to increase enzyme activities.

In some embodiments, samples were incubated in 8 U/ml proteinase K (New England Biolabs) in a modified digestion buffer containing 50 mM Tris (pH 8), 25 mM EDTA, 0.25% Triton X-100, 0.4 M guanidine HCl (or 0.4 M NaCl), and the tissues were incubated for 0.5-3 hours at 60° C. or until the completion of digestion. Digested samples were washed once with 1×PBS buffer and stained with 300 nM DAPI in PBS buffer for 1 hour, then washed at least twice with 1×PBS for at least 20 minutes each wash. Finally, gels were placed in doubly deionized water for 10 mins to expand. This step was repeated 3-5 times in fresh water or 0.002%~0.01% sodium azide solution (to prevent bacterial growth), until the size of the expanding sample remained unchanged.

In some embodiments, the completion of digestion of the clinical tissue samples results in loose detachment of the tissues on the slides. In some embodiments, the clinical tissue samples can be separated from the slides. In some embodiments, the clinical tissue samples can be stained with DAPI or other chemical nucleus stains. In one embodiment, the clinical tissue samples are washed once with 1×PBS buffer after digestion and stained with 300 nM DAPI in PBS buffer for 1 hour, then washed at least twice with 1×PBS for at least 20 minutes each wash. If the samples are stained with DAPI or other chemical nucleus stains before the in situ polymer synthesis, the stain would diffuse away in the digestion buffer. To recover the nucleus staining, the samples are washed once with 1×PBS buffer after digestion and stained with 300 nM DAPI in PBS buffer for 1 hour, then washed at least twice with 1× PBS for at least 20 minutes each wash. Finally, the sample is expanded by iterative washing with Milli Q water.

DNA FISH

In some embodiments, for expanded samples being processed further for DNA FISH, the digested gel samples were placed in the hybridization buffer containing 1×PBS, 15% ethylene carbonate, 20% dextran sulfate, 600 mM NaCl and 0.2 mg/ml single stranded salmon sperm DNA at 85° C. for 30 mins, then mixed with 30 µL of hybridization buffer containing SureFISH probes (Agilent/Dako) pre-heated at 85° C. for 10 mins. The mixtures were then incubated at 45° C. overnight. The next day, the samples were washed with stringency wash buffer containing 1×SSC (150 mM NaCl, 15 mM sodium citrate, pH 7.0) and 20% ethylene carbonate at 45° C. for 15 min, followed by a wash with 2×SSC at 45° C. for 3 times 10 mins each. Finally, the gel samples were washed with 0.02×SSC multiple times (5 mins each) until the expansion was completed.

Imaging

Figure 2:
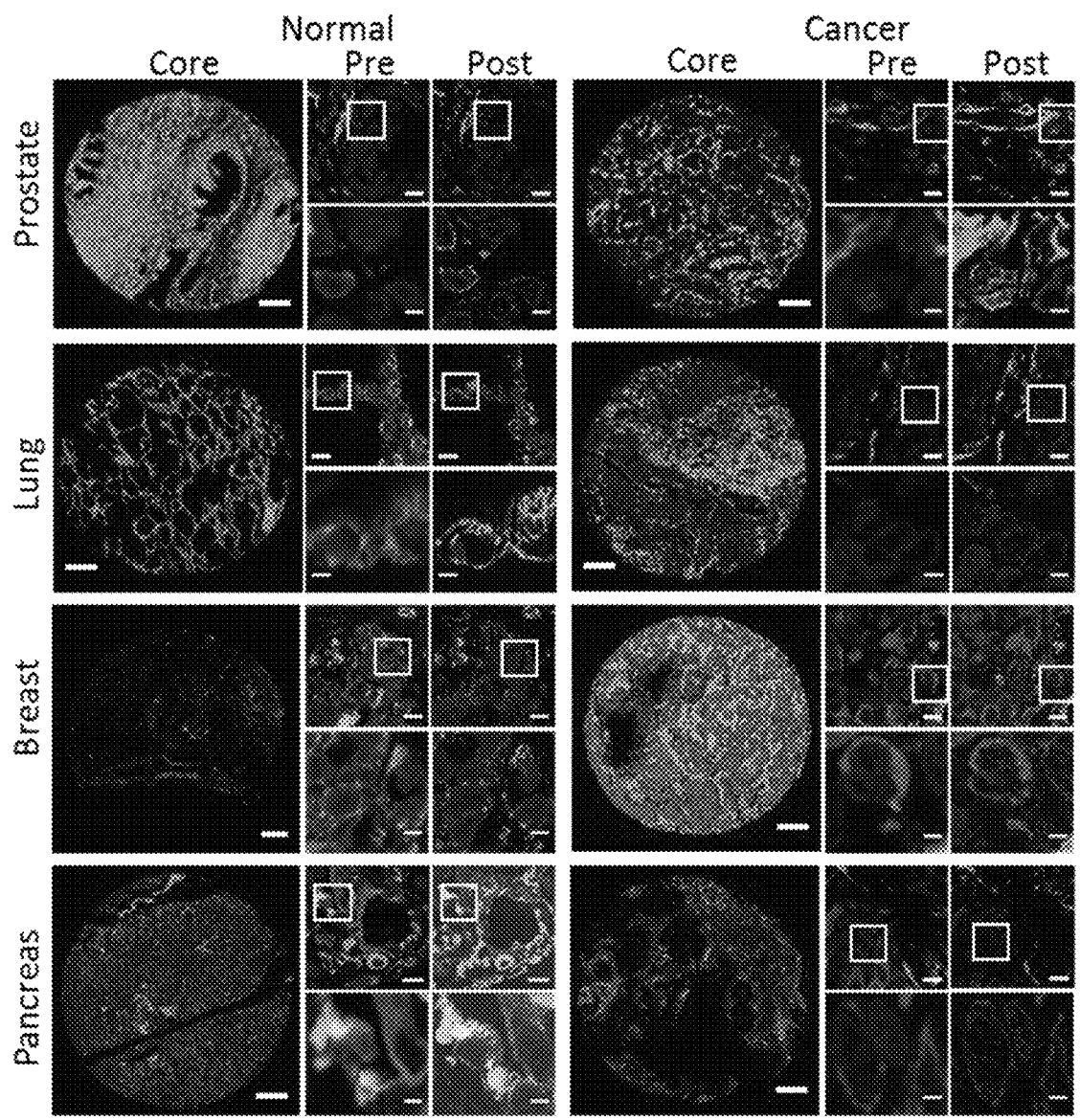
FIG. 2 depicts ExPath imaging of a wide range of human tissue samples. Images of various tissue types for both normal (left images) and cancerous (right images) tissues from human patients. From top to bottom, different rows show different tissue types as labeled (e.g., prostate, lung, breast, etc.). Within each block of images for a given tissue x disease type, there are 5 images shown. The leftmost of the 5 images shows a core from a tissue microarray (scale bar, 200 µm). The middle column within the 5 images shows two images, the top of which is a small field of view (scale bar, 10 µm), and the bottom of which zooms into the area flagged in the top image by a white box (scale bar, 2.5 µm). The right column within the 5 images shows the same fields of view as in the middle column, but post-expansion (yellow scale bar, top 10-12.5 µm, bottom 2.5-3.1 µm; physical size post-expansion, top 50 µm, bottom 12.5 µm; expansion factors 4.0-5.0x, see Table 2 for the detail). The samples were stained with DAPI and multiple antibodies. Blue, DAPI; green, vimentin; red, KRT19.
Figure 2:
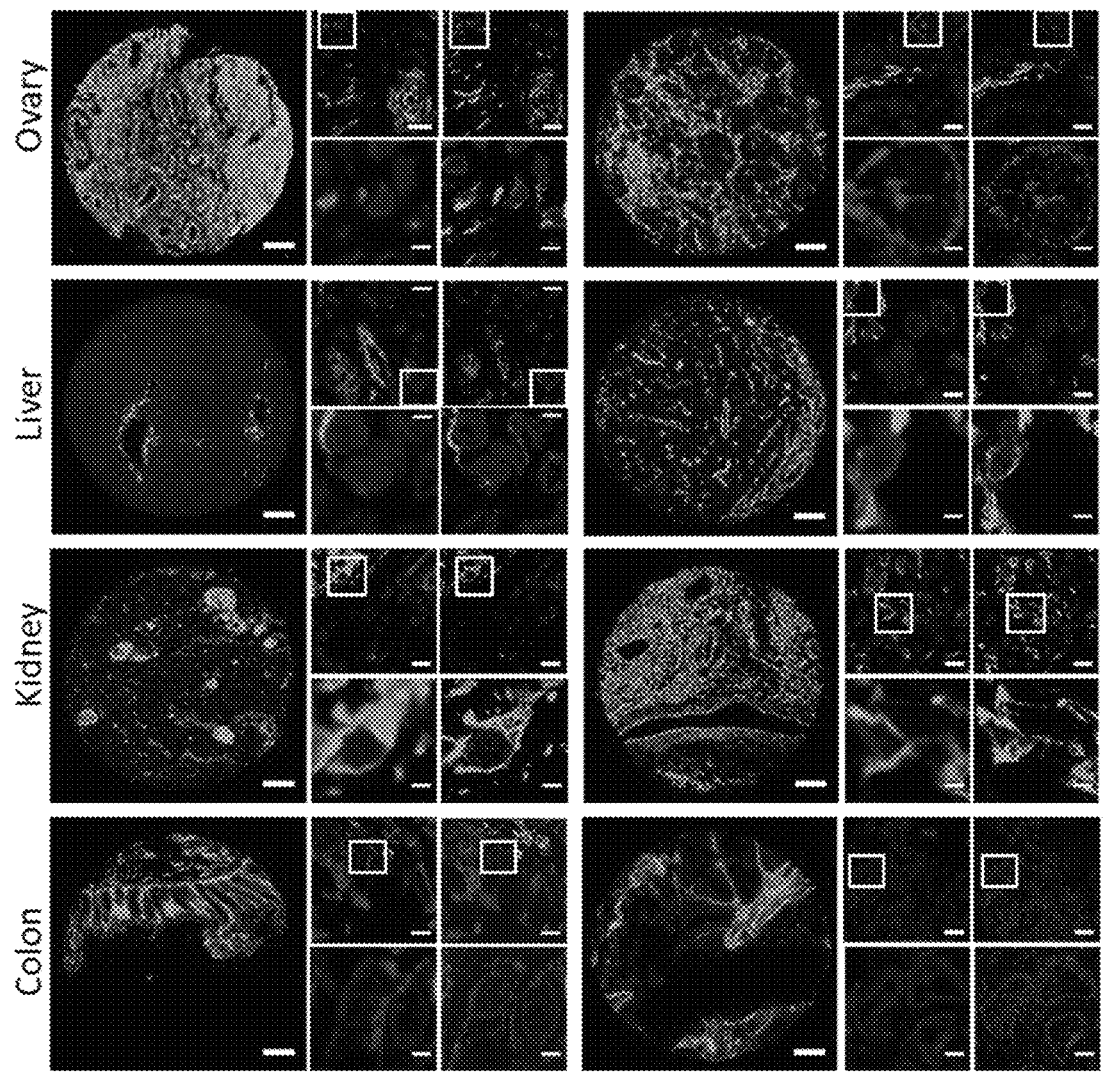
Figure 4:
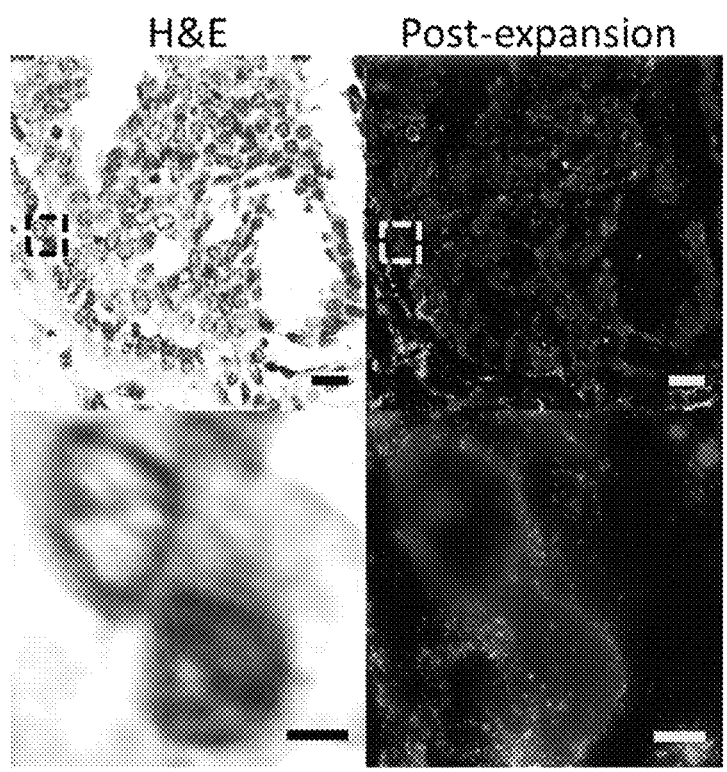
FIG. 4 Representative images of a benign breast lesion Hematoxylin and Eosin (H&E) stained slide before and after treatment of expansion. For the post-expansion images, blue: DAPI, green: Vimentin, red: Hsp60 (mitochondria). Scale bar: top left, 15 µm; top right, 65 µm; bottom left, 2.5 µm; bottom right, 12 µm.

In some embodiments, imaging of the expanded clinical tissue samples can be done with a conventional fluorescent, confocal microscope, or other desired scopes. Pre- and post-expansion images of clinical tissues samples were acquired on an Andor Revolution Spinning Disk Confocal by placing the pre- and post-expanded clinical tissue samples in glass-bottom six-well plates (In Vitro Scientific) and held in place by mounting with 1% agarose. Images were taken on a 40×1.10 NA (Nikon) water objective with 1× or 1.5× zoom and expansion of a paraffin-embedded tissue microarray is shown in FIG. 2 and reuse and expansion of an H&E stained slide is shown in FIG. 4.

Fluorescent Microscopy after Expansion

Low-magnification images of specimens were imaged on a Nikon Ti-E epifluorescence microscope with a SPECTRA X light engine (Lumencor), and a 5.5 Zyla sCMOS camera (Andor), controlled by NIS-Elements AR software, with a 4×0.13 NA air objective or 10×0.2 NA air objective (Nikon). For some images, the images were acquired on the same microscope with a 40×1.15 NA water immersion objective (Nikon). The following filter cubes (Semrock, Rochester, N.Y.) were used: DAPI, DAPI-11LP-A-000; Alexa Fluor 488, GFP-1828A-NTE-ZERO; Alexa Fluor 546, FITC/TXRED-2X-B-NTE; Atto 647N or CF 633, Cy5-4040C-000.

Otherwise, all other presented fluorescent images were imaged using an Andor spinning disk (CSU-X1 Yokogawa) confocal system on a Nikon TI-E microscope body, with a 40×1.15 NA water immersion objective. DAPI was excited with a 405 nm laser, with 450/50 emission filter. Alexa Fluor 488 was excited with a 488 nm laser, with 525/40 emission filter. Alexa Fluor 546 was excited with a 561 nm laser with 607/36 emission filter. Atto 647N and CF633 were excited with a 640 nm laser with 685/40 emission filter.

Brightfield Microscopy

Low magnification images were acquired on a Nikon Ti-E microscope with a DS-Ri2 sCMOS 16 mp Color Camera (Nikon) and white LED light, with a 4×0.13 NA air objective or 10×0.2 NA air objective. High magnification images of H&E slides were acquired on the Pannoramic Scan II (3DHistech), with a 40×0.95 NA air objective (Zeiss).

Autofluorescence Analysis

Tissue-unrelated background was removed from all images by subtraction of mean pixel values from blank regions, prior to analysis. For each fluorescent channel, 10 regions of interest containing brightest fluorescent signals and one area containing autofluorescence signal, judged by a pathologist's visual inspection, were selected, and used to calculate signal-to-background ratios.

Measurement Error Quantification

The same fields of view in different z planes were first imaged pre- and post-expansion. To match the z planes pre- and post-expansion, scale-invariant feature transform (SIFT) keypoints were generated for all the possible combination of pairs of pre- and post-expansion z planes (or z projections). SIFT keypoints were generated using the VLFeat open source library and filtered by random sample consensus (RANSAC) with a geometric model limited to rotation, translation, and scaling. The pair of pre- and post-expansion images with the most SIFT keypoints was used for image registration by rotation, translation and uniform scaling, as well as calculation of expansion factors and vector deformation fields. By subtracting the resulting vectors at any two points, the entire population of possible measurements of point-to-point localization error was sampled and the root-mean-square error for such measurements was plotted as a function of measurement length.

Computational Nuclear Atypia Analysis

Figure 9A:
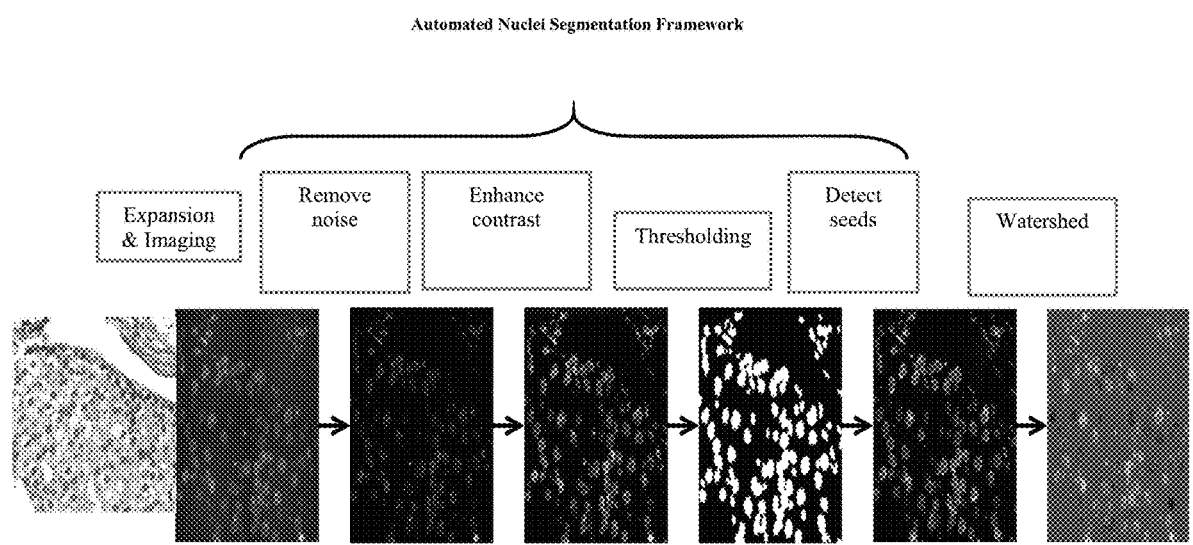
FIG. 9A through FIG. 9C ExPath significantly improves computational diagnosis in early breast lesions. (A) Automated segmentation framework: steps of the image pre-processing and nuclei segmentation pipeline: noise removing using rolling ball correction→enhancing contrast by histogram equalization→nuclei segmentation by minimum error thresholding→seed detection by multi-scale Laplacian of Gaussian (LoG) filter→nuclei splitting by marker-controlled watershed. (B) Computational detection and segmentation of the nuclei is significantly more accurate in expanded samples as compared to pre-expanded samples: example of atypical ductal hyperplasia (ADH); green, true positive; red, false negative; blue, false positive). (C) Classification models were built using L1-regularized logistic regression (GLMNET classifier). Classification accuracy was measured as the area under the receiver operator curve (AUC) achieved by the classification model in cross-validation. ExPath improves automated diagnosis in early breast neoplasia lesions: we applied this image classification framework on both pre-expanded H&E and expanded images for computational differentiation of normal, benign and pre-invasive malignant breast diseases. Both data sets consist of 105 images, containing 36 normal breast tissue images, 31 benign breast tissue images (15 UDH and 16 ADH) and 38 non-invasive breast cancer tissue images (DCIS). Average expansion factor: 4.8 (SD: 0.3). *P<0.05, bootstrapped paired t-test. P value for each binary comparison: Normal vs. UDH (0.17); Normal vs. ADH (0.34); Normal vs. DCIS (0.24); UDH vs. ADH (0.02); UDH vs. DCIS (0.01); ADH vs. DCIS (0.24).

The following is a proposed framework for classification of expanded breast tissue images into different categories: normal breast, benign breast lesions (UDH and ADH) and non-invasive breast cancer. This image classification framework consists of four components: image preprocessing, nuclei segmentation, features extraction and image classification. The image pre-processing and nuclei segmentation pipelines are shown in FIG. 9A.

Image Pre-Processing

After tissue expansion and biomarker staining of nuclei with DAPI, image acquisition was performed using confocal microscopes at 40× magnification. Due to acquisition of multiple non-overlapping tiles and stitching to produce a single image, these tiles demonstrated rolling ball background noise. During image pre-processing, a rolling-ball background correction algorithm with ball size as average nuclei size was applied to remove uneven background noise. After the background noise removal, a nucleus to background contrast was enhanced by adaptive histogram equalization. These enhanced images were smoothed by median filter of radius 10.

Nuclei Segmentation

The nuclei segmentation procedure consists of three steps. First, nuclei were segmented using a Poisson distribution based minimum error thresholding method. Standard and global thresholding methods are not efficient as minimum error threshold method, because of high variability in nuclei and background regions. In order to address this issue, this locally adaptive thresholding algorithm selected the threshold by modelling the mixture of two Poisson models using the image histogram. The threshold value was computed by minimizing the relative entropy between the image histogram and the Poisson mixture model. The initial segmentation of nuclei was then improved by a set of morphological operations that include hole-filing and morphological closing to fill holes and combine small fragments of nuclei to form one single nuclei, and morphological opening to remove small non-nuclei regions (e.g., blood vessels, parts of fragmented nuclei and artifacts). This segmentation method may under-segment clustered nuclei that are touching each other. Second, to separate the touching and overlapping nuclei, we used scale-adaptive multi-scale Laplacian of Gaussian (MSLoG) filter to produce local maxima and select seed points for nuclei. In the case of selecting the local maxima points, the constant scale produces imprecise nuclear seed points, since the nuclear size varies considerably in early breast neoplasia lesions. In order to address this problem, scale-adaptive MSLoG filter was applied on a given number of scales and local maximum points in the scale-space response were selected as seed points. Last, these seed points were used as markers for the marker-controlled watershed algorithm to separate touching and overlapping nuclei.

Feature Extraction

After nuclei segmentation, morphological, first-order statistical and second-order statistical features were extracted for each nucleus. The morphological features include shape and geometrical features which reflect the phenotypic information of nuclei. The computed morphological features are area, convex area, perimeter, equivalent perimeter, eccentricity, orientation, solidity, extent, compactness, major axis length, minor axis length, elliptical minor and major radius. The first-order statistical features determined the distribution of gray-level values within the nuclei regions. The computed first-order statistical features are mean, median, mean absolute deviation, standard deviation, interquartile range, skewness and kurtosis. The second-order statistical features determined the variation inside nuclei texture.

Two types of second order statistical features were computed using grey level Haralick co-occurrence and run-length matrices. The co-occurrence matrix GLCM $(i,j; d,\theta)$ is square with dimension Ng where Ng is the total number of grey levels in the image. The value at ith and jth column in the matrix was produced by counting the total occasions a pixel with value i is adjacent to a pixel with value j at a distance d and angle $\theta$. Then the whole matrix was divided by the total number of such comparisons that have been made. Alternatively, each element of GLCM matrix is considered as the probability that a pixel with grey level i is to be found with pixel with grey level j at a distanced and angle $\theta$. Adjacency was defined in four directions (vertical, horizontal, left and right diagonals) with one displacement vector, which produced four GLCMs matrices. Texture information is rotationally invariant. So, the average in all four directions was taken and produced one GLCM matrix. Later, 14 features proposed by Haralick were computed from the GLCM in order to identify texture more compactly. These 14 features are Autocorrelation, Correlation, Contrast, Cluster Shade, Cluster Prominence, Energy, Entropy, Homogeneity, Inverse Difference Normalized, Inverse Difference Moment Normalized, Dissimilarity, Maximum Probability, Information Measure Correlation 1 and Information Measure Correlation 2.

The set of consecutive pixels, with the same grey level, collinear in a given direction, constitutes a grey level run length matrix GLRLM $(i,j; d,\theta)$. The dimension of GLRLM is Ng×R, where Ng is the number of grey levels and R is the maximum run length. Similar to the GLCM, GLRLMs were computed for four directions and later average them. The 11 run-length features, derived from GLRLM, are short run emphasis (SRE), long run emphasis (LRE), grey-level non-uniformity (GLN), run length non-uniformity (RLN), ratio-percentage (RP), low grey level runs emphasis (LGLRE), high grey level runs emphasis (HGLRE), short run low grey level emphasis (SRLGLE), short run high grey level emphasis (SRHGLE), long run low grey level emphasis (LRLGLE) and long run high grey level emphasis (LRHGLE). In total, 45 features were computed for each nucleus. Last, these features were summarized at the image level by computing the first-order statistics including mean, median, mean absolute deviation, standard deviation, interquartile range, skewness and kurtosis of each feature per image, producing 315 summary features per image.

Image Classification

During the last part of the framework, logistic regression was performed with Lasso regularization to build multivariate image feature-based models to classify normal, benign and pre-invasive malignant tissue images. The analyses were implemented in R, using the glmnet package. Lasso regularization was used to create simpler models, less prone to overfitting, than those that would be obtained from standard logistic regression. The Lasso procedure consists of performing logistic regression with an L1 regularization penalty, which has the effect of shrinking the regression weights of the least predictive features to 0. The amount of the penalty (and the number of non-zero features in the model) is determined by the regularization parameter $\lambda$. This method has been shown to perform well in the setting of colinearity and has been widely used to build predictive models from high-dimensional data in translational cancer research. Features were standardized separately in the training and validation data-sets prior to model construction, using the selected setting in glmnet. Model performance with 6 fold cross validation (6F-CV) was evaluated. For validation, the value of $\lambda$ that achieved the maximum area under curve (AUC) in cross-validation was selected on the training fold data-set and applied this fixed model to the validation fold data-set. Model performance was assessed by computing the area under the receiver operator curve (AUC) of true positives vs. false positives, where a perfect classifier would achieve an AUC of 1, while a random classifier would achieve an AUC of 0.5.

The evaluation of the framework was also performed using two other machine learning classifiers, which are commonly used in biomedical research. A random forest classifier fits a number of decision trees on various sub-samples of the dataset and use averaging to improve the predictive accuracy and control over-fitting. Number of trees (numTrees), maximum depth of the tree (maxDepth) and number of features (numFeatures) to be used in random selection are three parameters that affect the random forest performance. In the experiments numTrees=100, maxDepth=30 and numFeatures=20 were used. The last classifier is Naïve Bayes, which is a probabilistic classifier based on applying Bayes' theorem with strong independence assumptions between the features. As the predicted value is class label (e.g., we are pursuing a classification problem), the independence assumption is less restrictive for classification as compared to regression.

Image Classification Results

Figure 9B:
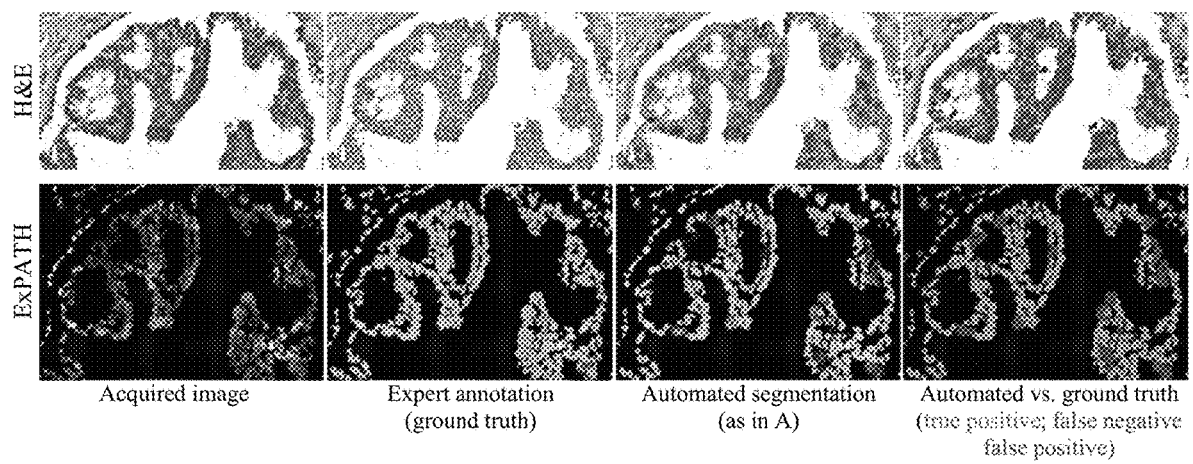
Figure 9C:
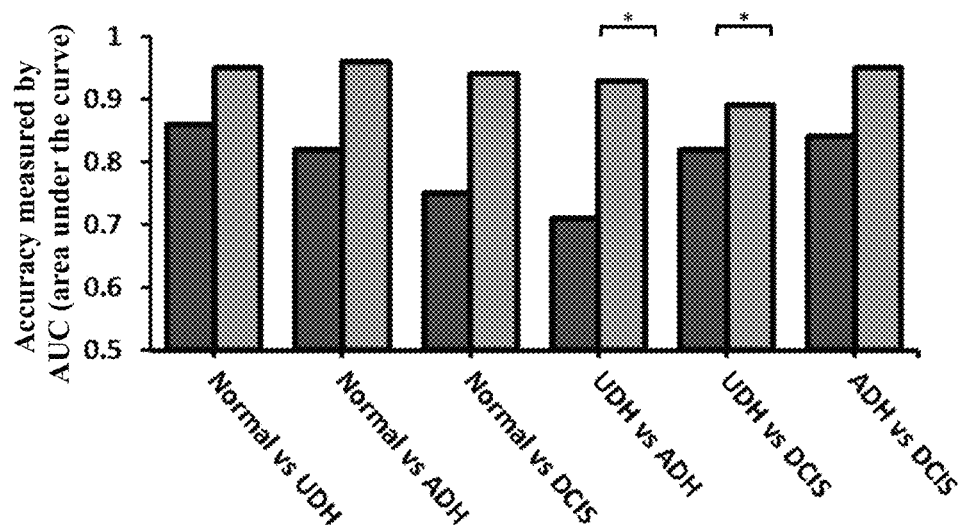

Image classification framework was applied on both pre-expanded and expanded images. Both data sets consist of 105 images containing 36 normal breast tissue images, 31 non-invasive lesion breast tissue images (15 UDH and 16 ADH) and 38 pre-invasive breast tissue images (DCIS). So these 105 images belong to 4 different classes (Normal, UDH, ADH and DCIS). The total number of cases was 131; 105 cases were analyzed and 26 were excluded because they were judged to be borderline diagnostic cases. In order to discriminate normal breast tissue with each non-invasive and pre-invasive breast tissue types, binary classification was performed for all classes and results are shown in FIG. 9C. In order to discriminate normal breast tissue with UDH, ADH and DCIS tissue, GLMNET classifier reported AUC 0.95, 0.96 and 0.94 on expanded data as compared to AUC 0.86, 0.82 and 0.75 with pre-expanded data, respectively. For differentiating non-atypical breast tissue (UDH) from atypical breast tissues (ADH and DCIS), GLMNET classifier reported AUC 0.93 and 0.89 on expanded data as compared to AUC 0.71 and 0.82 with pre-expanded data, respectively. For discriminating atypical benign breast tissue (ADH) with pre-invasive breast cancer tissue (DCIS), GLMNET classifier reported AUC 0.95 with expanded data as compared to AUC 0.84 with pre-expanded data.

Clinical Samples and Pathology-Optimized Expansion Microscopy

Three starting states for clinical and pathological tissue samples were considered when devising a series of steps so that different clinical samples would all arrive in a condition optimized for ExM processing (FIG. 1A): formalin fixed paraffin-embedded (FFPE), H&E stained tissue sections, and fresh frozen tissue, all assuming the tissue to be thin-sliced and on a glass slide. FFPE samples were tested first since it was hypothesized that all of the steps required for the other three categories would either be subsets or permutations of the steps required for FFPE tissue processing. It was evaluated whether xylene treatment to remove paraffin, followed by rehydration and a fairly standard antigen retrieval step (e.g., placing samples in 20 mM sodium citrate at pH 8 and 100° C., and then immediately transferring to a 60° C. chamber for 30 mins), could enable samples to be processed. It was found that heavily formalin-fixed human tissues did not expand evenly under the protocol, even after paraffin removal, unless digestion was performed. The effects of EDTA at 1 mM vs. 25 mM concentration in the digestion of human samples including skin, liver, breast and lung, including acetone-fixed as well as FFPE samples (FIG. 3; Table 2) was examined.

TABLE 2

The effects of EDTA concentration on proteinase K digestion of human tissue/hydrogel hybrid samples.

| | Digestion* with 1 mM EDTA | | Digestion with 25 mM EDTA | |
|---|---|---|---|---|
| | Fresh Frozen | FFPE | Fresh Frozen | FFPE |
| Skin | ✓ | ✗ | ✓ | ✓ |
| Liver | ✓ | ✗ | ✓ | ✓ |
| Lung | ✓ | ✓ | ✓ | ✓ |
| Breast | ✓ | ✗ | ✓ | ✓ |

*Digestion condition: 8 units/mL proteinase K solution containing 25 mM Tris (pH 8), 0.25% Triton X-100, 0.4M NaCl, in 60° C. for 3 hours.
✓ Complete digestion.
✗ Incomplete digestion.

The effect of digestion time under both conditions for human skin and liver FFPE samples, which contain distinct extracellular matrix components and exhibit strong autofluorescence in the blue and green fluorescence emission channel due to formalin-fixed extracellular matrix (ECM) proteins, was investigated.

TABLE 3

The effects of EDTA concentration on proteinase K digestion of human tissue/hydrogel hybrid samples as a function of digestion time.

| Human tissue type | EDTA concentration | Digestion time | | | |
|---|---|---|---|---|---|
| | | 0.5 h | 1 h | 1.5 h | 2 h |
| Skin | 1 mM | ✗ | ✗ | ✗ | ✗ |
| | 25 mM | ✓ | ✓ | ✓ | ✓ |
| Liver | 1 mM | ✗ | ✗ | ✗ | ✗ |
| | 25 mM | ✓ | ✓ | ✓ | ✓ |

Figure 3C:
FIG. 3Ai to FIG. 3L depicts conditions that affect the successful expansion of human tissues. (A) Images of human skin samples stained with DAPI (grey) and antibodies against vimentin (green) and ACTA4 (red). The samples were digested with 8 units/mL proteinase K solution containing 25 mM Tris (pH 8), 1 mM EDTA, 0.25% Triton X-100, and 0.4 M NaCl at 60° C. for 0.5 hour (i-iii) or 2 hours (iv-vi). (i and iv) Photograph of human skin-hydrogel hybrid sample in PBS buffer, after digestion for 0.5 hour (i) or 2 hours (iv); (ii) Pre-expansion wide-field fluorescent image from the sample of (i). (iii) Post-expansion wide-field fluorescent image from the sample of (i), with a dashed orange box highlighting regions with autofluorescence in the DAPI channel and distorted vimentin networks post-expansion. (v) Same as (ii) for the sample in (iv). (vi) Same as (iii) for the sample of (iv) with a dashed orange box highlighting regions with autofluorescence in the DAPI channel. (B) Similar to (A), except that the samples were digested with 8 units/mL proteinase K solution containing 25 mM Tris (pH 8), 25 mM EDTA, 0.25% Triton X-100, and 0.4 M NaCl, at 60° C. for 0.5 hour (i-iii) and 2 hours (iv-vi). (C) Photographs of a human liver sample digested with a 1 mM EDTA-based protocol (8 units/mL proteinase K solution containing 25 mM Tris (pH 8), 1 mM EDTA, 0.25% Triton X-100, and 0.4 M NaCl at 60° C. for 0.5 hours and 2 hours. (D) Photographs of a human liver sample digested with a 25 mM EDTA-based protocol (8 units/mL proteinase K solution containing 25 mM Tris (pH 8), 25 mM EDTA, 0.25% Triton X-100, and 0.4 M NaCl at 60° C. for 0.5 hours and 2 hours. (E) Pre-expansion wide-field fluorescent image of human liver sample stained with DAPI (grey) and antibody against ACTA4 (red). The same was digested with a 1 mM EDTA-based protocol for 1 hour. (F) Post-expansion wide-field fluorescent image of the same sample as in E. White dashed line outlines an out-of-focus region caused by distortion. (G) Pre-expansion wide-field fluorescent image of human liver sample stained with DAPI (grey) and antibody against ACTA4 (red). The sample was digested with a 25 mM EDTA-based protocol for 0.5 hour. (H) Post-expansion wide-field fluorescent image of the same sample as in G. (I) Post-expansion confocal image of human lymph node tissue with invaded breast cancer stained with DAPI (blue) and antibody against vimentin (green), and treated with a 1 mM EDTA-based protocol for 3 hours. (J) Post-expansion confocal image of the same tissue as in I, treated with a 25 mM EDTA-based protocol. (K) Post-expansion confocal image of normal human kidney tissue fixed with acetone, and stained with antibody against collagen IV, and treated with 0.1 mg/ml Acryloyl-X prior to in situ polymerization. Cracks are indicated by white arrows. (L) Post-expansion confocal image of the same sample as in K, treated with 0.03 mg/ml Acryloyl-X prior to in situ polymerization. Scale bars: Aii and iii, 9.2 µm (physical size: 40 µm, expansion factor: 4.33). Av and vi, 9.4 µm (physical size: 40 µm, expansion factor: 4.28). Bii and iii, 9 µm (physical size: 40 µm, expansion factor: 4.41). Bv and vi, 8.9 µm (physical size: 40 µm, expansion factor: 4.51). E and F, 119 µm (physical size: 500 µm, expansion factor: 4.22); G and H, 109 µm (physical size: 500 µm, expansion factor: 4.58). (I-L) 40 µm, physical size.
Figure 3D:
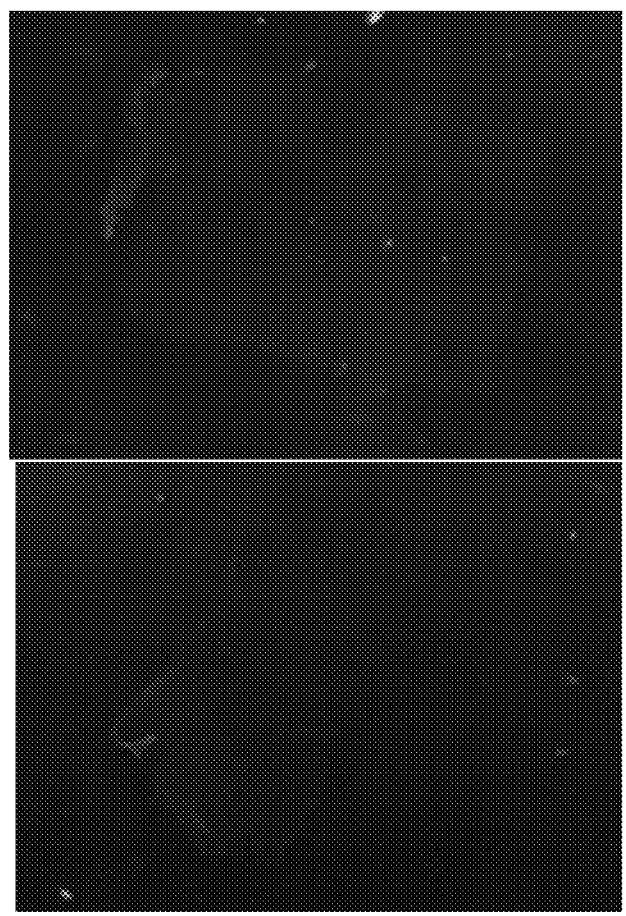
Figure 3E:
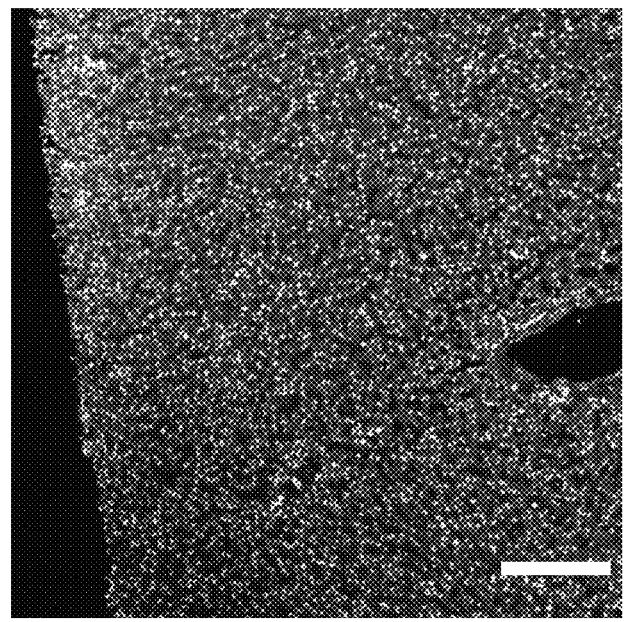
Figure 3F:
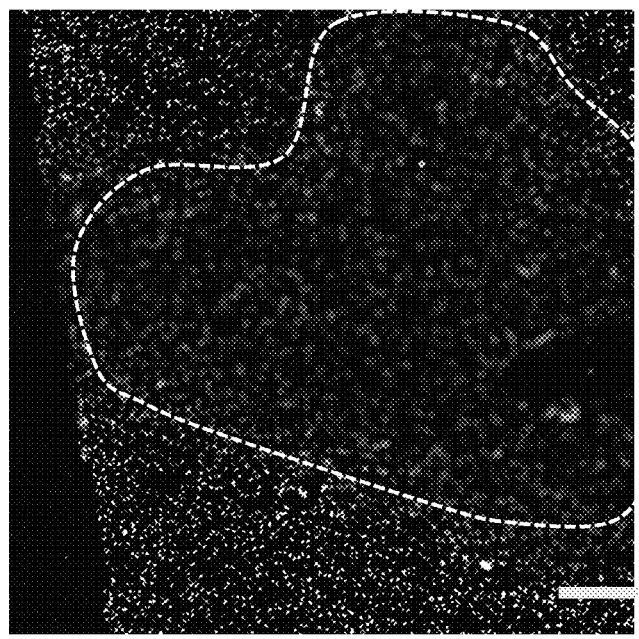
Figure 3G:
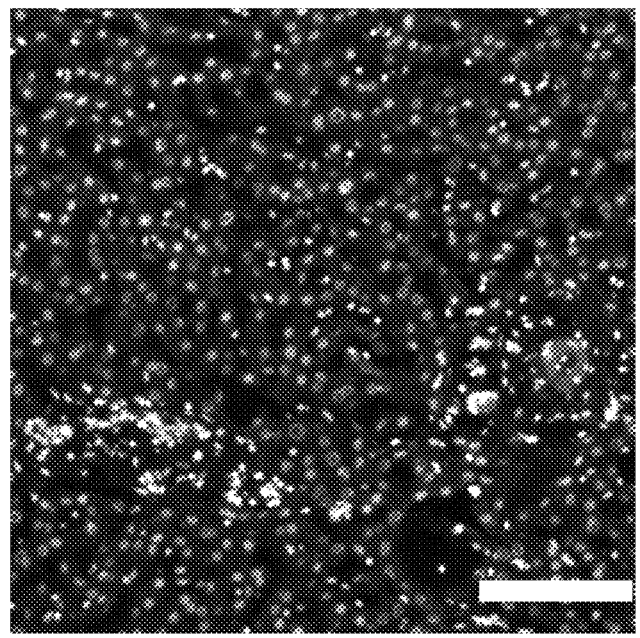
Figure 3H:
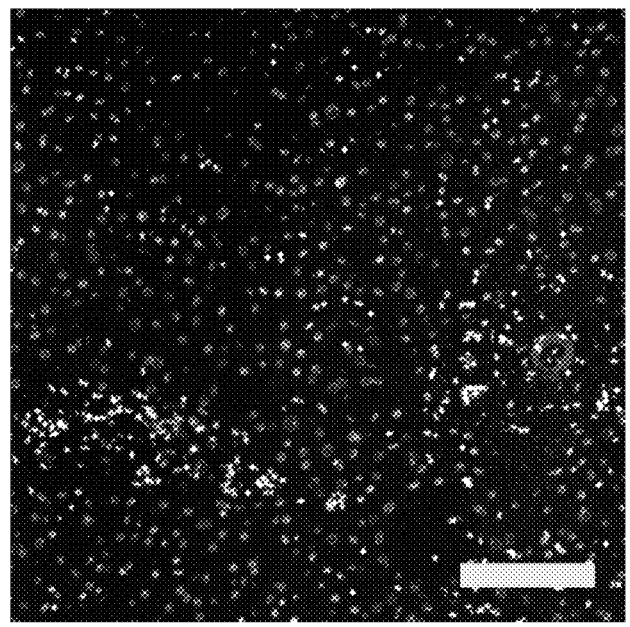
Figure 3I:
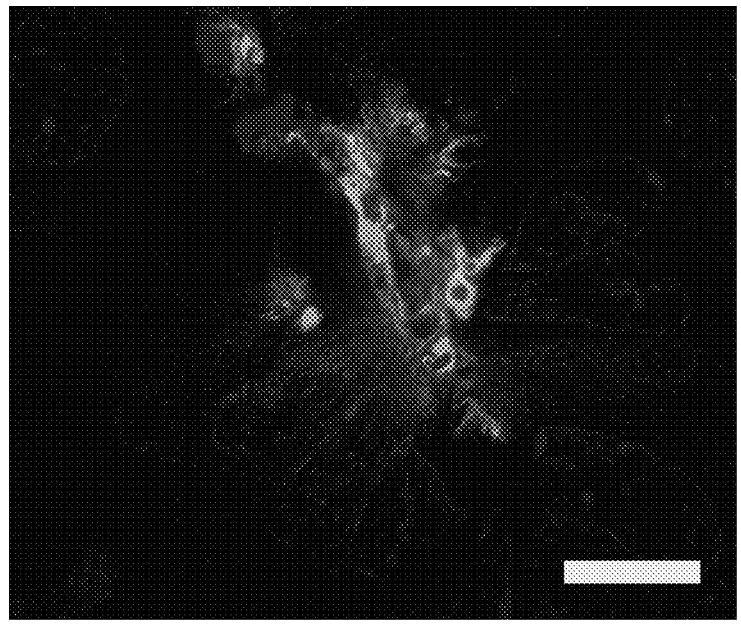
Figure 3J:
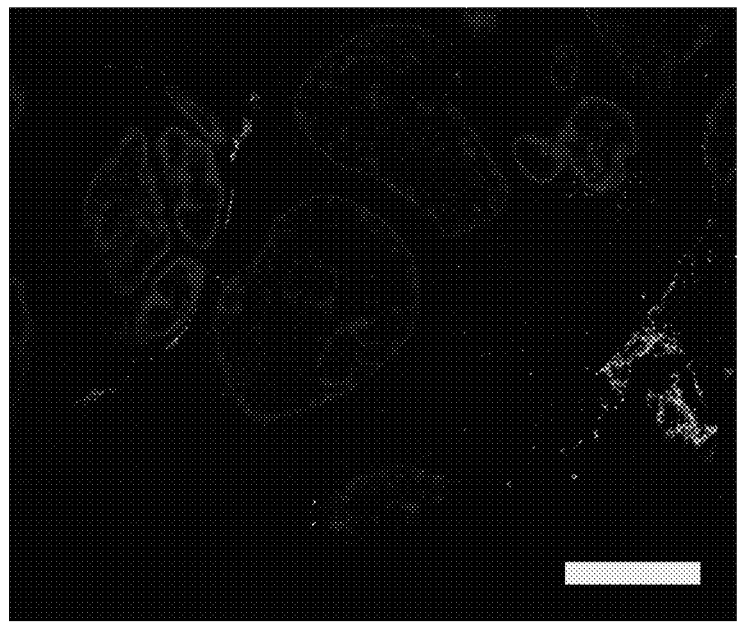
Figure 3K:
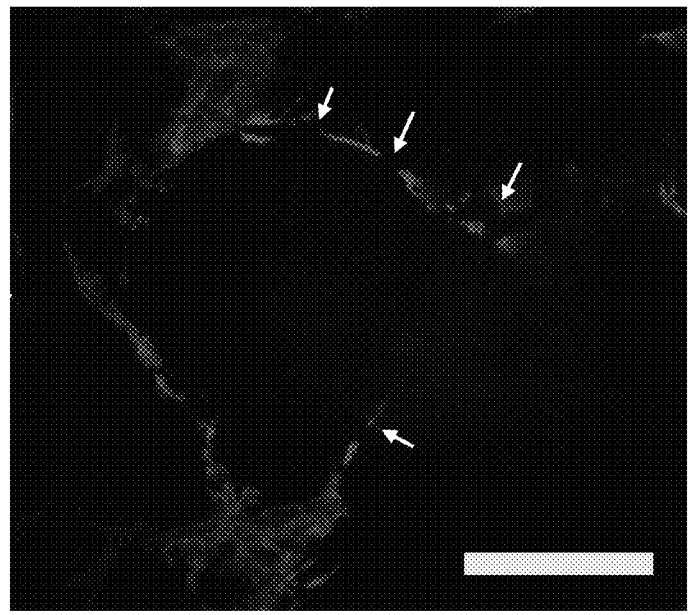
Figure 3L:
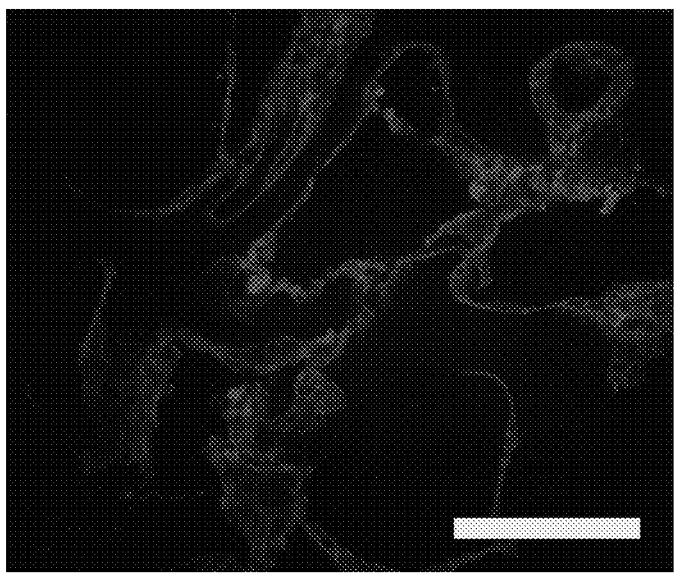

It was found that both human skin and liver samples were completely digested and fully expanded within 0.5 hour with 25 mM EDTA-assisted proteinase K digestion. On the other hand, the ECM was not fully digested in either type of tissue with 1 mM EDTA as indicated by residual autofluorescence (FIG. 3Aiii, Avi). Incomplete digestion can cause distortions at both micro- and macro-scales. As for other types of tissues, both methods suffice.

This FFPE pipeline, with xylene treatment and increased EDTA, could prepare samples for the methods described herein, was validated by assessing the entire pipeline on normal human breast tissues prepared with FFPE preservation. Pre-expansion imaging with either a widefield (FIG. 1B) or SR-SIM (FIG. 1F) microscope, followed by post-expansion imaging on widefield (FIG. 1C) or confocal (FIG. 1G) microscopes respectively, yielded low distortion levels of a few percent (FIGS. 1D, 1E, 1H, and 1I). Thus, this expansion pathology (ExPath), protocol was able to expand paraffin embedded and highly aldehyde-fixed samples.

Having established a basic ExPath pipeline, it was desirable to prepare H&E-stained samples as well. For mounted samples, the cover slip and mounting medium (a hard substance, made out of polystyrene) had to be removed; since xylene treatment was acceptable as a pre-treatment for expansion microscopy, a xylene pre-treatment step was added to dissolve away the mounting medium and result in coverslip removal.

Figure 1J:
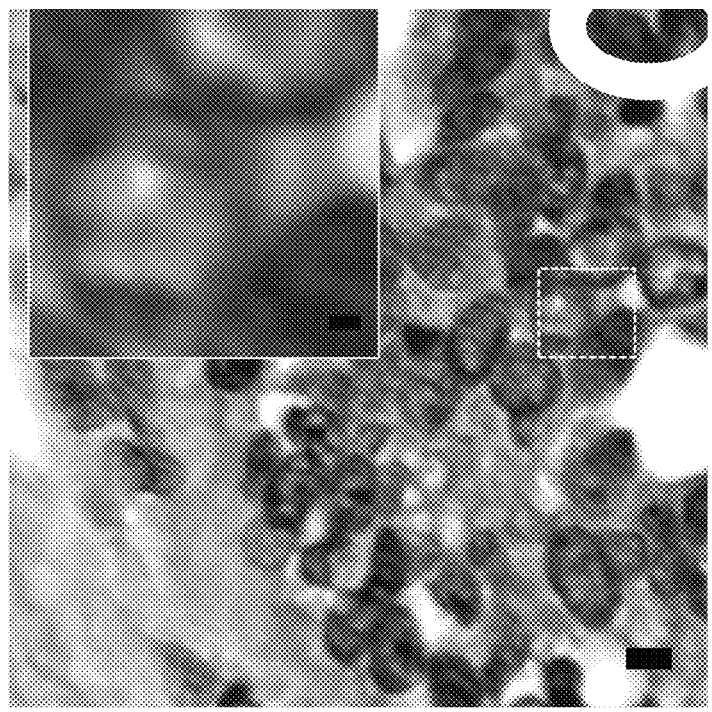
Figure 1K:
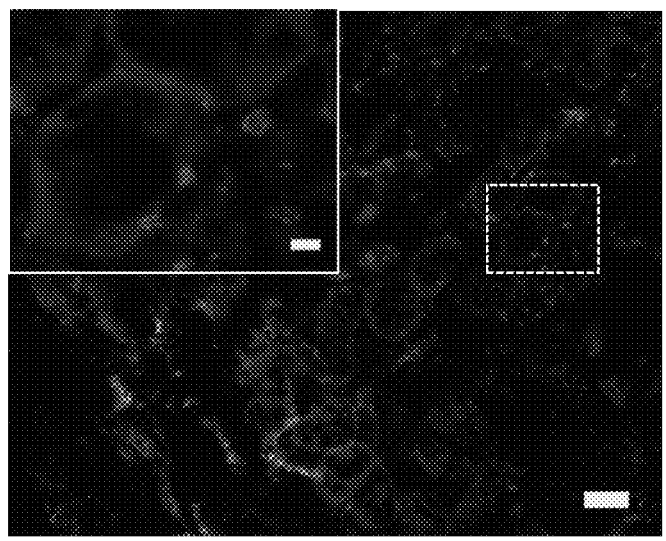

H&E stained tissues exhibit high background fluorescence, suggesting that removal of eosin and hematoxylin would be important for later fluorescent antibody staining. With the ExPath protocol, eosin and hematoxylin were both naturally removed over the time-course of processing. Thus, it was demonstrated that mounted H&E samples could be prepared by visualizing nuclear DNA (stained with DAPI after digestion), as well as applying antibody stains against the mitochondrial protein Hsp60 and vimentin, using an H&E slide of human breast tissue with atypical ductal hyperplasia (ADH) (FIG. 1J, 1K).

Finally, for fresh frozen sections preserved with acetone fixation; it was found that lowering the concentration of AcX from 0.1 mg/mL to 0.03 mg/mL enabled better processing (FIG. 3K, 3L), perhaps because of the greater number of free amines available in tissues that had not been processed with aldehyde.

Figure 1L:
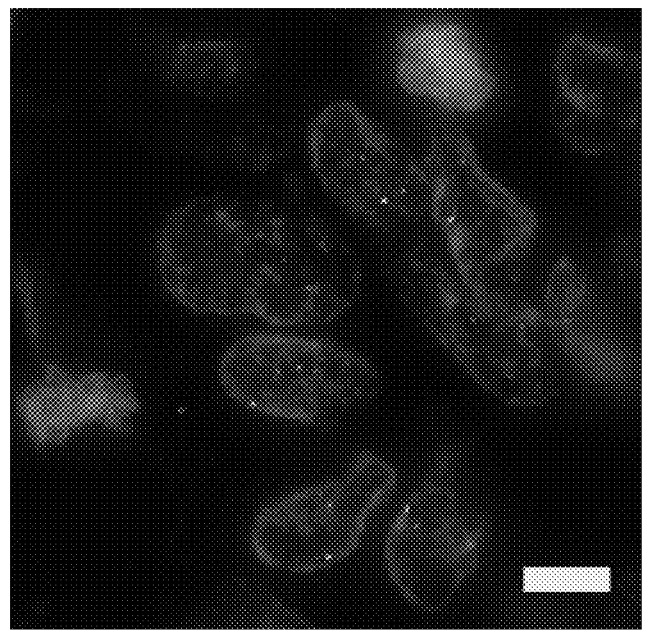
Figure 1M:
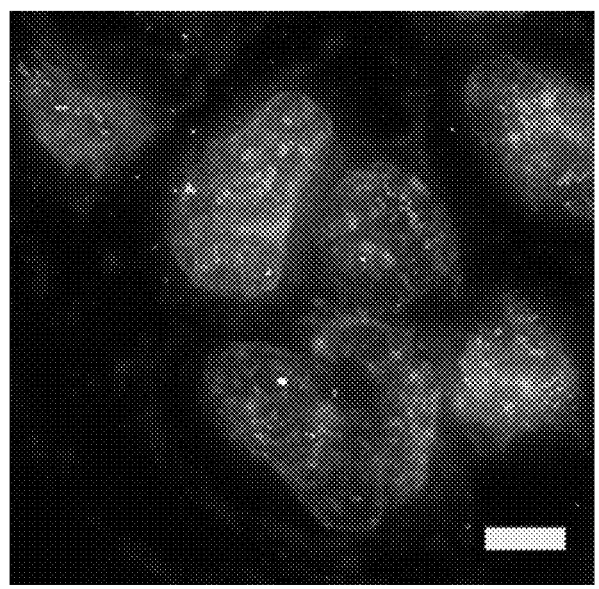

Having established the basic ExPath protocol, the protocol was extended to experimental contexts. For example, DNA fluorescent in situ hybridization (FISH) is commonly used to assess HER2 gene amplification in breast cancer. DAPI was able to stain DNA post-expansion, consistent with gel retention of DNA in expanded samples; therefore, it was examined whether post-expansion DNA FISH was possible. The large size of traditional double-stranded bacterial artificial chromosome (BAC)-based FISH probes (e.g. the length of BAC-based FISH probes targeting HER2 is approximately 220 kb) precludes staining of expanded samples, so commercially available SureFISH probes, which are libraries of single-stranded oligonucleotides with an average size of ~150 bases, targeting HER2 and (as a control) the centrosome of chromosome 17 were chosen. It was observed that SureFISH probes diffused into breast ExPath samples and hybridized with chromosomal DNA, for commercially available specimens of breast cancers with no amplification of HER2 (FIG. 1L) and for cancer with HER2 amplification (FIG. 1M), with much more DNA hybridization apparent in the HER2-amplified case. Since DNA FISH is performed as the final step of the process, it does not interfere with immunostaining which occurs earlier in the protocol. Breast samples were co-stained with an antibody against HER2 protein, and confirmed the correlation of HER2 protein expression with HER2 gene amplification (FIG. 1L, 1M).

ExPath, because it spaces apart molecules and also results in elimination of unwanted molecules, presents several advantages over conventional immunostaining. For example, tissue autofluorescence remains challenging for clinical applications of immunofluorescence and fluorescence in situ hybridization in pathology analysis despite of existing autofluorescence reduction methods. Specimens processed with ExPath are >99% water, and thus transparent and refractive index-matched to water. Thus, the molecular clearing of ExPath, which eliminates unanchored biomolecules (including potentially both proteins as well as small molecules) that contribute to autofluorescence, has a very practical outcome: namely, the reduction of autofluorescence, by an order of magnitude in some spectral channels, as compared to the signal.

ExPath was applied to commercially available tissue microarrays containing dozens of samples from various organs, examining cancer-containing vs. normal tissues from 8 different organs—breast, prostate, lung, colon, pancreas, kidney, liver and ovary, in all cases obtaining expansions of ~4-5x, with average expansion factor 4.7 (standard deviation (SD) 0.2). The expansion variation is smaller than 10%, indicating consistent performance of expansion across different types of human tissues. ExPath revealed sub-diffraction limited structures of intermediate filaments keratin and vimentin, which are critical in the epithelial-mesenchymal transition, cancer progression, and initiation of metastasis (FIG. 2). Given that vimentin is a standard marker of stromal tissue and keratin a standard marker of epithelial tissue, ExPath will provide a simple and convenient way to observe sub-diffraction morphologies of not only nucleic acids, but also protein biomarkers, in clinical biopsy samples from a wide range of human organs.

ExPath Enables Visualization of Human Podocyte Tertiary Foot Processes

Figure 5A:
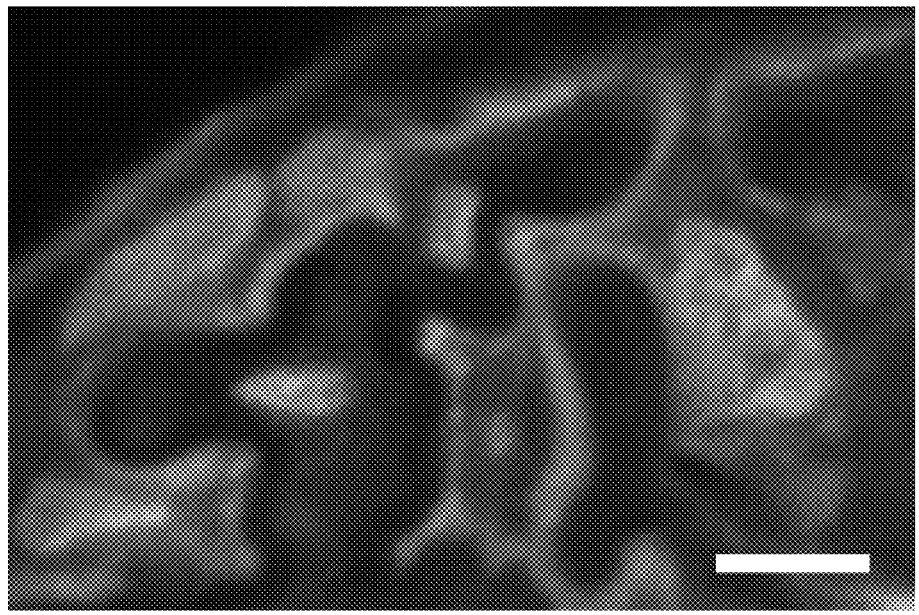
FIG. 5A through FIG. 5G ExPath analysis of clinically relevant nanoscale changes: kidney podocyte foot process effacement. (A) Pre-expansion confocal image of a normal human kidney sample showing part of a glomerulus acquired with a spinning disk confocal microscope, and stained with DAPI as well as multiple antibodies. Blue, vimentin; green, actinin-4; red, collagen IV; grey, DAPI. Orange dotted line indicates where a line cut is analyzed in C. (B) ExPath image of the same sample with the same microscope. Red dotted line indicates where a line cut is analyzed in C. (C) Profiles of actinin-4 intensity along the orange and red dotted lines of (A) and (B). (D) Electron micrograph of a clinical biopsy sample from a normal human kidney. Inset, zoom-in to region outlined by black box (dotted lines); dotted line within the inset indicates where a line cut is analyzed below. Below, electron micrograph feature intensity along the line cut of the inset. (E) ExPath image of a clinical kidney biopsy sample from the same patient analyzed in (D), and stained as in (A). Blue, vimentin; green, actinin-4; red, collagen IV; grey, DAPI. Inset, zoom-in to region outlined by white box (dotted lines); dotted line within the inset indicates where a line cut is analyzed below. Below, actinin-4 intensity along the line cut of the inset. (F) As in D, but for a patient with MCD. (G) As in E, but for the same patient as in F. Scale bars: (A) 5 µm, (B) 5 µm (physical size post-expansion, 23.5 µm; expansion factor: 4.7), (D) 1 µm; inset, 200 nm, (E) 1 (physical size post-expansion, 4.3 µm; expansion factor: 4.3); inset, 200 nm, (F) 1 µm, inset, 200 nm, (G) 1 µm (Physical size post-expansion, 4.2 µm; expansion factor: 4.2); inset, 200 nm.
Figure 5B:
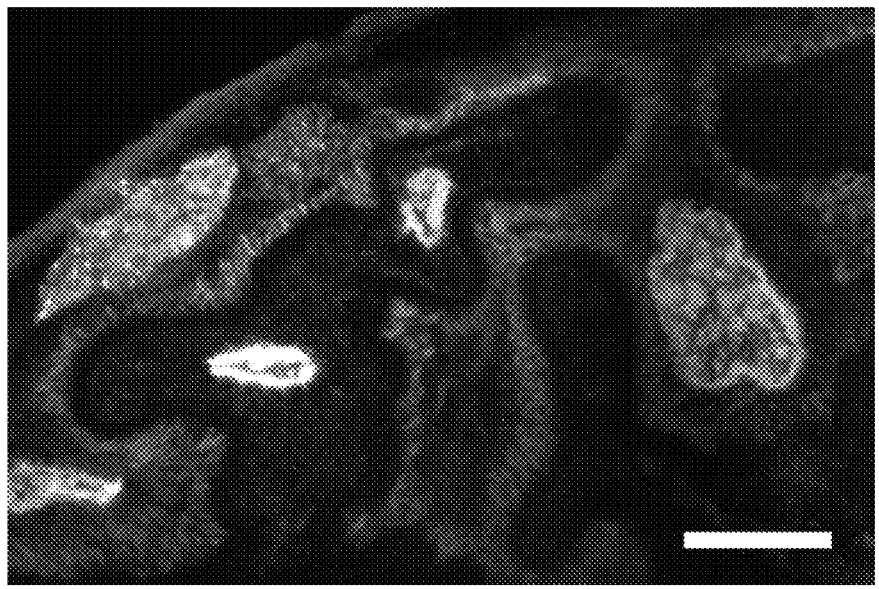
Figure 5C:
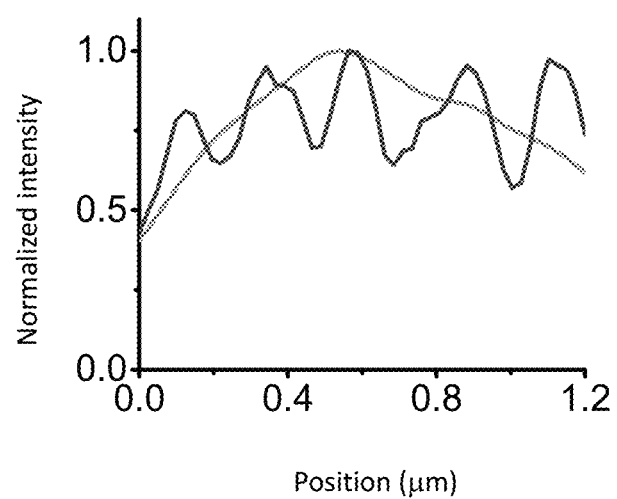
Figures 5D, 5E:
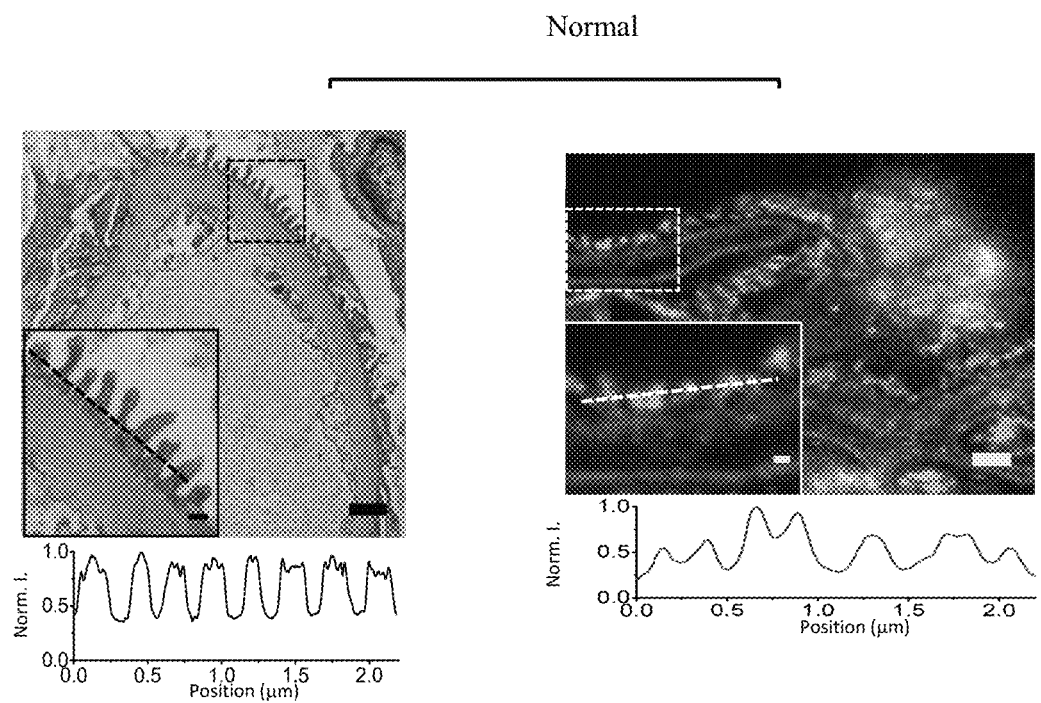
Figures 5F, 5G:
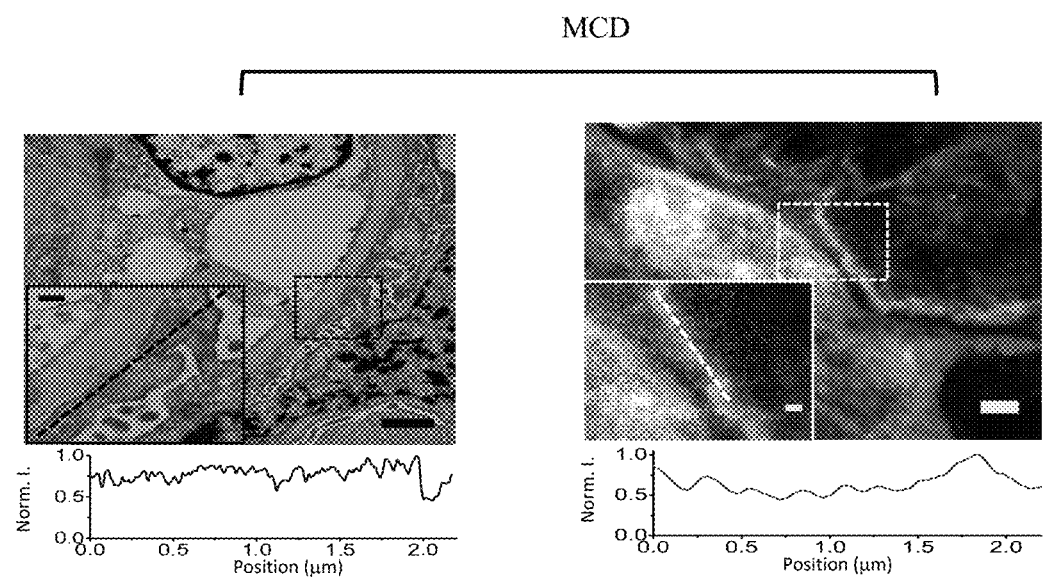
Figure 6A:
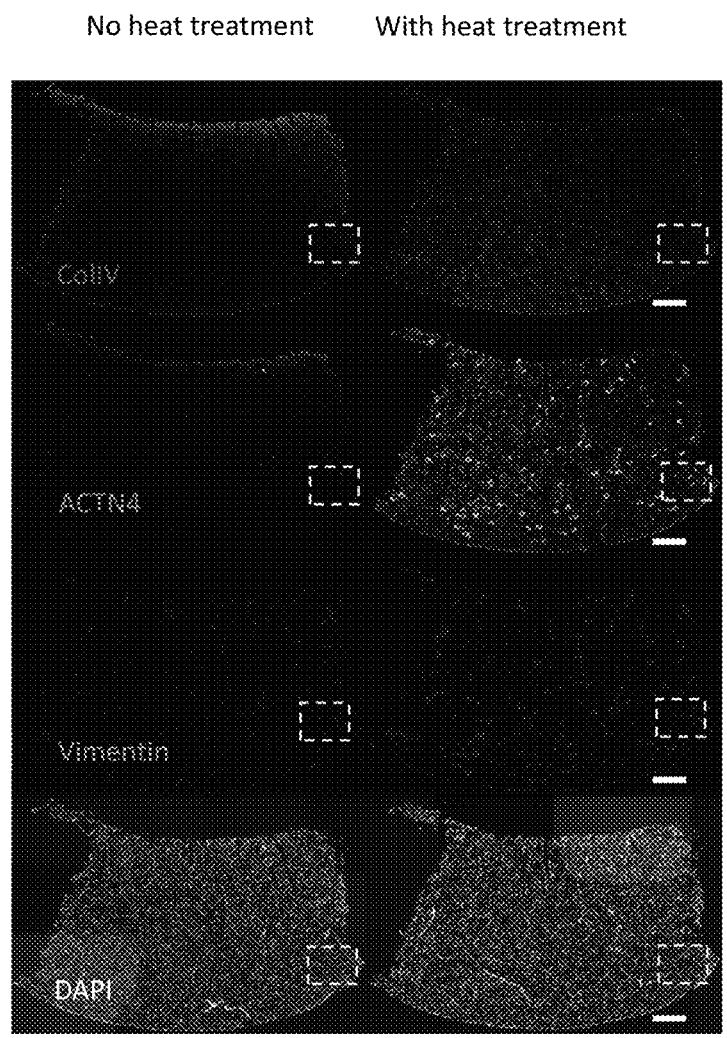
FIG. 6A and FIG. 6B demonstrates that Heat treatment improves immunostaining of Actinin-4 on human kidney samples. (A) widefield fluorescent images of human kidney sections with and without heat treatment in citrate buffer. (B) zoom-in regions corresponding to the regions indicated by the dashed yellow rectangles in the left panels. Scale bars: 1 mm (A), 200 µm (B).
Figure 6B:
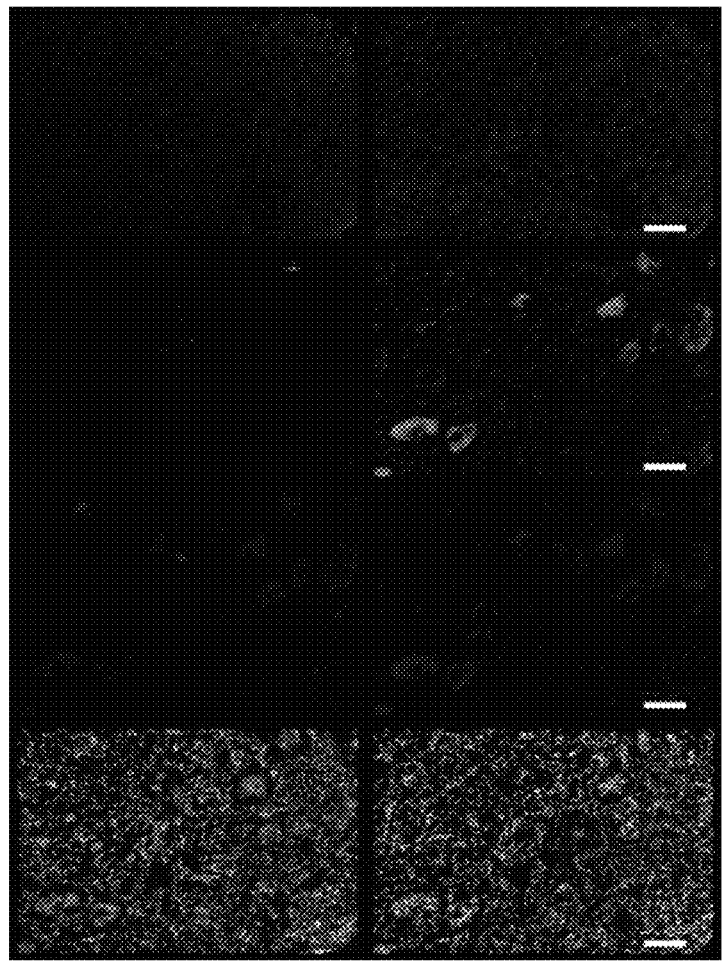
Figure 7A:
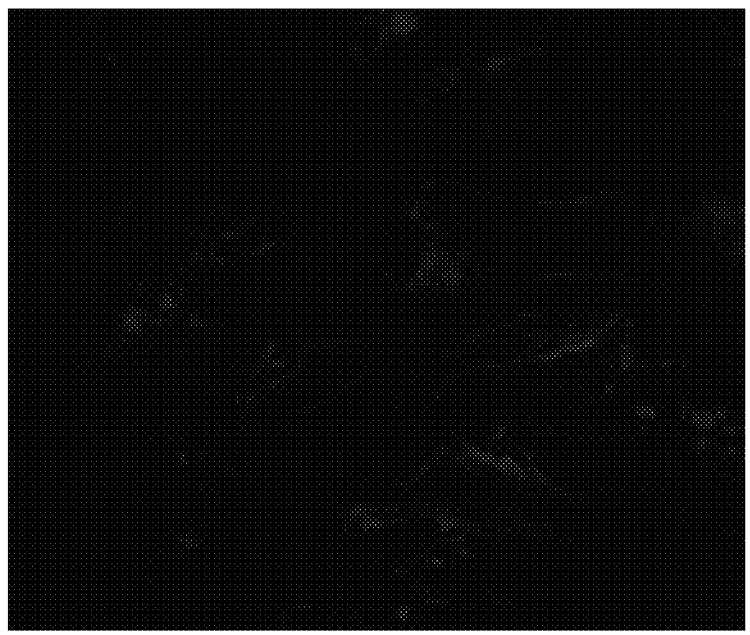
FIG. 7A through FIG. 7H demonstrates that anti-Actinin-4 specifically stains tertiary podocyte foot processes. (A-D) Post-expansion widefield images of a human kidney section stained with DAPI and antibodies. Blue, vimentin; Green, actinin-4; Red, synaptopodin; Grey, DAPI. (E) Merged image of (A-D). (F and G) Magnified regions in actinin-4 (F) and synaptopodin (G) channels from the same sample as taken from the white dashed squares in B and C. (H) Profiles of fluorescent intensities taken along the white dashed line cuts of F and G. Green, actinin-4 red, synaptopodin. Scale bars: 1 µm (4.5 µm physical size, expansion factor 4.5).
Figure 7B:
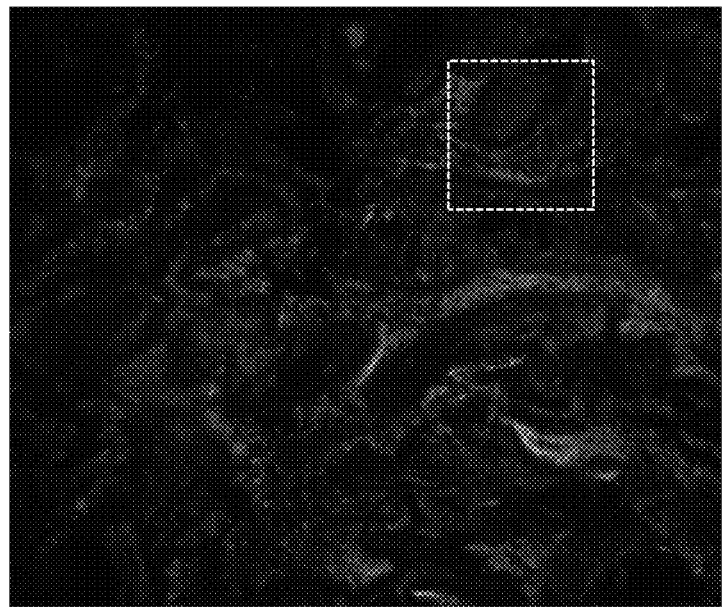
Figure 7C:
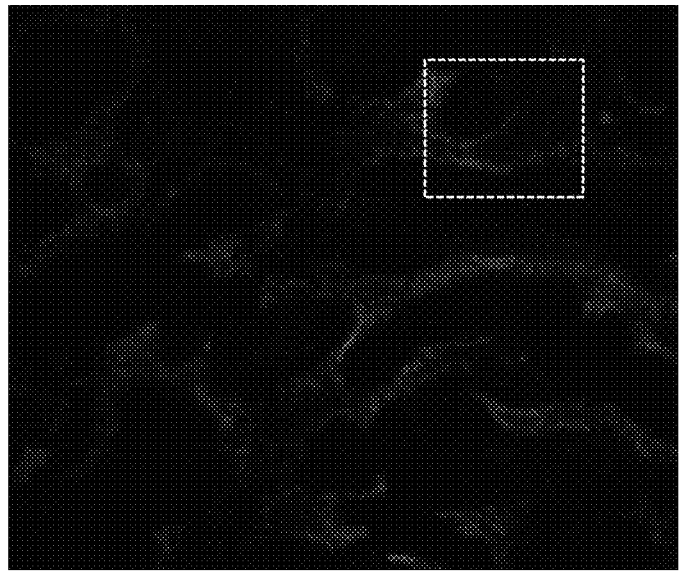
Figure 7D:
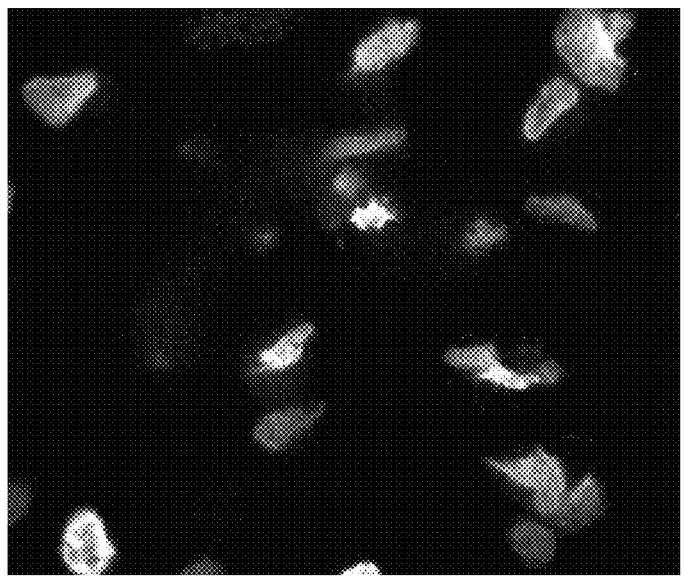
Figure 7E:
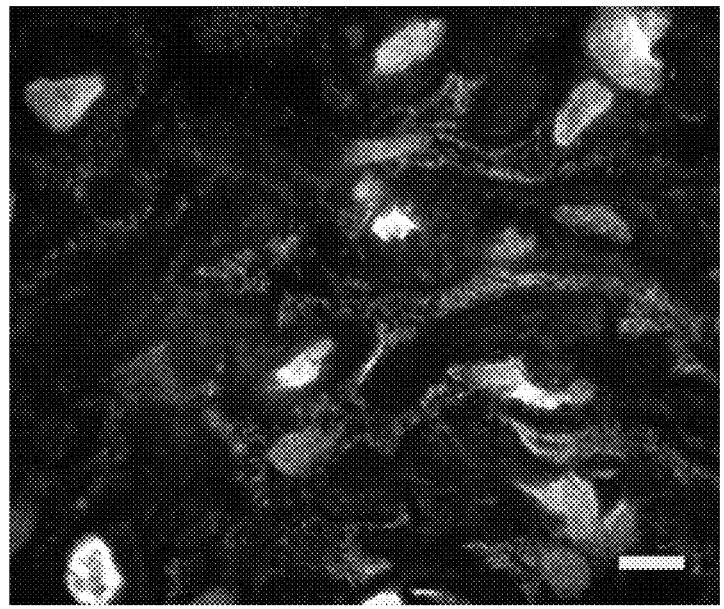
Figure 7F:
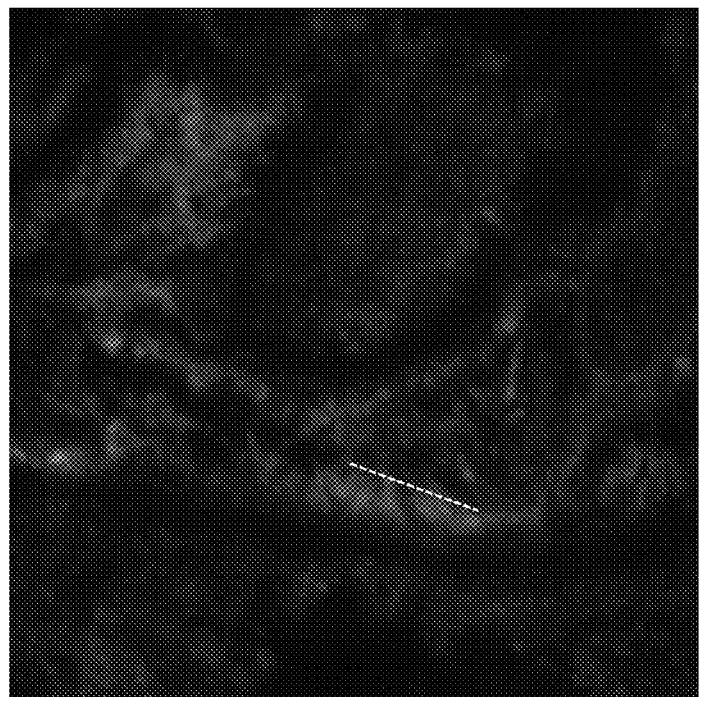
Figure 7G:
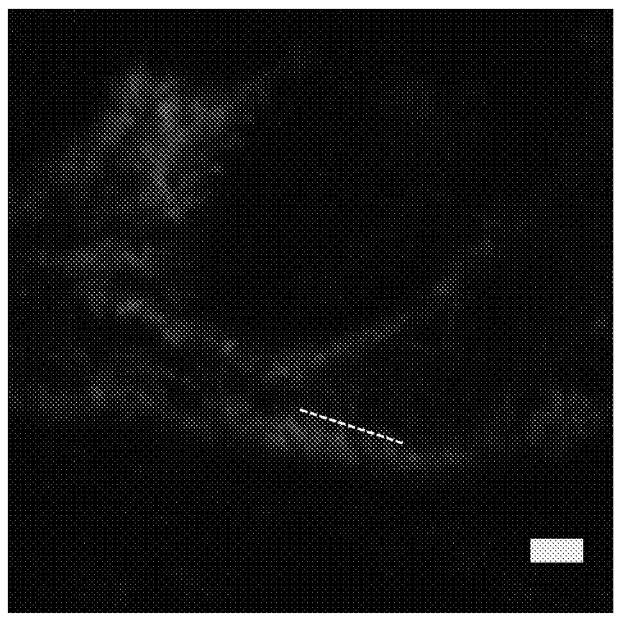
Figure 7H:
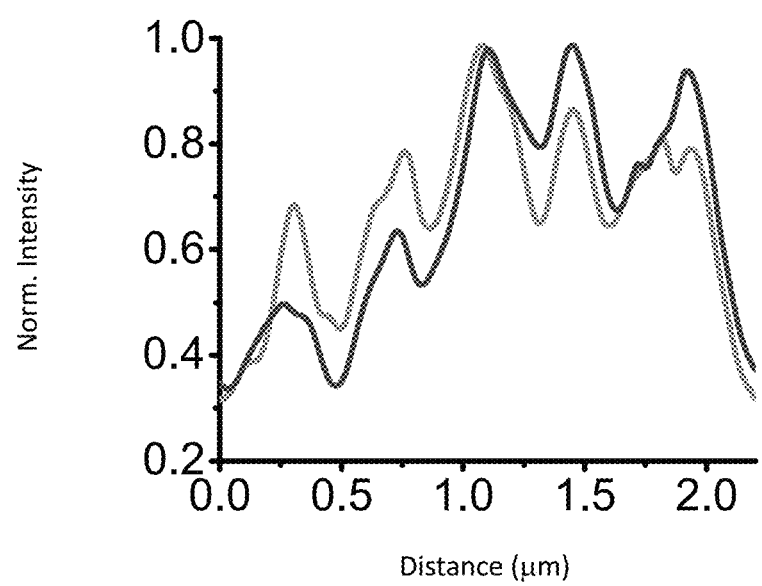
Figure 8A:
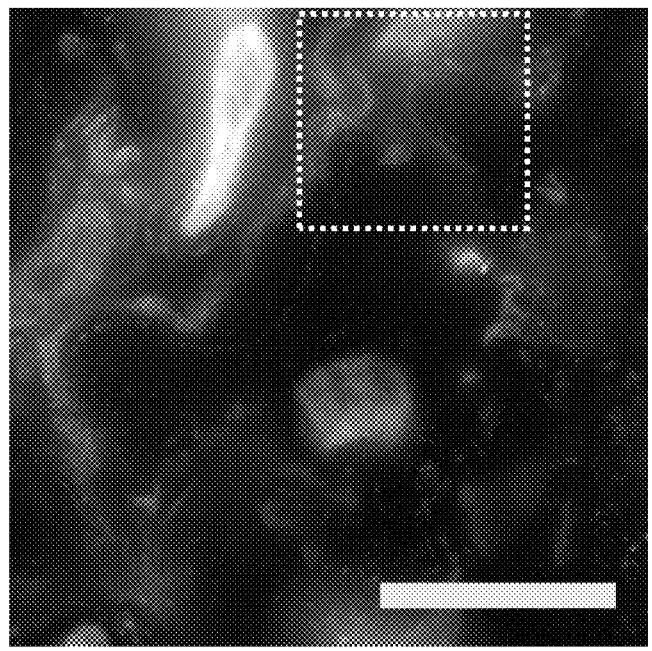
FIG. 8A through FIG. 8H Immunostaining images of kidney FFPE samples. (A). Post-expansion widefield image of a normal human kidney FFPE sample treated with a citrate antigen retrieval method (20 mM sodium citrate, pH 8.0), with magnified region (boxed line) zoomed in in (B). (C) Post-expansion widefield image of a normal human kidney FFPE sample treated with a Tris-EDTA antigen retrieval method (10 mM Tris base, 1 mM EDTA solution, 0.05% Tween 20, pH 9.0), with magnified region (boxed line) zoomed in in (D). (E) Post-expansion confocal image of a normal human kidney FFPE sample treated with a citrate antigen retrieval method, with magnified region (boxed line) zoomed in in (F). (G) Post-expansion confocal image of a human kidney minimal change disease FFPE sample treated with a citrate antigen retrieval method, with magnified region (boxed line) zoomed in in (H). All the samples were stained with DAPI (gray) and antibodies against vimentin (blue), actinin-4 (green) and collagen IV (red). Scale bars: (A), (C), (E) and (G), 40 µm. (B), (D), (F), and (H), 8 µm.
Figure 8B:
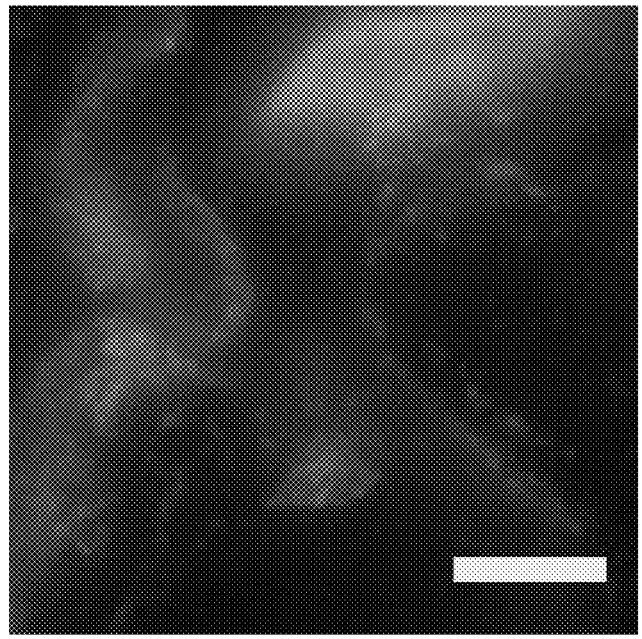
Figure 8C:
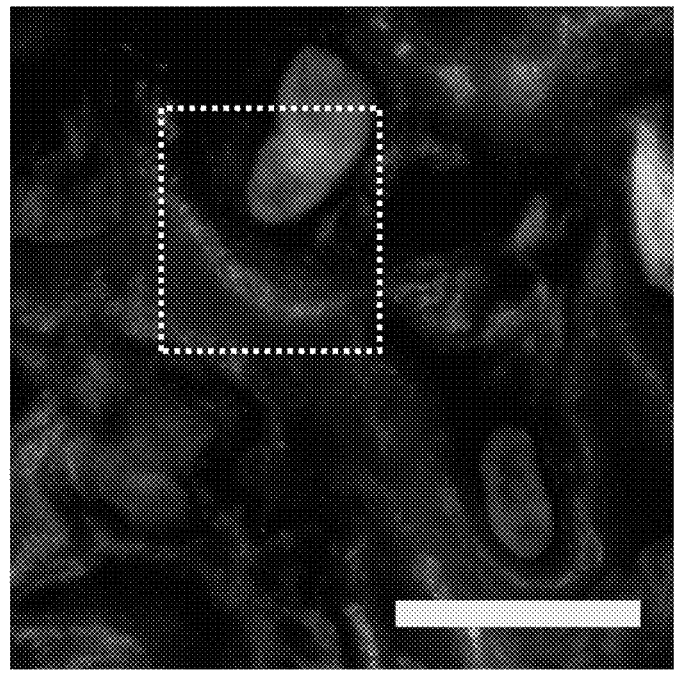
Figure 8D:
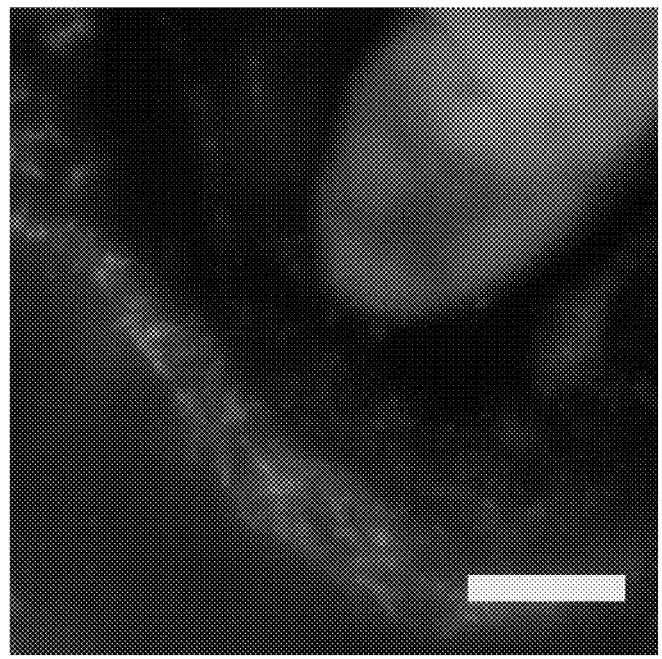
Figure 8E:
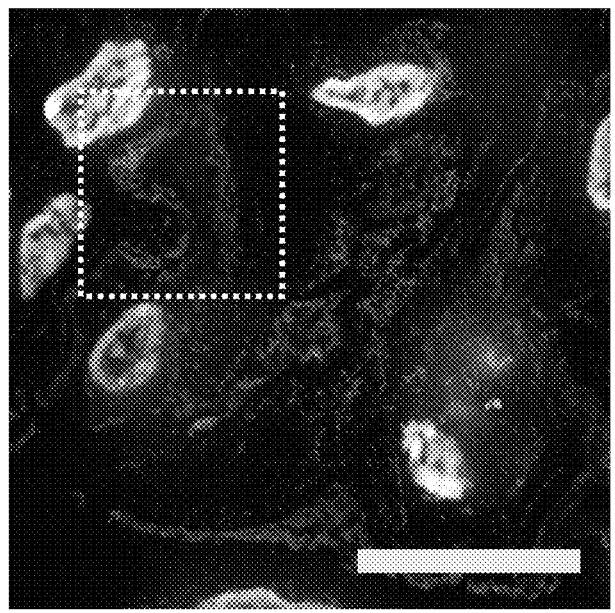
Figure 8F:
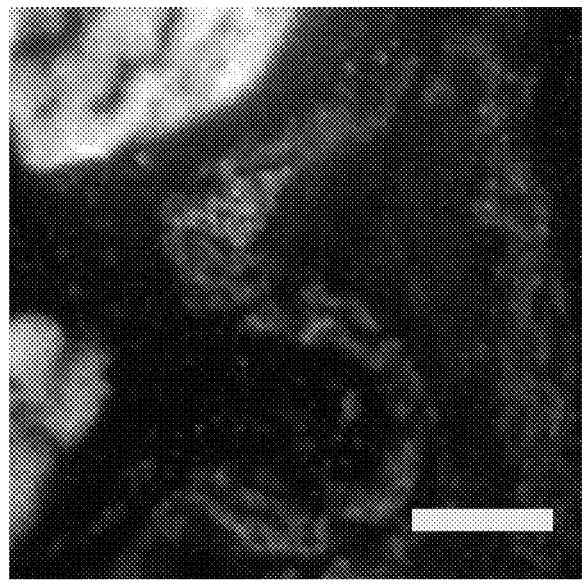
Figure 8G:
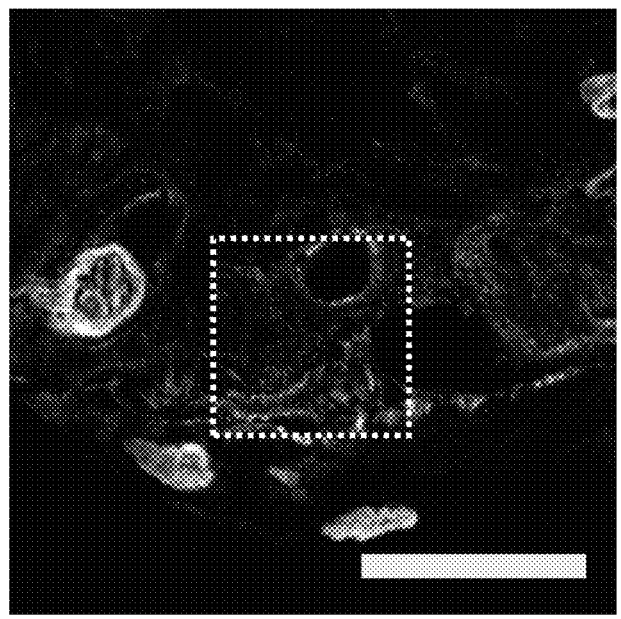
Figure 8H:
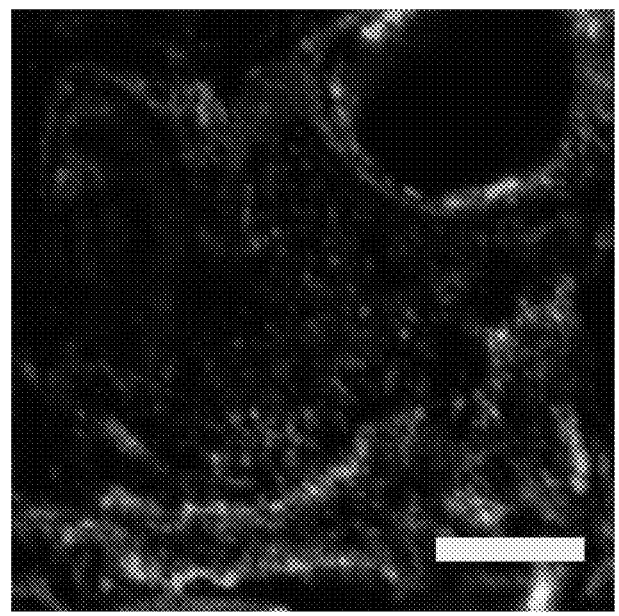

Given that nanoscale imaging has not become widespread in pathology, the ExPath method described herein can be used in the exploration of normal vs. abnormal samples, followed by traditional or automated inspection of key features, both for pinpointing novel pathological mechanisms, as well as for disease classification and refined diagnosis. For example, kidney diseases such as minimal change disease (MCD) and focal segmental glomerulosclerosis (FSGS) (and other lesions associated with nephrotic syndrome) are typically diagnosed or confirmed via electron microscopy. In MCD, kidney tertiary podocyte foot processes, which typically cover the surface of glomerular capillary loops like interdigitating fingers, instead lose their characteristic morphology and appear continuous under electron microscopy—a phenomenon called foot process effacement (FPE). The width of individual foot processes is around 200 nm, beyond the limits of resolution using conventional optical microscopy. It was determined whether ExPath could help with visualization of podocyte foot processes. First a protein target that is specific and abundant in tertiary podocyte foot processes was identified, examining the immunofluorescence of a selection of reported podocyte foot process markers. Among the potential protein targets to show specific and intense podocyte foot process staining, in the ExPath context for acetone-fixed frozen kidney samples that were heat treated prior to immunostaining (FIGS. 6 and 7) was actinin-4. Also identified was anti-synaptopodin[23] antibody suitable for ExPath imaging (FIG. 7). The quality of immunostaining of anti-actinin-4 decreased slightly on kidney FFPE samples treated with either citrate or Tris-EDTA antigen retrieval methods (FIG. 8), compared to that of acetone-fixed frozen kidney samples. The decrease in immunostaining quality might be due to degraded antigenicity caused by formalin-induced crosslinking. Co-staining human kidney samples with anti-actinin-4, as well as antibodies against vimentin (a glomerular marker), and collagen IV (a marker of the basement membrane of capillaries), allowed for observation of the microanatomy of glomeruli (FIG. 5A vs. B), with ExPath revealing the ultrafine structures of tertiary podocyte foot processes (FIG. 5B) vs. conventional confocal imaging (FIG. 5A), in normal human kidney samples (FIG. 5C). Accordingly, fresh-frozen kidney sections from patients with normal kidneys, as well as patients with MCD or FSGS, were stained and expanded. ExPath images were acquired and compared to the electron microscopic images of the corresponding cases. Similar to results in non-clinical human kidney samples, the ultrafine structure of tertiary foot process in the kidneys from normal cases was observed (FIG. 5E), but foot process effacement was observed in MCD cases (FIG. 5G), consistent with the foot process morphologies seen in corresponding EM images from the same samples (FIGS. 5D and 5F). Thus, the nanoscale differences between human clinical samples of nephrotic disease could be visualized with conventional diffraction-limited optical microscopes after sample expansion.

To examine in a blinded study whether ExPath could enable accurate identification of foot process effacement from both MCD and FSGS cases, seven observers, including five pathologists and two non-pathologists, first studied a sample set of immunofluorescent images of kidney glomeruli in both pre-expansion and post-expansion states, and then examined 10 different pre-expansion and 10 post-expansion immunofluorescence images of kidney glomeruli from 3 specimens from normal subjects, 2 from MCD patients and 1 from an FSGS patient. For unexpanded samples, the classification accuracy was only 65.7% (standard deviation (SD) 17%), but increased significantly to 90% (SD 8%) if post-expansion images were used instead (p=0.0088, two tailed t-test). To assess the inter-observer agreement, Fleiss's kappa values were calculated for observers' categorical ratings on both sets of data. Strong consistency on observers' ratings of post-expansion data were found, with kappa value 0.68±0.14 at the 95% confidence level, while inter-observer agreement on pre-expansion data (0.35±0.13, 95% confidence level) was poor—indeed, the kappa value was borderline, given the clinically acceptable threshold of 0.40. ExPath enabled accurate and consistent evaluation among observers on whether the image was from a sample in a normal or abnormal state, from a single post-expansion image (in clinical practice, of course, kidney pathologists normally examine multiple selected EM images for accurate diagnosis). The results suggest that large-scale blinded studies using ExPath may be highly relevant for streamlining the diagnosis or confirmation of nephrotic kidney disease, and potentially other diseases that involve known nanoscale pathology, as well as helping detect diseases earlier when the changes are too small to be resolved with ordinary microscopes.

ExPath Significantly Improves Computational Diagnosis in Early Breast Lesions one of the most challenging problem areas in breast pathology is the classification of early breast lesions. For example, one study has shown that the concordance rate between expert pathologists and pathologists practicing in the community can be quite variable in the classification of non-invasive lesions of the breast, with an agreement of only about 50% for atypical breast lesions. The pathological classification of these lesions provides critically important diagnostic information to prevent over- and under-treatment, and to guide clinical management.

It was hypothesized that the problems with the current classification schemes are due to two issues: first, the diagnostic criteria are largely qualitative and subjective; second, the information contained in the images is limited by the optical diffraction limit of conventional optical microscopes. To begin to address the first issue, computational pathology models were developed that can discriminate benign from malignant intraductal proliferative breast lesions. However, the efficacy of these models is limited by the information extractable from diffraction-limited images. Therefore, ExPath was used to examine the pathological classification of early breast lesions since the extra information obtained from expanded samples might lead to a higher quality of extracted features, in turn resulting in improvements in the reproducible classification of pre-invasive breast lesions.

An automated segmentation framework was applied on pre-expanded H&E-stained images, as well as an image classification framework updated with nucleus detection and segmentation algorithms optimized for post-expansion DAPI-stained images (FIG. 9A). The image classification framework for post-expansion DAPI-stained images includes foreground detection, nucleus seed detection, and nuclear segmentation (FIG. 9A). Following application of the framework, three kinds of features were extracted from each segmented nucleus from both the pre-expanded and post-expanded images: nuclear morphology features, nuclear intensity features, and nuclear texture features.

Each of the two datasets (pre- and post-expansion) consists of 105 images: 36 normal breast tissue images, 31 proliferative lesion (benign) images (15 usual ductal hyperplasia (UDH), 16 atypical ductal hyperplasia (ADH)) and 38 ductal carcinoma in situ (DCIS). All samples were expanded by ~4-5x, with average expansion factor of 4.8 (SD: 0.3). The impact of ExPath on the performance of nuclear detection and segmentation algorithms for a subset of 31 images from both pre-expansion and expanded datasets was assessed (6 normal, 9 UDH, 9 ADH and 7 DCIS; FIG. 9B). Computational detection of nuclei was significantly more accurate in expanded samples (FIG. 9B), with an 11% increase in true positive rate, 22% increase in positive predictive value, and 16% increase in f-score, over non-expanded samples, and segmentation was significantly improved as well, with a 14% increase in f-score, 77% increase in kappa and 66% decrease in global consistency error (GCE). This improved accuracy of nuclear detection and segmentation will help support improved computational pathology analyses. To this end, the classification performance was improved when the models were run on post-expansion data, as compared with pre-expansion data (FIG. 9C). In particular, when examining the area under the receiver operator curve (AUC) of true positives vs. false positives—where a perfect classifier would achieve an AUC of 1, while a random classifier would achieve an AUC of 0.5—the pipeline was able to discriminate lesions such as UDH from atypical lesions such as ADH with an AUC of 0.93 on expanded samples, compared with only 0.71 on the pre-expanded tissue.

These findings suggest that the improved nuclear segmentation achieved on post-expansion images results in more informative features that in turn result in higher-performing classification models. Thus, ExPath can facilitate computational pathology differentiation of proliferative breast lesions, providing diagnostic information which could potentially prevent over- and under-diagnosis and guide clinical management.

While this invention has been particularly shown and described with references to preferred embodiments thereof, it will be understood by those skilled in the art that various changes in form and details may be made therein without departing from the scope of the invention encompassed by the appended claims.

What is claimed:

1. A method for diagnosing neoplastic lesions lesion in an expanded biological tissue sample of a patient comprising providing at least one sample image of the expanded biological tissue sample; providing a computer configured to analyze the sample image; analyzing, with the computer, the sample image, wherein the analyzing comprises detecting and segmenting nuclei in the sample image; calculating, with the computer, molecular characteristics of the detected and segmented nuclei; and determining with the computer, a diagnosis of a neoplastic lesion in the expanded biological tissue sample by comparing the sample image with a normal tissue reference image based on the calculated molecular characteristics of the detected and segmented nuclei of the sample image.

2. The method according to claim 1, wherein the neoplastic lesion is cancer.

3. The method according to claim 2, wherein the cancer is a solid tumor.

4. The method according to claim 3, wherein the solid tumor is selected from breast cancer, ovarian cancer, in particular ovarian adenocarcinoma and ovarian teratocarcinoma, lung cancer, including small cell lung cancer (SCLC) and non-small cell lung cancer (NSCLC), in particular squamous cell lung carcinoma and adenocarcinoma, gastric cancer, hepatic cancer, pancreatic cancer, skin cancer, in particular basal cell carcinoma and squamous cell carcinoma, malignant melanoma, head and neck cancer, in particular malignant pleomorphic adenoma, sarcoma, in particular synovial sarcoma and carcinosarcoma, bile duct cancer, cancer of the urinary bladder, in particular transitional cell carcinoma and papillary carcinoma, kidney cancer, in particular renal cell carcinoma including clear cell renal cell carcinoma and papillary renal cell carcinoma, colon cancer, small bowel cancer, including cancer of the ileum, in particular small bowel adenocarcinoma and adenocarcinoma of the ileum, testicular embryonal carcinoma, placental choriocarcinoma, cervical cancer, testicular cancer, in particular testicular seminoma, testicular teratoma and embryonic testicular cancer, and uterine cancer.

5. The method according to claim 1, wherein the neoplastic lesion is a benign neoplasm.

6. The method according to claim 1, wherein the at least one image of the expanded biological tissue sample is captured using an imaging device.

7. The method according to claim 6, wherein the imaging device is a microscope.

8. A computer-implemented method for diagnosis of cancer or precancerous lesions, the method comprising: (a) providing to a system comprising a computer, information pertaining to at least one image of an expanded tissue sample; (b) evaluating the at least one image of the expanded tissue sample using the computer to apply at least a segmentation analysis to detect and segment nuclei in the at least one image of the expanded tissue sample; and (c) evaluating, using the computer, the detected and segmented nuclei of the evaluated at least one image of the expanded tissue sample of step (b) with an algorithm configured as code that is executed in the computer, wherein the code execution produces an output from the computer comprising a value corresponding to (i) a risk score for cancer occurrence or (ii) a diagnosis of cancer or precancerous lesions in the expanded tissue sample, based on the evaluation of the detected and segmented nuclei of the at least one image of the expanded tissue sample.

9. The method according to claim 8, wherein the expanded tissue sample is a patient's expanded tissue sample, and the method further comprises generating, using the computer, a report based on the risk score for cancer occurrence assigned to the patient or the diagnosis of cancer or precancerous lesions in the patient's expanded tissue sample based on the value corresponding to the risk score for the cancer occurrence or (ii) the diagnosis of cancer or precancerous lesions in the patient's expanded tissue sample.

10. The method according to claim 8, wherein the at least one image of the expanded tissue sample is captured using an imaging device.

11. The method according to claim 10, wherein the imaging device is a microscope or a pathology slide scanner.

12. A method for diagnosing breast cancer in a patient, the method comprising: (1) capturing, with an imaging device, at least one sample image of an expanded tissue sample of the patient; (2) accessing from a database, using a processor configured by a code executed therein, a first patient dataset containing clinical feature data values for the patient corresponding to breast cancer; (3) evaluating, using the processor, the at least one sample image captured by the imaging device and deriving: a. hundreds of molecular feature values indicative of phenotypic information of nuclei/molecular regions of tissue by applying first detection and segmentation of these regions and then computing phenotypic characteristics in the at least one sample image; and b. a plurality of morphometric measurements; (4) updating the first patient dataset using the processor, by associating with the first patient dataset the derived molecular feature values and morphometric measurements; and (5) evaluating, using the processor, the updated patient dataset of step (4) with an algorithm configured as code executed in the processor, where the algorithm configures the processor to output values corresponding to a breast cancer diagnosis of the patient's expanded tissue sample.

13. The method according to claim 12, further comprising generating, using the processor, a report based on the diagnosis of breast cancer in the patient.

14. The method according to claim 12, wherein the imaging device is a microscope.

15. The method according to claim 12, wherein the morphometric measurements relate to the shape, size, intensity distribution and/or texture of the nuclei/molecular regions.

16. The method according to claim 1, wherein the expanded biological tissue sample is prepared by
(a) contacting the biological tissue sample with a bi-functional linker;
(b) permeating the contacted sample with precursors of a swellable material
(c) polymerizing the precursors to form a swellable polymer within the permeated sample, wherein the bi-functional linker attaches to the swellable material; and
(d) incubating the sample comprising the swellable polymer with a non-specific protease in a buffer comprising a metal ion chelator, a nonionic surfactant, and a monovalent salt.

17. The method according to claim 16, wherein the bi-functional linker attaches to the swellable material during polymerization.

18. The method according to claim 16, wherein the bi-functional linker attaches to the swellable material after polymerization.

19. The method according to claim 16, wherein the bi-functional linker comprises a protein-reactive chemical moiety and a gel-reactive chemical moiety.

20. The method according to claim 19, wherein the protein-reactive chemical moiety is a succinimidyl ester of 6-((acryloyl)amino) hexanoic acid (AcX).

21. The method according to claim 16, further comprising expanding the sample comprising the swellable polymer by contacting the swellable polymer with a solvent or liquid to cause the swellable polymer to swell.

22. The method according to claim 16, wherein the biological tissue sample is a previously preserved clinical sample.

23. The method according to claim 22, wherein the biological tissue sample is a formalin fixed paraffin embedded (FFPE) or a hematoxylin and eosin (H&E) stained tissue sample, or a fresh frozen sample.

24. The method according to claim 23, wherein prior to contacting the biological sample with the bi-functional linker, the biological sample is subjected to (i) de-coverslipping the biological tissue sample if it is mounted; (ii) treating the biological tissue sample to mounting medium removal; (iii) treating the biological tissue sample to rehydration if step (ii) is performed; and (iv) subjecting the biological tissue sample to antigen-retrieval.

25. The method according to claim 16 (d), wherein the sample comprising the swellable polymer is incubated with about 1 to about 100 U/ml of a non-specific protease in a buffer having a pH between about 4 and about 12, the buffer comprising about 5 mM to about 100 mM of a metal ion chelator; about 0.1% to about 1.0% of a nonionic surfactant; and about 0.05 M to about 1.0 M monovalent salt.

26. The method of claim 1, wherein the molecular characteristics of the detected and segmented nuclei comprise phenotypical information comprising one or both of morphological and texture appearances of the detected and segmented nuclei.

27. The method of claim 26, wherein the phenotypical information comprises one of more of size, shape, texture, and intensity distribution of the detected and segmented nuclei.

28. The method of claim 12, wherein the phenotypic characteristics comprise morphological and texture appearances.

29. The method of claim 28, wherein the morphological and texture appearances comprise one of more of: size, shape, texture, and intensity distribution of the nuclei/molecular regions.

30. The computer-implemented method of claim 8, wherein the precancerous lesions comprise breast neoplastic lesions.

* * * * *